United States Patent
Haffner et al.

(10) Patent No.: US 7,173,134 B2
(45) Date of Patent: Feb. 6, 2007

(54) SELECTIVE RXR LIGANDS

(75) Inventors: Curt Dale Haffner, Durham, NC (US); Istvan Kaldor, Durham, NC (US); Darryl Lynn McDougald, Durham, NC (US); Aaron Bayne Miller, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 307 days.

(21) Appl. No.: 10/490,805

(22) PCT Filed: Sep. 16, 2002

(86) PCT No.: PCT/US02/29298

§ 371 (c)(1), (2), (4) Date: Mar. 25, 2004

(87) PCT Pub. No.: WO03/027090

PCT Pub. Date: Apr. 3, 2003

(65) Prior Publication Data

US 2004/0198980 A1  Oct. 7, 2004

Related U.S. Application Data

(60) Provisional application No. 60/325,092, filed on Sep. 25, 2001.

(51) Int. Cl.
| | |
|---|---|
| *C07D 491/048* | (2006.01) |
| *C07D 263/56* | (2006.01) |
| *C07D 307/80* | (2006.01) |
| *C07D 307/85* | (2006.01) |
| *C07D 333/56* | (2006.01) |
| *C07D 405/04* | (2006.01) |
| *C07D 411/04* | (2006.01) |

(52) U.S. Cl. ........... 546/115; 548/183; 548/217; 548/465; 549/58; 549/468; 549/471

(58) Field of Classification Search ........... 549/58, 549/468, 471; 548/183, 217, 465; 546/115; 514/302, 365, 375, 414, 443
See application file for complete search history.

(56) References Cited

U.S. PATENT DOCUMENTS

| 5,399,586 A | 3/1995 | Davies et al. |
| 5,962,508 A | 10/1999 | Billoni et al. |
| 6,005,007 A | 12/1999 | Farmer et al. |
| 6,030,952 A | 2/2000 | Diaz et al. |
| 6,162,815 A | 12/2000 | Bernardon |

FOREIGN PATENT DOCUMENTS

| EP | 0 123 998 | 11/1984 |
| EP | 0 909 560 | 4/1999 |
| WO | 94/15902 | 7/1994 |
| WO | 97/24116 | 7/1997 |
| WO | 99/29674 | 6/1999 |
| WO | 02/71827 | 9/2002 |

OTHER PUBLICATIONS

Database Crossfire Beilstein Online! Beilstein Institut zur Forderung der Chemischen Wissenschaften, Franfurt am Main, DE; I. Elghamry: Database accession No. 9073747 XP002235173 abstract & Synth. Commun., vol. 32, No. 6, 2002, pp. 897-902.

*Primary Examiner*—Bernard Dentz
(74) *Attorney, Agent, or Firm*—Amy H. Fix

(57) ABSTRACT

The present invention includes novel retinoid compounds that have selectivity as RXR agonists on one or more isoforms of RXR, currently, RXRα, RXRβ, or RXRγ. The present compounds, and pharmaceutical compositions incorporating these compounds, therefore, are effective in treating conditions mediated by RXRs. Among other physiological responses, the compounds of the present invention reduce blood glucose and maintain body weight, and, thus, are useful for the treatment of diabetes (NIDDIM) and obesity.

1 Claim, No Drawings

SELECTIVE RXR LIGANDS

This application is a 371 of PCT/US02/29298 filed Sep. 16, 2002 which claims the benefit of provisional application 60/325,092 filed Sep. 25, 2001.

FIELD OF THE INVENTION

The present invention generally relates to compounds interacting with retinoid binding proteins, and more particularly to compounds that interact selectively with retinoid X receptors ("RXRs") as well as methods for their production and therapeutic use.

BACKGROUND OF THE INVENTION

Retinoids, both natural and synthetic, are derivatives of vitamin A. Retinoids have been recognized to induce a broad spectrum of biological effects. Thus, retinoid therapy ranges from therapeutic treatments for dermatological conditions, such as acne and psoriasis, to the treatment of metabolic disorders. In addition, RXR selective compounds are believed to be useful for the treatment and prevention of skin diseases, actinic keratoses, arsenic keratoses, inflammatory and non-inflammatory acne, psoriasis, ichthyoses, keratinization and hyperproliferative skin disorders, eczema, atopic dermatitis, Darner's disease, lichen planus, steroid atrophy, topical microbial infections, skin photodamage, type II diabetes, eye disease, retinal detachment, dry eye, corneopathies, cardiovascular disease, dyslipidemias, post-angioplasty restenosis, HPV infections, genital warts, inflammatory disease, ileitis, colitis, Crohn's disease, neurodegeneration, Alzheimer's disease, Parkinson's disease, stroke, pituitary dysfunction, growth hormone deficiency, hair loss, organ rejection, immune disorders, wounds, as well as a variety of cancerous and pre-cancerous conditions, such as acute promyleocytic leukemia, cutaneous T-cell lymphoma, epithelial cancers, squamous cell carcinoma, and breast cancer, as well as in the treatment of hyperthyroidism, dyslipidemia, and hypertension. See, e.g., WO 9712853, WO 0026173, WO 9321146, WO 9504036, WO 0020397, WO 0020370, WO 9845242, EP 0790228, EP 0933350, WO 9908992, WO 9420093, WO 9417796, WO 9639374, EP 0933350, WO 9710819, WO 9963980, WO 9958487, WO 995848, WO 0001679 and Vuligonda et al., Bioorg. Med. Chem. Lett., 9:589–594 (1999).

Retinoids regulate the activity of two distinct nuclear receptor families, the retinoic acid receptors ("RAR") and the retinoid X receptors ("RXR"). As with the RAR subfamily (currently including α, β, and γ isoforms), the RXR subfamily (currently including α, β, and γ isoforms) are recognized as ligand-induced transcription factors. Nevertheless, RARs and RXRs diverge in their primary structure and have only a 27% homology in the ligand binding domains. Thus, these structural differences provide for relative degrees of responsiveness among different retinoids. For example, certain retinoids have been identified that show selective binding to RXRs, but only a weak affinity for RARs. See, e.g., Lala et al., Nature, 83, 450–453 (1996). Furthermore, RARs and RXRs have distinct differences in their tissue distribution. RARs are expressed at high levels in visceral tissues, whereas RXRα is most abundant in the liver, kidney, lung, muscle, and intestine. Thus, while the subfamilies are related, each elicits distinct physiological responses apart from the other. Therefore, retinoids that are selective for either RARs or RXRs would provide for the independent control of the physiological responses mediated by the particular receptors. In addition, RXR dimerizes with many nuclear receptors (e.g., RAR, LXR, VDR, FXR, PPAR, and TR), as well as with itself to form a homodimer. Thus, retinoids that preferentially affect the RXR receptor, may additionally exhibit selectivity for specific heterodimer pairs as well.

SUMMARY OF THE INVENTION

The present invention includes novel retinoid compounds that have selectivity as RXR agonists on one or more isoforms of RXR, namely, RXRα, RXRβ, or RXRγ. The present compounds, and pharmaceutical compositions incorporating these compounds, therefore, are effective in treating conditions mediated by RXRs. Among other physiological responses, the compounds of the present invention reduce blood glucose and maintain body weight, and, thus, are useful for the treatment of diabetes (particularly type II diabetes, or NIDDIM) and obesity. The present invention also includes methods of producing the compounds and methods for the therapeutic use of these novel retinoids and their pharmaceutical compositions.

The present invention includes compounds of Formula I:

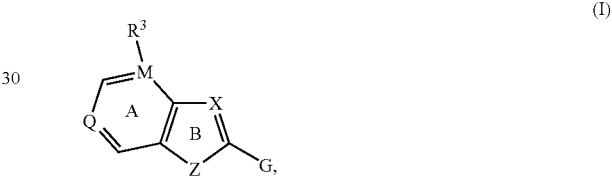

including salts, solvates, and physiologically functional derivatives thereof, wherein the broken lines represent optional double bonds; X is $CR^1$ or N, where $R^1$ is halogen, H, or $CH_3$; Z is O, S, or NH; M is N, C, or $CR^2$, when M is N, the A ring is non-aromatic, when M is C, the A ring is aromatic, when M is $CR^2$, then $R^2$ is H or $—Y(CH_2)_nR^6$, and the A ring is non-aromatic; Y is O or $CH_2$; when n is 0 to 6, $R^6$ is H, alkyl, or $CF_3$, but when n is 2 to 5, $R^6$ is H, alkyl, $CF_3$, $SO_2NHR^{23}$, $NHSO_2R^{23}$, or $NR^{23}R^{24}$, where $R^{23}$ is alkyl, aryl optionally substituted, heteroaryl optionally substituted or combined with $R^{24}$ to form a ring of 3–7 atoms; and $R^{24}$ is H, alkyl, cycloalkyl or combined with $R^{23}$ to form a ring of 3 to 7 atoms; G is $CO_2R^7$, $SO_3R^7$, $PO_3R^7$, CONHOH, or

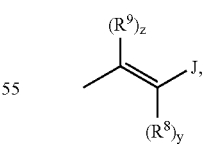

where the broken line represents an optional double bond; J is CHO, $CO_2R^7$, $SO_3R^7$, $PO_3R^7$, CONHOH, or J forms a thiazolidinedione ring with $R^8$; $R^7$ is H or alkyl; $R^8$ and $R^9$ are independently H, halogen, alkyl, or $CF_3$; y and z are each 0, 1, or 2; Q is $CR^4$, $CR^4R^5$, O, $NR^{10}$, or S, where $R^4$ and $R^5$ are independently H or alkyl, provided that when Q is $CR^4$, the A ring is aromatic; $R^{10}$ is alkyl, $COR^{11}$, $CONHR^{11}$, $CO_2R^{11}$, $CONR^{11}R^{12}$, $SO_2R^{11}$, aryl, or cycloalkyl; $R^{11}$ and $R^{12}$ are independently alkyl or cycloalkyl;
$R^3$ is

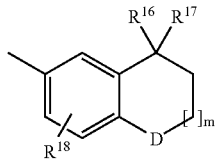

wherein D is $CR^{13}R^{14}$, O, S, $NR^{15}$, CHOH, CO, SO, $SO_2$, where $R^{13}$ and $R^{14}$ are independently H, alkyl, or cycloalkyl; and where $R^{15}$ is H, alkyl, or cycloalkyl; $R^{16}$ and $R^{17}$ independently are H, $C_{1-4}$ alkyl, cycloalkyl, or together form a carbocyclic ring having from 3 to 7 atoms; $R^{18}$ is H, $OR^6$, halogen, $CF_3$, alkenyl, $SR^{16}$, $C_{1-4}$ alkyl, $CO_2R^{16}$, $COR^{11}$, or $NR^{16}R^{17}$, where $R^{16}$ and $R^{17}$ are as above defined; m is 0 or 1;
or $R^3$ is

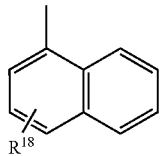

where $R^{18}$ is as defined above;
or $R^3$ is

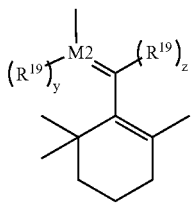

where M2 is C or N, provided however that the optional double bond represented by the broken line is optionally present only when M2 is C; each $R^{19}$ is, independently, H or alkyl; y and z are as defined above;
or $R^3$ is

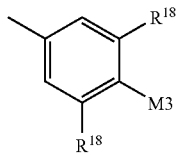

where each $R^{18}$ is, independently, as defined above; and M3 is $C-(R^{16})_3$ or $N-(R^{16})_2$, when M3 is $N-(R^{16})_2$, an $R^{16}$ may combine with an $R^{18}$ to form a 5- or 6-membered ring.

Preferably when either $R^4$ or $R^5$ or both are alkyl, said alkyl is $C_{1-5}$ alkyl; when $R^6$ is alkyl, said alkyl is $C_{1-6}$ alkyl; when $R^7$ is alkyl, said alkyl is $C_{1-5}$ alkyl; when either $R^8$ or $R^9$ or both are alkyl, said alkyl is $C_{1-3}$ alkyl; when $R^{10}$ is alkyl, said alkyl is $C_{1-6}$ alkyl; when either $R^{11}$ or $R^{12}$ or both are alkyl, said alkyl is $C_{1-5}$ alkyl; when either $R^{13}$ or $R^{14}$ or both are alkyl, said alkyl is $C_{1-3}$ alkyl; when $R^{15}$ is alkyl, said alkyl is $C_{1-4}$ alkyl; when either $R^{16}$ or $R^{17}$ or both are alkyl, said alkyl is $C_{1-4}$ alkyl; when $R^{18}$ is alkenyl, said alkenyl is $C_{1-4}$ alkenyl; when $R^{18}$ is alkyl, said alkyl is $C_{1-4}$ alkyl; when $R^{19}$ is alkyl, said alkyl is $C_{1-4}$ alkyl; when $R^{23}$ is alkyl, said alkyl is $C_{1-6}$ alkyl; and when $R^{24}$ is alkyl, said alkyl is $C_{1-7}$ alkyl.

Preferably, X is CH, Z is O, Q is $CH_2$, M is CH, G is

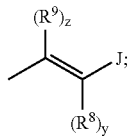

J is $CO_2H$, y and z are each 1, $R^8$ and $R^9$ are H; the double bond exists, and the olefin geometry is trans.

In one embodiment preferably $R^3$ is

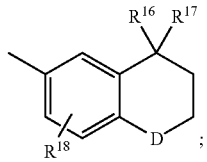

where D is $CR^{13}R^{14}$; $R^{13}$, $R^{14}$, $R^{16}$, and $R^{17}$ are each methyl; and $R^{18}$ is H.

Particularly preferred compounds of formula (I) include:
(2E)-3[4-(5,5,8,8-Tetramethyl-5,6,7,8-tetrahydro-2-naphthalenyl)tetrahydro-1-benzofuran-2-yl]-2-propenoic acid;
(2E)-3-[4-(3,5,5,8,8-pentamethyl-5,6,7,8-tetrahydro-2-naphthalenyl)-4,5,6,7-tetrahydro-1-benzofuran-2-yl]-2-propenoic acid;
(2E)-3-[4-(3-methoxy-5,5,8,8-tetramethyl-5,6,7,8-tetrahydro-2-naphthalenyl)-4,5,6,7-tetrahydro-1-benzofuran-2-yl]-2-propenoic acid;
(2E)-3-[4-(5,5,8,8-tetramethyl-3-propoxy-5,6,7,8-tetrahydro-2-naphthalenyl)-4,5,6,7-tetrahydro-1-benzofuran-2-yl]-2-propenoic acid;
(2E)-3-[6-methyl-4-(5,5,8,8,-tetramethyl-5,6,7,8-tetrahydro-2-naphthalenyl)-4,5,6,7-tetrahydro[2,3-c]pyridin-2-yl]-2-propenoic acid;
(2E)-3-[4-(5,5,8,8-tetramethyl-5,6,7,8-tetrahydro-2-naphthalenyl)-1-benzofuran-2-yl]-2-propenoic acid;
(2E)-3-[4-(5,5,8,8-tetramethyl-5,6,7,8-tetrahydro-2-naphthalenyl)-4,5,6,7-tetrahydro-1-benzothien-2-yl]-2-propenoic acid;
(2E)-3-[4-(5,5,8,8-tetramethyl-5,6,7,8-tetrahydro-2-naphthalenyl)-4,5,6,7-tetrahydro-1,3-benzoxazol-2-yl]-2-propenoic acid;
(2E)-3-(4-{[(2,6,6-trimethylcyclohexen-1-yl)methyl]amino}benzofuran-2-yl)-2-propenoic acid;
(2E)-3[4-(4-Isopropoxy-1-naphthalenyl)tetrahydro-1-benzofuran-2-yl]-2-propenoic acid;
(2E)-3-{4-[4-Dimethylamino)-3-ethylphenyl]-4,5,6,7-tetrahydro-1-benzofuran-2-yl}-2-propenoic acid;
(2E)-3-{4-[(E)-2-(2,6,6-Trimethyl-1-cyclohexen-1-yl)ethenyl]-1-benzofuran-2-yl}-2-propenoic acid;
4-(5,5,8,8-Tetramethyl-5,6,7,8-tetrahydro-2-naphthalenyl)-4,5,6,7-tetrahydro-1-benzofuran-2-carboxylic acid;

[4-(5,5,8,8,-Tetramethyl-5,6,7,8-tetrahydro-2-naphthalenyl)-4,5,6,7-tetrahydro-1-benzofuran]-2-(2,4-thiazolidinedione);

[4(5,5,8,8,-Tetramethyl-5,6,7,8-tetrahydro-2-naphthalenyl)-4,5,6,7-tetrahydro-1-benzothiaphene]-2-propionic acid;

4-(5,5,8,8,-Tetramethyl-5,6,7,8-tetrahydro-2-naphthalenyl)-4,5,6,7-tetrahydro-1-benzofuran]-2-(2,3(cis)propenoic acid;

(2E)-3-{4-[7-Dimethylamino)-1-methyl-2,3-dihydro-1H-indol-5-yl]-4,5,6,7-tetrahydro-1-benzofuran-2-yl}prop-2-enoic acid;

(2E)-3-[4-butyl-4-(5,5,8,8-tetramethyl-5,6,7,8-tetrahydronaphthalen-2-yl)-4,5,6,7-tetrahydro-1-benzofuran-2-yl]prop-2-enoic acid; and salts, solvates, or pharmaceutically functional derivatives thereof.

The present invention also includes compounds of formula II:

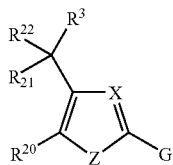

Formula II including salts, solvates, and pharmaceutically functional derivatives thereof, wherein X is $CR^1$ or N, where $R^1$ is halogen, H, or $CH_3$; Z is O, S, or NH; G is $CO_2R^7$, $SO_3R^7$, $PO_3R^7$, CONHOH, or

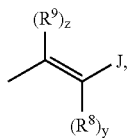

where the broken line represents an optional double bond; J is CHO, $CO_2R^7$, $SO_3R^7$, $PO_3R^7$, CONHOH, or J forms a thiazolidinedione ring with $R^8$; $R^7$ is H or $C_{1-5}$ alkyl; $R^8$ and $R^9$ are independently H, halogen, $C_{1-3}$ alkyl, or $CF_3$; y and z are each 0, 1, or 2; $R^3$ is

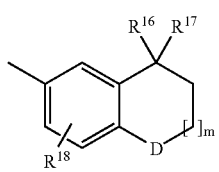

wherein D is $CR^{13}R^{14}$, O, S, $NR^{15}$, CHOH, CO, SO, $SO_2$, where $R^{13}$ and $R^{14}$ are independently H, $C_{1-3}$ alkyl, or cycloalkyl; and where $R^{15}$ is H, $C_{1-4}$ alkyl, or cycloalkyl; $R^{16}$ and $R^{17}$ independently are H, $C_{1-4}$ alkyl, cycloalkyl, or together form a carbocyclic ring having from 3 to 7 atoms; $R^{18}$ is H, $OR^6$, halogen, $CF_3$, alkenyl, $SR^{16}$, $C_{1-4}$ alkyl, $CO_2R^{16}$, $COR^{11}$, or $NR^{16}R^{17}$, where $R^{16}$ and $R^{17}$ are as above defined; m is 0 or 1; $R^{11}$ is $C_{1-5}$ alkyl, or cycloalkyl; or $R^3$ is

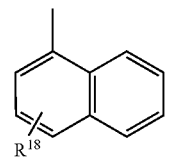

where $R^{18}$ is as defined above; or $R^3$ is

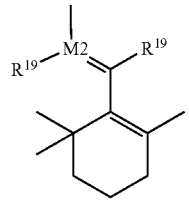

where M2 is C or N, provided however that the optional double bond represented by the broken line is optionally present only when M2 is C; $R^{19}$ is H or $C_{1-4}$ alkyl; or $R^3$ is

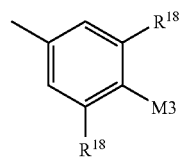

where $R^{18}$ is as defined above; and M3 is C—$(R^{16})_3$ or N—$(R^{16})_2$, when M3 is N—$(R^{16})_2$, an $R^{16}$ may combine with an $R^{18}$ to form a 5- or 6-membered ring; $R^{20}$ is H or $C_{1-4}$ alkyl; $R^{21}$ is H, $OR^6$, where $R^6$ is as defined for Formula I, or may combine with $R^{22}$ to form a carbonyl; and $R^{22}$ is H, or may combine with $R^{21}$ to form a carbonyl.

Preferably, X is C, $R^1$ is H, Z is O, $R^{20}$ is —$CH_3$, $R^{21}$ and $R^{22}$ are each H, G is

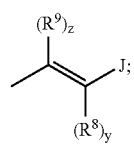

J is $CO_2H$, $R^8$ and $R^9$ are each H, y and z are each 1, the double bond exists, and the olefin geometry is trans.

In one embodiment preferably $R^3$ is

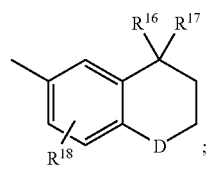

where D is $CR^{13}R^{14}$; $R^{13}$, $R^{14}$, $R^{16}$, and $R^{17}$ are each methyl; and $R^{18}$ is H.

Particularly preferred compounds of formula II include:
(2E)-3-{4-[(5,5,8,8-Tetramethyl-5,6,7,8-tetrahydro-2-naphthalenyl)methyl]-2-furyl}-2-propenoic acid;
(2E)-3-{4-[(5,5,8,8-Tetramethyl-5,6,7,8-tetrahydro-2-naphthalenyl)methyl]-2-thienyl}-2-propenoic acid;
(2E)-3-{4-[(3-Methoxy-5,5,8,8-tetramethyl-5,6,7,8-tetrahydro-2-naphthalenyl)methyl]-2-furyl}-2-propenoic acid;
(2E)-3-{5-Methyl-4-[(5,5,8,8-tetramethyl-5,6,7,8-tetrahydro-2-naphthalenyl)methyl]-2-furyl}-2-propenoic acid; and salts, solvates, or pharmaceutically functional derivatives thereof.

Another aspect of the present invention includes pharmaceutical compositions that include compounds of formula I or II along with one or more of a pharmaceutically acceptable carrier.

Another aspect of the present invention includes methods for treating, including treatment and prophylaxis, a disorder in a mammal, wherein the disorder is characterized by the need for retinoid therapym through the administration to the mammal an effective amount of a compound of formula I or II. Particular disorders characterized by the need for retinoid therapy and therefore included herein, but without exclusion, include metabolic conditions and disorders, dermatological conditions, cancerous and pre-cancerous conditions, hyperthyroidism, dyslipidemia, and hypertension. Preferably the disorder is diabetes or obesity.

Another aspect of the present invention includes compounds of formulas I or II for use as an active therapeutic substance. Preferably such use is for retinoid therapy.

Another aspect of the present invention includes compounds of formula I or II for use in the treatment or prophylaxis of diabetes or obesity.

Another aspect of the present invention includes the use of a compound of formulas I or II in the manufacture of a medicament for use in retinoid therapy, preferably for use in the treatment or prophylaxis of diabetes or obesity.

Another aspect of the present invention includes compounds of formulas I or II substantially as herein described with reference to any of the Examples.

Another aspect of the present invention includes a method for manufacturing a retinoid comprising:
 a) reacting a compound of Formula III, Formula IV, a combination of Formulas III and IV, or Formula XVII, with one of a compound of Formulas V, VI, or VII:

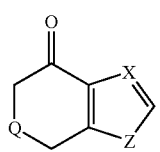

Formula III

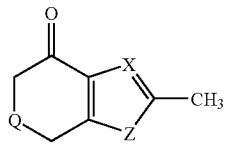

Formula IV

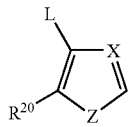

Formula XVII

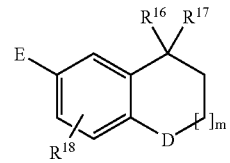

Formula V

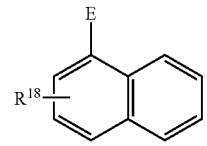

Formula VI

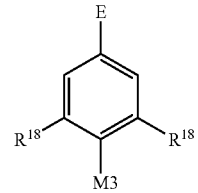

Formula VII wherein, X is $CR^1$ or N, where $R^1$ is halogen, H, or $CH_3$; Z is O, S, or NH; Q is $CR^4$, $CR^4R^5$, O, $NR^{10}$, or S, where $R^4$ and $R^5$ are independently H or $C_{1-5}$ alkyl, provided that when Q is $CR^4$, the A ring is aromatic; $R^{10}$ is $C_{1-6}$ alkyl, $COR^{11}$, $CONHR^{11}$, $CO_2R^{11}$, $CONR^{11}R^{12}$, $SO_2R^{11}$, aryl, or cycloalkyl; $R^{11}$ and $R^{12}$ are independently $C_{1-5}$ alkyl or cycloalkyl; E is Br or I; D is $CR^{13}R^{14}$, O, S, $NR^{15}$, CHOH, CO, SO, $SO_2$, where $R^{13}$ and $R^{14}$ are independently H, $C_{1-3}$ alkyl, or cycloalkyl; and where $R^{15}$ is H, $C_{1-4}$ alkyl, or cycloalkyl; $R^{16}$ and $R^{17}$ independently are H, $C_{1-4}$ alkyl, cycloalkyl, or together form a carbocyclic ring having from 3 to 7 atoms; $R^{18}$ is H, $OR^6$, halogen, $CF_3$, alkenyl, $SR^{16}$, $C_{1-4}$ alkyl, $CO_2R^{16}$, $COR^{11}$, or $NR^{16}R^{17}$, where $R^{16}$ and $R^{17}$ are as above defined; $R^{19}$ is H or alkyl; m is 0 or 1; and M3 is $C-(R^{16})_3$ or $N-(R^{16})_2$, when M3 is $N-(R^{16})_2$, an $R^{16}$ may combine with an $R^{18}$ to form a 5- or 6-membered ring;

b) generating an organometallic species from the product of step (a) via Grignard or metal halogen exchange reaction;
 c) condensing the organometallic species produced in step (b);
 d) reducing or oxidizing the condensed product produced in step (c);
 e) deprotonating the product of step (d) via organolithiums;
 f) formylating the deprotonated product produced in step (e); and
 g) treating the formylated product with a stabilized Wittig reagent and subsequent aqueous basic hydrolysis, to form a compound having activity for a retinoid receptor.

BRIEF DESCRIPTION OF THE PREFERRED EMBODIMENT

The term "alkyl" represents a straight or branched alkyl group, preferably having the specified number of carbon atoms. Typical alkyl groups include, but are not limited to methyl, ethyl, propyl, butyl, isopropyl, isobutyl, sec-butyl, tert-butyl, isopentyl, and the like.

The term "alkenyl" represents an olefinically unsaturated branched or straight group having the specified number of carbon atoms and at least one double bond. Examples of such groups include, but are not limited to vinyl, 1-propenyl, allyl, 1-butenyl, hexenyl, and the like.

The term "cycloalkyl" represents a saturated carbon chain forming a ring and includes, but should not be limited to cyclopropyl, cyclobutyl, cyclopentyl, and the like.

The term "carbocyclic" represents a homocyclic carbon ring system, for example, a benzene ring or naphthalene ring.

The term "aryl" represents cyclic aromatic groups that may include one or more heteroatoms, such as, without limitation, phenyl, pyridyl, furanyl, and the like.

The term "halogen" includes fluorine, chlorine, bromine, or iodine.

The term "carbonyl" refers to the group —C(O)—. In the case of the present invention where $R^{21}$ and $R^{22}$ combine to form a carbonyl the following example compounds are referred to:

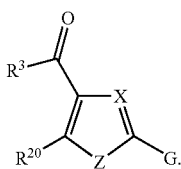

The term "thiazolidinedione," with reference to when J combines with $R^8$ refers to the following:

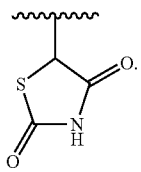

Some of the compounds of the present invention may contain one or more chiral centers and therefore may exist in enantiomeric and diastereomeric forms. Although particularly preferred compounds of the present invention include a defined stereochemistry, the scope of the present invention is intended to cover all isomers per se, as well as mixtures of cis and trans isomers, mixtures of diastereomers, and racemic mixtures of enantiomers as well.

When referred to herein, compounds of the present invention include compounds within the scope of both formula (I) and formula (II) as defined above unless specifically limited by the definition of each formula or specifically limited otherwise. The preferred embodiments of the present invention described herein, including uses and compositions, when applicable, apply to both formula (I) and formula (II).

As noted above, the present invention includes salts, solvates, and physiologically functional derivatives of the compounds of the present invention. Salts include addition salts, metal salts, or optionally alkylated ammonium salts, such as hydrochloric, hydrobromic, hydroiodic, phosphoric, sulfuric, trifluoroacetic, trichloroacetic, oxalic, maleic, pyruvic, malonic, succinic, citric, mandelic, benzoic, cinnamic, methane sulphonic, ethane sulphonic, picric and the like. Salts also include acids related to the salts listed within Journal of Pharmaceutical Science 1997, 66, 2, incorporated herein by reference as relevant to salts. Further acceptable salts include lithium, sodium, potassium, magnesium, and the like.

As used herein, the term "solvate" refers to a complex of variable stoichiometry formed by a solute (in this invention, a compound of formula I or II, or a salt or physiologically functional derivative thereof) and a solvent. Such solvents, for the purpose of the invention, should not interfere with the biological activity of the solute. Non-limiting examples of suitable solvents include, but are not limited to water, methanol, ethanol, and acetic acid. Preferably the solvent used is a pharmaceutically acceptable solvent. Non-limiting examples of suitable pharmaceutically acceptable solvents include water, ethanol, and acetic acid. Most preferably the solvent used is water.

As used herein, the term "physiologically functional derivative" refers to any pharmaceutically acceptable derivative of a compound of the present invention; for example, an ester or an amide, which upon administration to a mammal is capable of providing (directly or indirectly) a compound of the present invention or an active metabolite thereof. Such derivatives will be clear to those skilled in the art, without undue experimentation, and with reference to the teaching of Burger's Medicinal Chemistry And Drug Discovery, $5^{th}$ Edition, Vol 1: Principles and Practice, which is incorporated herein by reference to the extent that it teaches physiologically functional derivatives.

As used herein, the term "effective amount" means that amount of a drug or pharmaceutical agent that will elicit the biological or medical response of a tissue, system, animal, or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function. A therapeutically effective amount of a compound of the present invention will depend upon a number of factors including, for example, the age and weight of the animal, the precise condition requiring treatment and its severity, the nature of the formulation, and the route of administration. Therapeutic effectiveness ultimately will be at the discretion of the attendant physician or veterinarian. Generally, however, an effective amount of a compound of formula (I) or (II) for RXR mediated diseases and conditions should be in the range of about 0.1 to about 100 mg/kg body weight of recipient (mammal, preferably human) per day. Preferably the effective amount will be in the range of 0.5 to 10 mg/kg body weight per day. More preferably in the range of about 1 to 5 mg/kg body weight per day. An effective amount of a salt or solvate, or physiologically functional derivative thereof, may be determined as a proportion of the effective amount of the compound of formula (I) or (II) per se.

As noted earlier, RXR selective ligands are believed useful for a variety of diseases and conditions, including but not limited to treatments for metabolic conditions and disorders, dermatological conditions such as acne and psoriasis, the treatment and prevention of a variety of cancerous and pre-cancerous conditions such as acute promyleocytic leukemia, cutaneous T-cell lymphoma, epithelial cancers, squamous cell carcinoma, and breast cancer, as well as in the treatment of hyperthyroidism, dyslipidemia, and hypertension.

While it is possible that compounds of the present invention may be therapeutically administered as the raw chemical, it is preferable to present the active ingredient as a pharmaceutical formulation. Accordingly, the scope of the present invention further includes pharmaceutical formulations including compounds of Formula I or Formula II, or pharmaceutically acceptable salts or solvates thereof, with one or more pharmaceutically acceptable carrier. Optionally, other therapeutic and/or prophylactic ingredients may be included in any pharmaceutical formulation.

Formulations of the present invention include those especially formulated for oral, buccal, parental, transdermal, inhalation, intranasal, transmucosal, implant, or rectal administration. Among the variety of administrations, oral administration typically is preferred. For buccal administration, the formulation may take the form of tablets or lozenges formulated in conventional manner. For oral administration tablets, capsules, and caplets may contain conventional excipients such as binding agents, fillers, lubricants, disintegrants, and/or wetting agents. Non-limiting examples of binding agents include syrup, acacia, gelatin, sorbitol, tragacanth, mucilage of starch, or polyvinylpyrrolidone. Non-limiting examples of fillers include, for example, lactose, sugar, microcrystalline cellulose, maize-starch, calcium phosphate or sorbitol. Non-limiting examples of lubricants include, for example, magnesium sterate, stearic acid, talc, polyethylene glycol or silica. Non-limiting examples of disintegrants include, for example, potato starch or sodium starch glycollate. A non-limiting example of a wetting agent includes sodium lauryl sulfate. The tablets additionally may be coated according to methods known in the art.

Alternatively, the compounds of the present invention may be incorporated into oral liquid preparations such as aqueous or oily suspensions, solutions, emulsions, syrups, or elixirs. Moreover, formulations containing these compounds may be presented as a dry product for constitution with water or other suitable vehicle before use. Liquid preparations may contain conventional additives. Non-limiting examples of such additives include suspending agents such as sorbitol syrup, methyl cellulose, glucose/sugar syrup, gelatin, hydroxyethylcellulose, carboxymethyl cellulose, aluminum sterate gel or hydrogenated edible fats. Additionally, emulsifying agents such as lecithin, sorbitan monooleate or acacia; non-aqueous vehicles (which may include edible oils) such as almond oil, fractionated coconut oil, oily esters, propylene glycol or ethyl alcohol my be included. Further, preservatives such as methyl or propyl p-hydroxybenzoates or sorbic acid, may be incorporated into the preparation. Such preparations may also be formulated as suppositories, for example, containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle, for example, sterile, pyrogen-free water, before use.

The formulations according to the invention may also be formulated as a depot preparation. Such long acting formulations may be administered by implantation, for example, subcutaneously or intramuscularly, or by intramuscular injection. Accordingly, the compounds of the invention may be formulated with suitable polymeric or hydrophobic materials, such as an emulsion in an acceptable oil, ion exchange resins, or as sparingly soluble derivatives, such as a sparingly soluble salt.

The formulations according to the invention may contain between about 0.1–about 99% of the active ingredient.

Pharmaceutical formulations may be presented in unit dose forms containing a predetermined amount of active ingredient per unit dose. Such a unit may contain certain amounts of a compound of formula (I) depending on the condition being treated, the route of administration and the age, weight and condition of the patient. Preferred unit dosage formulations are those containing a daily dose, or an appropriate fraction thereof, of an active ingredient. Such pharmaceutical formulations may be prepared by any of the methods well known in the pharmacy art.

General Synthetic Scheme

In accordance with the present invention, compounds of Formula I can be prepared by reacting a compound of Formula III and/or Formula IV, with compounds of Formulas V, VI or VII, depending upon the desired value for $R^3$, as is shown below:

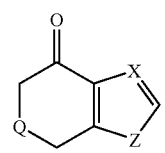

Formula III

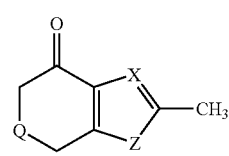

Formula IV wherein, as is relevant throughout this description, X, Z, and Q have the meanings as defined above for formula I;

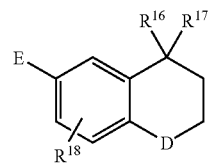

Formula V

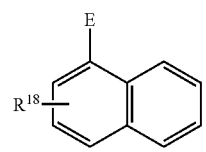

Formula VI

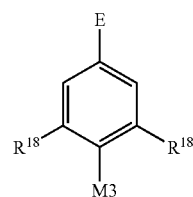

Formula VII wherein E represents either bromine, preferably, or iodine and, as is relevant throughout this description, wherein D, M3, $R^{16}$, $R^{17}$, and $R^{18}$ are defined as above for formula I.

Condensation of the organometallic species, generated via Grignard or metal halogen exchange reaction, with formula III or formula IV produces the hydroxy compounds of formula VIII, XI or X, below:

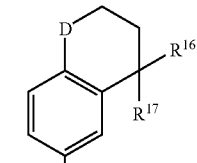

Formula VIII

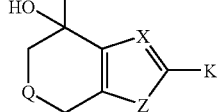

Formula XI

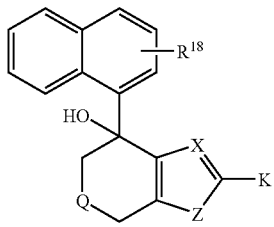

Formula X

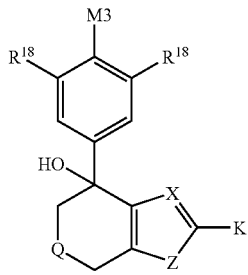

wherein K is H or CH$_3$. Reducing conditions (preferably NaBH$_4$, BF$_3$.Et$_2$O or Et$_3$SiH, TFA) generates the reduced compounds of formula XI, XII or XIII, shown below:

Formula XI

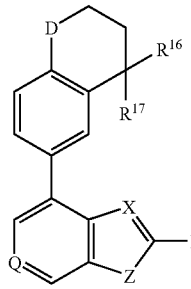

Formula XII

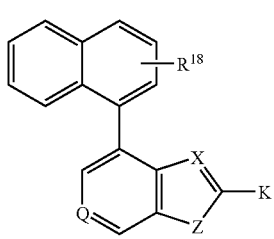

Formula XIII

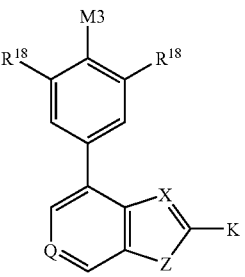

Or alternatively, oxidizing conditions (preferably DDQ, dioxane, 100° C.) produces the compounds of Formula XI, XII and XIII whereby the A ring, as is defined in formula I, becomes aromatic. Deprotonation via organolithiums, (preferably with n-butyl lithium) followed by formylation, preferably with N,N-dimethylformamide, generates compounds of formula XIV, XV or XVI illustrated below:

Formula XIV

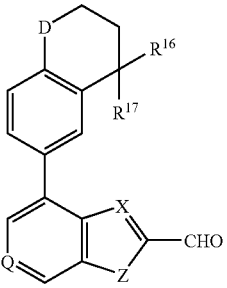

Formula XV

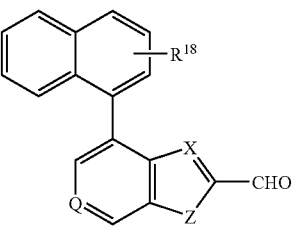

Formula XVI

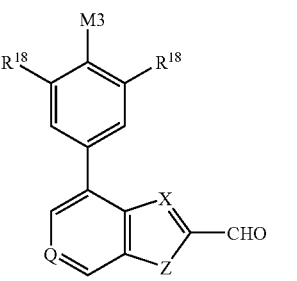

Treatment of these compounds with a stabilized Wittig reagent, preferably triethylphosphonoacetate, followed by aqueous basic hydrolysis affords compounds of formula I.

Alternatively, when K is methyl, treatment of the compound of formula XI under brominating conditions (preferably NBS, AIBN, CCl$_4$) followed by SN$^2$ displacement, preferably with potassium acetate, generates the acetoxy compound. Basic hydrolysis (preferably K$_2$CO$_3$, H$_2$O, MeOH) and oxidation (preferably TPAP, NMO, CH$_3$CN)

generates compounds of formula XIV that can then be converted to compounds of formula I as outlined above.

Compounds of formula II can be prepared by reacting a compound of Formula XVII, wherein X, Z, and $R^{20}$ are defined as before, with compounds of Formula V, VI or VII, shown above, where E is as hereinabove defined.

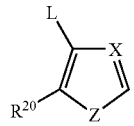

Formula XVII where L is CHO; CONMeOMe. Condensation of the appropriate organometallic species, generated via the Grignard or metal halogen exchange reaction, with formula XVII produces the hydroxy compound of formula XVIII or the ketone of formula XIX, each of which is shown below, where $R^3$ is as defined above and is determined through respective choice of Formulas V, VI, and VII:

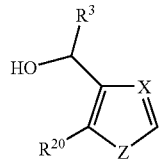

Formula XVIII

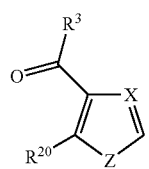

Formula XIX

Subsequent reduction (preferably $NaBH_4$, $BF_3.Et_2O$ or $Et_3SiH$, TFA) followed by deprotonation via organometallics, preferably n-butyl lithium, and formylation, preferably N,N-dimethylformamide, generates compounds of formula XX.

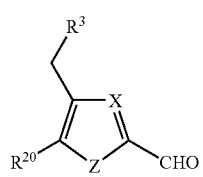

Formula XX

Treatment of these compounds with a stabilized Wittig reagent (preferably triethylphosphonoacetate) followed by basic aqueous hydrolysis affords compounds of formula II.

Regarding compounds where $R^3$ is

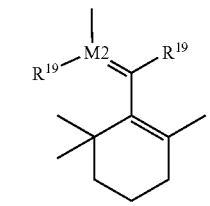

Examples 9 and 12, below, particularly demonstrate their manufacture. For example, Example 9:

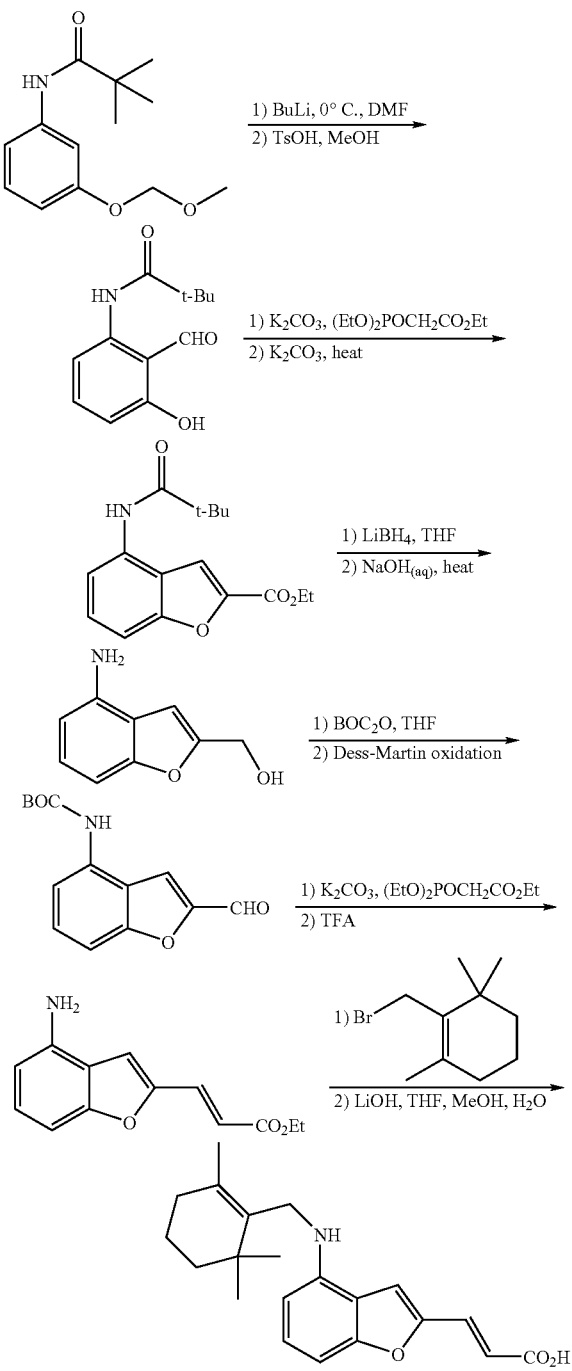

or Example 12:

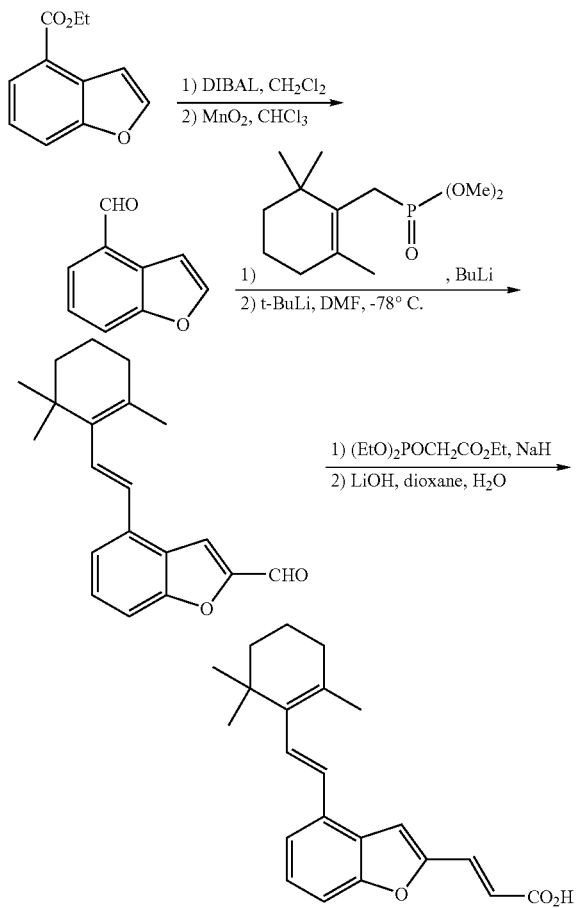

The following examples more particularly demonstrate the method of the present invention.

EXAMPLES

The following examples illustrate this invention, but should not be construed as limitations. The abbreviations, symbols, and conventions used in these examples are consistent with those used in the contemporary chemical literature, for example, the Journal of the American Chemical Society, such as:

THF: tetrahydrofuran
Rt: room temperature
Hr: hours
DMF: N,N-dimethylformamide
TPAP: tetrapropylammonium peruthenate
Et$_2$O: diethyl ether
DDQ: dichlorodicyanohydroquinone
MeOH: methanol
CCl$_4$: carbon tetrachloride
AIBN: azobisisobutyronitrile
NMO: N-methylmorpholine N-oxide
n-BuLi: n-butyl lithium
CDCl$_3$: deuterated chloroform
Min: minutes
DME: dimethoxyethane
EtOAc: ethyl acetate
NaOH: sodium hydroxide -continued MgSO$_4$: magnesium sulfate
CH$_2$Cl$_2$: dichloromethane
CH$_3$CN: acetonitrile
NBS: N-bromosuccinimide
HCl: hydrochloric acid
K$_2$CO$_3$: potassium carbonate
EtOAc: ethyl acetate Example 1

(2E)-3[4-(5,5,8,8-Tetramethyl-5,6,7,8-tetrahydro-2-naphthalenyl)-4,5,6,7-tetrahydro-1-benzofuran-2-yl]-2-propenoic acid A. 4-(5,5,8,8-Tetramethyl-5,6,7,8-tetrahydro-2-naphthalenyl)-4,5,6,7-tetrahydro-1-benzofuran-4-ol To a THF solution (200 mL) containing 6-bromo-1,1,4,4-tetramethyl-1,2,3,4-tetrahydronaphthalene (43.2 g, 161.8 mmol) cooled to −78° C. was added 68.0 mL of a 2.5 M hexanes solution of n-BuLi (170.0 mmol). The resulting reddish-orange solution stirred for 30 min when 6,7-dihydro-4(5H)-benzofuranone (20.0 g, 147.0 mmol) in 100 mL of THF was added. After stirring for 45 min the reaction was quenched with H$_2$O. Upon warming the solution was poured into additional H$_2$O and the organics were extracted with Et$_2$O. After drying over MgSO$_4$ the solvent was removed in vacuo and the residual oil purified via column chromatography (hexanes/EtOAc (7:1)) yielding 40.9 g (126.2 mmol, 86% yield) of compound A as white solid m.p. 55–57° C.
$^1$H NMR (CDCl$_3$) 400 MHz δ 7.29 (d, 1H, J=2.0 Hz), 7.25 (d, 1H, J=1.6 Hz), 7.19 (d, 1H, J=8.2 Hz), 7.07 (dd, 1H, J=8.3 & 2.1 Hz), 6.15 (d, 1H, J=1.8 Hz), 2.71–2.62 (m, 2H), 2.05–2.00 (m, 3H), 1.92–1.78 (m, 2H), 1.63 (s, 4H), 1.26 (s, 6H), 1.23 (s, 3H), 1.20 (s, 3H) ppm.

B. 4-(5,5,8,8-Tetramethyl-5,6,7,8-tetrahydro-2-naphthalenyl)-4,5,6,7-tetrahydro-1-benzofuran To a THF solution (100 mL) containing sodium borohydride (12.2 g, 324 mmol) cooled to 0° C. was added BF$_3$.Et$_2$O (69.0 g, 486 mmol). The resulting white slurry stirred for 10 min when compound A (described above) (10.5 g, 32.4 mmol) in 200 mL of THF was added. After 10 min the reaction mixture was very carefully poured into sat. NaHCO$_3$. The solution was then poured into additional sat. NaHCO$_3$ and the organics were extracted with Et$_2$O. After drying over MgSO$_4$ the solvent was removed in vacuo and the residual oil was purified via column chromatography (hexanes/EtOAc (19:1)) yielding 8.18 g (26.6 mmol, 82% yield) of compound B.
$^1$H NMR (CDCl$_3$) 400 MHz δ 7.26 (s, 1H), 7.19 (d, 1H, J=8.3 Hz), 7.07 (d, 1H, J=1.9 Hz), 6.89 (dd, 1H, J=8.1 & 1.8 Hz), 6.06 (d, 1H, J=1.6 Hz), 3.81 (m, 1H), 2.69–2.66 (m, 2H), 2.08 (m, 1H), 1.96–1.91 (m, 1H), 1.80–1.76 (m, 1H), 1.69–1.64 (m, 5H), 1.30 (s, 6H), 1.27 (s, 3H), 1.23 (s, 3H) ppm.

C. [4-(5,5,8,8-Tetramethyl-5,6,7,8-tetrahydro-2-naphthalenyl)-4,5,6,7-tetrahydro-1-benzofuran]-2-carboxaldehyde To a THF solution (380 mL) containing compound B (30.4 g, 98.7 mmol) cooled to 0° C. was added 41.4 mL of a 2.5 M hexanes solution of n-BuLi (103.6 mmol). The yellow-orange solution stirred for 15 min at which time DMF (10.8 g, 148.0 mmol) was added at which point the solution turned nearly colorless. After 10 min the reaction was quenched with sat. NaHSO$_4$, poured into additional sat. NaHSO$_4$ and the organics extracted with Et$_2$O. After drying over MgSO$_4$ the solvent was removed in vacuo and the residual yellow oil purified via column chromatography (hexanes/EtOAc (9:1)) affording 29.3 g (87.2 mmol, 88% yield) of compound C as a white solid m.p. 91–94° C.

$^1$H NMR (CDCl$_3$) 400 MHz δ 9.45 (s, 1H), 7.22 (d, 1H, J=8.1 Hz), 7.05 (d, 1H, J=1.8 Hz), 6.91 (s, 1H), 6.85 (dd, 1H, J=8.2 & 2.0 Hz), 3.84 (m, 1H), 2.80–2.78 (m, 2H), 2.17–2.11 (m, 1H), 2.10–2.01 (m, 1H), 1.88–1.82 (m, 1H), 1.75–1.66 (m, 5H), 1.31 (s, 6H), 1.26 (s, 3H), 1.23 (s, 3H) ppm.

D. Ethyl (2E)-3-[4-(5,5,8,8-Tetramethyl-5,6,7,8-tetrahydro-2-naphthalenyl)-4,5,6,7-tetrahydro-1-benzofuran-2-yl]-2-propenoate To a DME solution (300 mL) containing sodium hydride (5.23 g, 130.8 mmol, 60% dispersion in mineral oil) was added tiethylphosphonoacetate (29.3 g, 130.8 mmol) at room temperature. To the resulting solution was added compound C (29.3 g, 87.2 mmol) in 100 mL of DME. The reaction stirred for 20 min at which time it was quenched with H$_2$O. The solution was diluted with Et$_2$O and the organic layer separated. The aqueous layer was extracted with Et$_2$O and then the combined organic layers were dried over MgSO$_4$. Removal of the solvent in vacuo and purification via column chromatography (hexanes/EtOAc (9:1)) yielded 32.3 g (80.7 mmol, 92% yield) of compound D as a light yellow foam m.p. 47–49° C.

$^1$H NMR (CDCl$_3$) 400 MHz δ 7.32 (d, 1H, J=15.6 Hz), 7.20 (d, 1H, J=8.3 Hz), 7.05 (d, 1H, J=1.7 Hz), 6.86 (dd, 1H, J=8.0 & 1.9 Hz), 6.28 (s, 1H), 6.22 (d, 1H, J=15.6 Hz), 4.22 (q, 2H, J=7.2 Hz), 3.81–3.78 (m, 1H), 2.73–2.71 (m, 2H), 2.11–2.00 (m, 1H), 1.99–1.95 (m, 1H), 1.83–1.79 (m, 1H), 1.70–1.64 (m, 5H), 1.30 (t, 3H, J=7.1 Hz), 1.26 (s, 6H), 1.22 (s, 3H), 1.19 (s, 3H) ppm.

The enantiomers were separated utilizing supercritical fluid chromatography with a chiralpak-AS column eluting with CO$_2$/10% MeOH (containing 0.2% isopropylamine). The separated antipodes were taken directly into the ester hydrolysis step outlined below.

E. (2E)-3[4-(5,5,8,8-Tetramethyl-5,6,7,8-tetrahydro-2-naphthalenyl)-4,5,6,7-tetrahydro-1-benzofuran-2-yl]-2-propenoic acid To a dioxane solution (200 mL) containing compound D (30.5 g, 75.0 mmol) was added lithium hydroxide hydrate (31.5 g, 750 mmol) followed by 60 mL of H$_2$O. After stirring overnight TLC showed some starting material left so the solution was heated at 60° C. for 3 hr. The solution was acidified with sat. NaHSO$_4$, extracted with EtOAc and dried (MgSO$_4$). The organics were then heated with Darco and the solution filtered through a bed of celite with the celite being rinsed thoroughly with EtOAc. The solvent was removed in vacuo and the residual light yellow solid triturated with hexanes and collected via vacuum filtration yielding 24.5 g (64.8 mmol, 86% yield) of compound E as a light yellow solid m.p. 210–213° C. decomp.

$^1$H NMR (CDCl$_3$) 400 MHz δ 7.39 (d, 1H, J=15.4 Hz), 7.21 (d, 1H, J=8.0 Hz), 7.05 (d, 1H, J=1.6 Hz), 6.86 (dd, 1H, J=8.2 & 1.8 Hz), 6.35 (s, 1H), 6.21 (d, 1H, J=15.4 Hz), 3.82–3.79 (m, 1H), 2.74–2.72 (m, 2H), 2.12–2.07 (m, 1H), 2.00–1.98 (m, 1H), 1.81–1.70 (m, 1H), 1.67 (s(br), 5H), 1.26 (s, 6H), 1.22 (s, 3H), 1.19 (s, 3H) ppm.

The separated ethyl ester enantiomers (see above) were hydrolyzed using the aforementioned conditions yielding both the (+) and (−) enantiomers identical in all respects to racemic material, (+)-(2E)-3[4-(5,5,8,8-Tetramethyl-5,6,7,8-tetrahydro-2-naphthalenyl)tetrahydro-1-benzofuran-2-yl]-2-propenoic acid and (−)-(2E)-3[4-(5,5,8,8-Tetramethyl-5,6,7,8-tetrahydro-2-naphthalenyl)tetrahydro-1-benzofuran-2-yl]-2-propenoic acid.

Example 2

(2E)-3-[4-(3,5,5,8,8-pentamethyl-5,6,7,8-tetrahydro-2-naphthalenyl)-4,5,6,7-tetrahydro-1-benzofuran-2-yl]-2-propenoic acid

A. 4-(3,5,5,8,8-pentamethyl-5,6,7,8-tetrahydro-2-naphthalenyl)-4,5,6,7-tetrahydro-1-benzofuran-4-ol To a THF solution (15 mL) containing 6-bromo-1,1,4,4,7-pentamethyl-1,2,3,4-tetrahydronaphthalene (2.48 g, 8.82 mmol) cooled to −78° C. was added 3.88 mL of a 2.5 M hexanes solution of n-BuLi (9.70 mmol). After 10 min 6,7-dihydro-4(5H)-benzofuranone (1.0 g, 7.35 mmol) in 5 mL THF was added dropwise. The resulting amber solution stirred for 30 min at which time it was quenched with H$_2$O. Upon warming the solution was poured into H$_2$O and the organics were extracted with Et$_2$O. After drying over MgSO$_4$ the solvent was removed in vacuo and the residual oil purified via column chromatography (hexanes/EtOAc (9:1)) affording 1.32 g (3.91 mmol, 53% yield) of compound A as a white solid m.p. 122–124° C.

$^1$H NMR (CDCl$_3$) 400 MHz δ 7.42 (s, 1H), 7.27 (d, 1H, J=1.7 Hz), 7.00 (s, 1H), 6.15 (d, 1H, J=1.9 Hz), 2.73 (m, 1H), 2.63 (m, 1H), 2.11–1.96 (m, 4H), 1.85 (m, 1H), 1.66 (s, 4H), 1.25 (s, 6H), 1.22 (s, 6H) ppm.

B. 4-(3,5,5,8,8-pentamethyl-5,6,7,8-tetrahydro-2-naphthalenyl)-4,5,6,7-tetrahydro-1-benzofuran To a THF solution (10 mL) containing sodium borohydride (749 mg, 19.8 mmol) cooled to 0° C. was added BF$_3$.Et$_2$O (4.22 g, 29.7 mmol). The resulting white slurry stirred for 30 min at 0° C. when compound A (668 mg, 1.98 mmol) in 10 mL of THF was added. After 10 min the reaction mixture was carefully pored into sat. NaHCO$_3$. The 2-phase solution was then poured into additional sat. NaHCO$_3$ and the organics were extracted with Et$_2$O. After drying over MgSO$_4$ the solvent was removed in vacuo and the residual oil purified via column chromatography (hexanes/EtOAc (19:1)) yielding 383 mg (1.19 mmol, 60% yield) of compound B as a white solid m.p. 68–71° C.

$^1$H NMR (CDCl$_3$) 400 MHz δ 7.26 (d, 1H, J=1.5 Hz), 7.06 (s, 1H), 6.85 (s, 1H), 6.03 (d, 1H, J=1.9 Hz), 4.02 (m, 1H), 2.33 (s, 3H), 2.71–2.66 (m, 2H), 1.92 (m, 1H), 1.79 (m, 1H), 1.66–1.54 (m, 6H), 1.27 (s, 6H), 1.15 (s, 3H), 1.12 (s, 3H) ppm.

C. 4-(3,5,5,8,8-pentamethyl-5,6,7,8-tetrahydro-2-naphthalenyl)-4,5,6,7-tetrahydro-1-benzofuran-2-carbaldehyde To a Et$_2$O solution (10 mL) containing compound B (813 mg, 2.32 mmol) cooled to −40° C. was added 2.46 mL of a 1.7 M pentane solution of t-BuLi (4.18 mmol). The resulting solution stirred for 10 min at which time DMF (340 mg, 4.65 mmol) was added. Upon warming to −20° C. (~10 min) the reaction was quenched with $H_2O$. The solution was poured into additional $H_2O$ and the organics were extracted with $Et_2O$. After drying ($MgSO_4$) the solvent was removed in vacuo and the residual semi-solid purified via column chromatography (hexanes/EtOAc (9:1)) yielding 508 mg (1.45 mmol) of compound C as a white solid, m.p. 126–128° C. plus 209 mg (0.65 mmol) of unreacted B (87% yield based on unreacted starting material).

$^1$H NMR (CDCl$_3$) 400 MHz δ 9.46 (s, 1H), 7.08 (s, 1H), 6.89 (s, 1H), 6.78 (s, 1H), 4.06 (m, 1H), 2.83–2.79 (m, 2H), 2.33 (s, 3H), 2.12 (m, 1H), 2.06 (m, 1H), 1.86 (m, 1H), 1.67–1.61 (m, 5H), 1.28 (s(br), 6H), 1.15 (s, 3H), 1.11 (s, 3H) ppm.

D. Ethyl (2E)-3-[4-(3,5,5,8,8-pentamethyl-5,6,7,8-tetrahydro-2-naphthalenyl)-4,5,6,7-tetrahydro-1-benzofuran-2-yl]-2-propenoate.

To a DME solution (5 mL) containing sodium hydride (86 mg, 2.16 mmol, 60% dispersion in mineral oil) was added triethylphosphonoacetate (484 mg, 2.16 mmol). After 10 min compound C (504 mg, 1.44 mmol) in 5 mL DME was added. The reaction stirred for 10 min at which time it was quenched with $H_2O$. The solution was then poured into additional $H_2O$ and the organics were extracted with $Et_2O$. After drying over $MgSO_4$ the solvent was removed in vacuo and the residual oil purified via column chromatography (hexanes/EtOAc (19:1)) yielding 541 mg (1.29 mmol, 89% yield) of compound D as a clear oil which solidified on standing m.p. 59–61° C.

$^1$H NMR (CDCl$_3$) 400 MHz δ 7.32 (d, 1H, J=15.6 Hz), 7.06 (s, 1H), 7.00 (s, 1H), 6.82 (s, 1H), 6.24 (d, 1H, J=15.6 Hz), 4.22 (q, 2H, J=7.2 Hz), 4.02 (m, 1H), 2.77–2.71 (m, 2H), 2.32 (s, 3H), 2.08 (m, 1H), 1.98 (m, 1H), 1.81 (m, 1H), 1.66–1.55 (m, 5H), 1.31 (t, 3H, J=7.1 Hz), 1.27 (s, 6H), 1.15 (s, 3H), 1.11 (s, 3H) ppm.

E. (2E)-3-[4-(3,5,5,8,8-pentamethyl-5,6,7,8-tetrahydro-2-naphthalenyl)-4,5,6,7-tetrahydro-1-benzofuran-2-yl]-2-propenoic acid To a dioxane solution (9 mL) containing compound D (527 mg, 1.26 mmol) was added lithium hydroxide hydrate (264 mg, 6.28 mmol) followed by 3 mL of $H_2O$. The reaction stirred overnight and was them acidified with sat. $NaHSO_4$. The organics were extracted with EtOAc (2×), dried ($MgSO_4$) and the solvent removed in vacuo. The residual oil was purified via column chromatography ($CH_2Cl_2$/MeOH (15:1)) yielding 477 mg of a yellow foam which was triturated with hexanes and then collected via vacuum filtration affording 398 mg (1.02 mmol, 80% yield) of compound E as light yellow solid m.p. 220–225° C. decomp.

$^1$H NMR (CDCl$_3$) 400 MHz δ 7.40 (d, 1H, J=15.5 Hz), 7.07 (s, 1H), 6.82 (s, 1H), 6.31 (s, 1H), 6.23 (d, 1H, J=15.6 Hz), 4.00 (m, 1H), 2.77–2.74 (m, 2H), 2.32 (s, 3H), 2.08 (m, 1H), 1.98 (m, 1H), 1.81 (m, 1H), 1.66–1.56 (m, 5H), 1.27 (s, 6H), 1.15 (s, 3H), 1.11 (s, 3H) ppm.

Example 3

(2E)-3-[4-(3-methoxy-5,5,8,8-tetramethyl-5,6,7,8-tetrahydro-2-naphthalenyl)-4,5,6,7-tetrahydro-1-benzofuran-2-yl]-2-propenoic acid

A. 4-(3-methoxy-5,5,8,8-tetramethyl-5,6,7,8-tetrahydro-2-naphthalenyl)-4,5,6,7-tetrahydro-1-benzofuran-4-ol To a THF solution (80 mL) containing 6-bromo-7-methoxy-1,1,4,4-tetramethyl-1,2,3,4-tetrahydronaphthalene (10.0 g, 33.7 mmol) cooled to −78° C. was added 15.4 mL of a 2.4 M hexanes solution of n-BuLi (37.0 mmol). The resulting solution stirred for 30 min at which time 6,7-dihydro-4(5H)-benzofuranone (4.35 g, 32.0 mmol) in 20 mL of THF was added. After 30 min the reaction was quenched with $H_2O$. Upon warming the solution was poured into additional $H_2O$ and the organics were extracted with $Et_2O$. After drying over $MgSO_4$ the solvent was removed in vacuo and the residual yellow oil was purified via column chromatography (hexanes/EtOAc (9:1)) yielding 5.41 g (15.3 mmol, 48% yield) of compound A as a white solid m.p. 124–127° C.

$^1$H NMR (CDCl$_3$) 400 MHz δ 7.31 (d, 1H, J=1.8 Hz), 6.79 (s, 1H), 6.77 (s, 1H), 6.32 (d, 1H, J=1.9 Hz), 4.74 (s, 1H), 3.89 (s, 3H), 2.68–2.56 (m, 2H) 2.14–2.11 (m, 2H), 1.96 (m, 1H), 1.64–1.56 (m, 5H), 1.27 (s, 3H), 1.24 (s, 3H), 1.09 (s, 3H), 1.05 (s, 3H) ppm.

B. 4-(3-methoxy-5,5,8,8-tetramethyl-5,6,7,8-tetrahydro-2-naphthalenyl)-4,5,6,7-tetrahydro-1-benzofuran To a THF solution containing sodium borohydride (3.55 g, 93.8 mmol) cooled to 0° C. was added $BF_3 \cdot Et_2O$ (20.0 g, 140.7 mmol). The resulting white slurry stirred for 5 min when compound A (3.32 g, 9.38 mmol) in 60 mL of THF was added. The reaction stirred for 10 min at 0° C. when it was carefully poured into sat. $NaHCO_3$. This solution was then pored into $Et_2O$ and the organic layer separated. After drying over $MgSO_4$ the solvent was removed in vacuo and the residual oil purified via column chromatography (hexanes/EtOAc (19:1)) yielding 2.65 g (7.84 mmol, 84% yield) of compound B as a white solid m.p. 94–96° C.

$^1$H NMR (CDCl$_3$) 400 MHz δ 7.24 (d, 1H, J=1.5 Hz), 6.81 (s, 1H), 6.73 (s, 1H), 6.04 (d, 1H, J=1.5 Hz), 4.21 (m, 1H), 3.82 (s, 3H), 2.66–2.61 (m, 2H), 2.05 (m, 1H), 1.84–1.73 (m, 2H), 1.66–1.56 (m, 5H), 1.27 (s, 3H), 1.26 (s, 3H), 1.11 (s, 3H), 1.10 (s, 3H) ppm.

C. 4-(3-methoxy-5,5,8,8-tetramethyl-5,6,7,8-tetrahydro-2-naphthalenyl)-4,5,6,7-tetrahydro-1-benzofuran-2-carbaldehyde To a $Et_2O$ solution (20 mL) containing compound B (2.77g, 8.19 mmol) cooled to −40° C. was added 12.0 mL of a 1.7 M pentane solution of t-BuLi (20.5 mmol). The resulting yellow solution stirred for 30 min when DMF (1.50 g, 20.5 mmol) was added. The reaction slowly warmed to −20° C. over 20 min and was quenched with $H_2O$. The solution was poured into additional $H_2O$ and the organics extracted with $Et_2O$. After drying over $MgSO_4$ the solvent was removed in vacuo and the residual oil purified via column chromatography (hexanes/EtOAc (4:1)) yielding 1.64 g (4.48 mmol, 55% yield of compound C as a viscous oil which solidified on standing m.p. 58–60° C.

¹H NMR (CDCl₃) 400 MHz δ 9.45 (s, 1H), 6.92 (s, 1H), 6.78 (s, 2H), 4.27 (m, 1H), 3.83 (s, 3H), 2.80–2.76 (m, 2H), 2.08 (m, 1H), 1.96 (m, 1H), 1.85 (m, 1H), 1.74–1.61 (m, 5H), 1.26 (s, 6H), 1.14 (s, 3H), 1.12 (s, 3H) ppm.

D. Ethyl (2E)-3-[4-(3-methoxy-5,5,8,8-tetramethyl-5,6,7,8-tetrahydro-2-naphthalenyl)-4,5,6,7-tetrahydro-1-benzofuran-2-yl]-2-propenoate To a DME solution (10 mL) containing sodium hydride (269 mg, 6.72 mmol, 60% dispersion in mineral oil) was added triethylphosphonoacetate (1.51 g, 6.72 mmol). After 5 min compound C (1.64 g, 4.48 mmol) in 10 mL DME was added. After 15 min the reaction was quenched with H₂O and the organics were extracted with Et₂O. Upon drying over MgSO₄ the solvent was removed in vacuo and the residual oil purified via column chromatography (3% EtOAc/hexanes) affording 1.40 g (3.20 mmol, 71% yield) of compound D as an oil which solidified on standing m.p. 67–69° C.

¹H NMR (CDCl₃) 400 MHz δ 7.32 (d, 1H, J=15.5 Hz), 6.78 (s, 1H), 6.74 (s, 1H), 6.27 (s, 1H), 6.21 (d, 1H, J=15.6 Hz), 4.23–4.18 (m, 3H), 3.81 (s, 3H), 2.71–2.66 (m, 2H), 2.05 (m, 1H), 1.86 (m, 1H), 1.79–1.58 (m, 6H), 1.31–1.27 (m, 9H), 1.11 (s, 3H), 1.10 (s, 3H) ppm.

E. (2E)-3-[4-(3-methoxy-5,5,8,8-tetramethyl-5,6,7,8-tetrahydro-2-naphthalenyl)-4,5,6,7-tetrahydro-1-benzofuran-2-yl]-2-propenoic acid To a dioxane solution (10 mL) containing compound D (1.32 g, 3.04 mmol), was added 3 mL H₂O and lithium hydroxide hydrate (1.28 g, 30.4 mmol) at room temperature. After 2 days the reaction was acidified with sat. NaHSO₄ and the organics extracted with EtOAc. After drying over MgSO₄ the solvent was removed in vacuo and the residual yellow oil was purified via column chromatography (CH₂Cl₂/MeOH (15:1)) yielding 922 mg (2.26 mmol, 74% yield, recrystallized from hexanes) of compound E as a white solid m.p. 231–233° C.

¹H NMR (CDCl₃) 400 MHz δ 7.42 (d, 1H, J=15.3 Hz), 6.80 (s, 1H), 6.76 (s, 1H), 6.36 (s, 1H), 6.23 (d, 1H, J=15.6 Hz), 4.22 (m, 1H), 3.38 (s, 3H), 2.74–2.70 (m, 2H), 2.08 (m, 1H), 1.19 (m, 1H), 1.81 (m, 1H), 1.68–1.61 (m, 6H), 1.29 (s, 6H), 1.14 (s, 3H), 1.12 (s, 3H) ppm.

Example 4

(2E)-3-[4-(5,5,8,8-tetramethyl-3-propoxy-5,6,7,8-tetrahydro-2-naphthalenyl)-4,5,6,7-tetrahydro-1-benzofuran-2-yl]-2-propenoic acid

A. 4-(5,5,8,8-tetramethyl-3-propoxy-5,6,7,8-tetrahydro-2-naphthalenyl)-4,5,6,7-tetrahydro-1-benzofuran-4-ol To a THF solution (50 mL) containing 6-bromo-1,1,4,4-tetramethyl-7-propoxy-1,2,3,4-tetrahydronaphthalene (4.29 g, 13.2 mmol) cooled to −78° C. was added 5.3 mL of a 2.6 M heptane solution of n-BuLi (13.9 mmol). After 30 min 6,7-dihydro-4(5H)-benzofuranone (1.62 g, 11.9 mmol) in 12 mL of THF was added. The resulting solution stirred for 1 h and was then quenched with H₂O, poured into additional H₂O and the organics extracted with Et₂O. After drying over MgSO₄ the solvent was removed in vacuo and the residual oil purified via column chromatography (hexanes/EtOAc (6:1)) yielding 2.1 g (5.50 mmol, 46% yield) of compound A as a white solid m.p. 139–142° C.

¹H NMR (CDCl₃) δ 7.30 (d, 1H, J=1.7 Hz), 6.79 (s, 1H), 6.77 (s, 1H), 6.31 (d, 1H, J=1.9 Hz), 4.81 (s, 1H), 4.06–3.95 (m, 2H), 2.70–2.54 (m, 2H), 2.21–2.09 (m, 2H), 1.98 (m, 1H), 1.88–1.80 (m, 2H), 1.65–1.58 (m, 5H), 1.26 (s, 3H), 1.23 (s, 3H), 1.09 (s, 3H), 1.07–1.04 (m, 6H) ppm.

B. 4-(5,5,8,8-tetramethyl-3-propoxy-5,6,7,8-tetrahydro-2-naphthalenyl)-4,5,6,7-tetrahydro-1-benzofuran To a THF solution (20 mL) containing sodium borohydride (1.76 g, 46.7 mmol), cooled to 0° C. was added BF₃.Et2O (9.94 g, 70.0 mmol). To the resulting white slurry was added compound A (1.78 g, 4.67 mmol) in 25 mL THF. After 10 min the solution was carefully poured into sat. NaHCO₃. The two-phase solution was poured into additional sat. NaHCO₃ and the organics were extracted with Et₂O. After drying over MgSO₄ the solvent was removed in vacuo and the residual oil purified via column chromatography (5% EtOAc/hexanes) affording 1.56 g (4.26 mmol, 91% yield) of compound B as a clear oil.

¹H NMR (CDCl₃) 400 MHz δ 7.23 (d, 1H, J=1.5 Hz), 6.81 (s, 1H), 6.71 (s, 1H), 6.05 (d, 1H, J=1.7 Hz), 4.23 (m, 1H), 3.93–3.88 (m, 2H), 2.66–2.60 (m, 2H), 2.05 (m, 1H), 1.84–1.73 (m, 4H), 1.66–1.57 (m, 5H), 1.26 (s, 3H), 1.25 (s, 3H), 1.11 (s, 3H), 1.10 (s, 3H), 1.02 (t, 3H, J=7.4 Hz) ppm.

C. 4-(5,5,8,8-tetramethyl-3-propoxy-5,6,7,8-tetrahydro-2-naphthalenyl)-4,5,6,7-tetrahydro-1-benzofuran-2-carbaldehyde To a Et₂O solution (10 mL) containing compound B (1.41 g, 3.86 mmol) cooled to −30° C. was added 3.4 mL of a 1.7 M pentane solution of t-BuLi (5.79 mmol). After 30 min DMF (423 mg, 5.79 mmol) was added. The reaction slowly warmed and after an additional 30 min it was quenched with H₂O. The solution was then poured into additional H₂O and the organics extracted with Et₂O. After drying over MgSO₄ the solvent was removed in vacuo and the residual oil purified via column chromatography (hexanes/EtOAc (9:1)) yielding 1.13 g (2.86 mmol, 74% yield) of compound C as a clear oil.

¹H NMR (CDCl₃) 400 MHz δ 9.43 (s, 1H), 6.90 (s, 1H), 6.76 (s, 1H), 6.72 (s, 1H), 4.23 (m, 1H), 3.95–3.84 (m, 2H), 2.77–2.73 (m, 2H), 2.06 (m, 1H), 1.94 (m, 1H), 1.84–1.71 (m, 4H), 1.65–1.58 (m, 4H), 1.26 (s, 3H), 1.25 (s, 3H), 1.12 (s, 3H), 1.10 (s, 3H), 0.99 (t, 3H, J=7.4 Hz) ppm.

D. Ethyl (2E)-3-[4-(5,5,8,8-tetramethyl-3-propoxy-5,6,7,8-tetrahydro-2-naphthalenyl)-4,5,6,7-tetrahydro-1-benzofuran-2-yl]-2-propenoate To a DME solution (10 mL) containing sodium hydride (156 mg, 3.89 mmol, 60% dispersion in mineral oil) was added triethylphophonoacetate (872 mg, 3.89 mmol), followed by compound C (1.02 g, 2.59 mmol) in 10 mL DME. After 15 min the reaction was quenched with H₂O and the organics extracted with Et₂O. After drying over MgSO₄ the solvent was removed in vacuo and the residual oil purified via column chromatography (hexanes/EtOAc (19:1)) yielding 748 mg (1.61 mmol, 62% yield) of compound D as an oil which solidified on standing m.p. 52–54° C.

¹H NMR (CDCl₃) 400 MHz δ 7.31 (d, 1H, J=15.7 Hz), 6.78 (s, 1H), 6.71 (s, 1H), 6.28 (s, 1H), 6.20 (d, 1H, J=15.7 Hz), 4.23–4.17 (m, 3H), 3.93–3.85 (m, 2H), 2.70–2.66 (m, 2H), 2.03 (m, 1H), 1.88 (m, 1H), 1.79–1.69 (m, 2H), 1.68–1.57 (m, 6H), 1.28 (t, 3H, J=7.2 Hz), 1.26 (s, 3H), 1.25 (s, 3H), 1.11 (s, 3H), 1.10 (s, 3H), 1.01 (t, 3H, J=7.4 Hz) ppm.

E. (2E)-3-[4-(5,5,8,8-tetramethyl-3-propoxy-5,6,7,8-tetrahydro-2-naphthalenyl)-4,5,6,7-tetrahydro-1-benzofuran-2-yl]-2-propenoic acid To a dioxane solution (15 mL) containing compound D (1.02 g, 2.20 mmol) was added lithium hydroxide hydrate (924 mg, 22.0 mmol) followed by 5 mL of $H_2O$. The reaction stirred for 2 days at which time it was acidified with sat. $NaHSO_4$. The organics were extracted with EtOAc, dried ($MgSO_4$) and the solvent removed in vacuo. The residual material was purified via column chromatography ($CH_2Cl_2$/MeOH (15:1)) yielding 921 mg (2.11 mmol, 96% yield, recrystallized from hexanes) of compound E as a white solid, m.p. 195–196° C.

$^1$H NMR ($CDCl_3$) 400 MHz δ 7.42 (d, 1H, J=15.5 Hz), 6.81 (s, 1H), 6.74 (s, 1H), 6.37 (s, 1H), 6.22 (d, 1H, J=15.5 Hz), 4.23 (m, 1H), 3.95–3.89 (m, 2H), 2.74–2.70 (m, 2H), 2.08 (m, 1H), 1.92 (m, 1H), 1.83–1.69 (m, 2H), 1.67–1.60 (m, 6H), 1.28 (s, 3H), 1.14 (s, 3H), 1.12 (s, 3H), 1.03 (t, 3H, J=7.3 Hz) ppm.

Example 5

(2E)-3-[6-methyl-(5,5,8,8,-tetramethyl-5,6,7,8-tetrahydro-2-naphthalenyl)-4,5,6,7-tetrahydrofuro[2,3-c]pyridin-2-yl]-2-propenoic acid A. Ethyl 4-hydroxy-4-(5,5,8,8-tetramethyl-5,6,7,8-tetrahydro-2-naphthalenyl)-4,7-dihydrofuro[2,3-c]pyridine-6(5H)-carboxylate To a THF solution (40 mL) containing 6-bromo-1,1,4,4-tetramethyl-1,2,3,4-tetrahydronaphthalene (3.82 g, 14.3 mmol) cooled to –78° C. was added 6.0 mL of a 2.5 M hexanes solution of n-BuLi (15.0 mmol). After 30 min at –78° C. ethyl 4-oxo-4,7-dihydrofuro[2,3-c]pyridine-6(5H)-carboxylate (2.71 g, 13.0 mmol) in 40 mL of THF was added. The dark orange solution stirred for 1 h and was then quenched with $H_2O$. The solution was then poured into additional $H_2O$ and the organics extracted with EtOAc. After drying over $MgSO_4$ the solvent was removed in vacuo and the residual oil purified via column chromatography (hexanes/EtOAc (7:3)) yielding 2.56 g (6.45 mmol, 50% yield) of compound A as a waxy solid m.p. 56–57° C.

$^1$H NMR signals were very broad due to rotomers however GC-MS showed 1 peak.

B. Ethyl 4-(5,5,8,8-tetramethyl-5,6,7,8-tetrahydro-2-naphthalenyl)-4,7-dihydrofuro[2,3-c]pyridine-6(5H)-carboxylate To a THF solution (3 mL) containing sodium borohydride (297 mg, 7.86 mmol) was added $BF_3.Et_2O$ (1.67 g, 11.8 mmol) at room temperature. The resulting white slurry stirred for 5 min when compound A (323 mg, 0.79 mmol) in 4 mL THF was added. After stirring for 1 h at room temperature. the solution was poured into sat. $NaHCO_3$. The organics were extracted with $Et_2O$, dried ($MgSO_4$) and the solvent removed in vacuo. The residual foam was purified via column chromatography (hexanes/EtOAc (4:1)) yielding 149 mg (0.38 mmol, 48% yield) of compound B as a white solid, m.p. 92–94° C.

$^1$H NMR signals were very broad due to rotomers, however GC-MS showed a single peak El+m/z 382.

C. 6-Methyl-4-(5,5,8,8-tetramethyl-5,6,7,8-tetrahydro-2-naphthalenyl)-4,5,6,7tetrahydrofuro[2,3-c]pyridine To a THF solution (10 mL) containing compound B (528 mg, 1.39 mmol) was added 3.5 mL of a 1.0M $Et_2O$ solution of $LiAlH_4$ (3.5 mmol) at room temperature. The resulting solution was then heated to reflux for 30 min. Upon cooling to room temperature. the reaction was carefully quenched with 1 mL of 2.0 M NaOH. The heterogeneous solution then had $MgSO_4$ added to it and was diluted with $Et_2O$. The slurry was filtered through a bed of celite and rinsed thoroughly with $Et_2O$. The filtrate was washed with 2.0 M NaOH, dried ($MgSO_4$) and the solvent removed in vacuo. The residual oil was purified via column chromatography (hexanes/EtOAc (1:1)) yielding 353 mg (1.10 mmol, 79% yield) of compound C as a clear oil.

$^1$H NMR ($CDCl_3$) 400 MHz δ 7.25 (d, 1H, J=1.4 Hz), 7.18 (d, 1H, J=8.1 Hz), 7.09 (d, 1H, J=1.9 Hz), 6.90 (dd, 1H, J=8.1 & 1.9 Hz), 6.10 (d, 1H, J=1.8 Hz), 3.97 (m, 1H), 3.69 (d, 1H, J=14.4 Hz), 3.38 (dd, 1H, J=14.3 & 2.4 Hz), 2.99 (dd, 1H, J=11.6 & 5.1 Hz), 2.45(2, 3H), 2.34 (dd, 1H, J=11.6 & 9.2 Hz), 1.65 (s, 4H), 1.24–1.22 (m, 12H) ppm.

D. 6-Methyl-4-(5,5,8,8-tetramethyl-5,6,7,8-tetrahydro-2-naphthalenyl)-4,5,6,7tetrahydrofuro[2,3-c]pyridin-2-carbaldehyde To a $Et_2O$ solution (8 mL) containing compound C (350 mg, 1.08 mmol) cooled to –40° C. was added 1.9 mL of a 1.7 M pentane solution of t-BuLi (3.25 mmol). The yellow solution was allowed to warm to –30° C. where it was held, and after 30 min DMF (237 mg, 3.24 mmol) was added. The reaction slowly warmed and was quenched with $H_2O$ after 15 min. The orange solution was poured into additional $H_2O$ and the organics were extracted with $Et_2O$. After drying over $MgSO_4$ the solvent was removed in vacuo and the residual oil purified via column chromatography (EtOAc/hexanes (3:2)) yielding 194 mg (0.55 mmol, 51% yield) of compound D as an oil.

$^1$H NMR ($CDCl_3$) 400 MHz δ 9.47 (s, 1H), 7.20 (d, 1H, J=8.1 Hz), 7.07 (d, 1H, J=1.9 Hz), 6.94 (s, 1H), 6.86 (dd, 1H, J=8.0 & 1.9 Hz), 4.0 (m, 1H), 3.78 (d, 1H, J=16.1 Hz), 3.45 (dd, 1H, J=16.0 & 2.1 Hz), 3.03 (dd, 1H, J=12.0 & 5.3 Hz), 2.48 (s, 3H), 2.41 (dd, 1H, J=12.0 & 9.1 Hz), 1.67 (s, 3H), 1.26–1.18 (m, 12H) ppm.

E. Ethyl (2E)-3-[6-methyl-4-(5,5,8,8-tetramethyl-5,6,7,8-tetrahydro-2-naphthalenyl)-4,5,6,7-tetrahydrofuro[2,3-c]pyridin-2-yl]-2-propenoate To a DME solution (2 mL) containing sodium hydride (33 mg, 0.83 mmol, 60% dispersion in mineral oil) was added triethylphosphonoacetate (186 mg, 0.83 mmol) at room temperature. After 5 min compound D (194 mg, 0.55 mmol) in 2 mL DME was added. The reaction stirred for 20 min at which time it was quenched with $H_2O$. The solution was poured into additional $H_2O$ and the organics extracted with $Et_2O$. After drying over $MgSO_4$ the solvent was removed in vacuo and the residual oil purified via column chromatography (hexanes/EtOAc (3:2)) yielding 169 mg (0.30 mmol, 71% yield) of compound E as an oil.

$^1$H NMR ($CDCl_3$) 400 MHz δ 7.31 (d, 1H, J=15.5 Hz), 7.19 (d, 1H, J=8.1 Hz), 7.06 (d, 1H, J=1.7 Hz), 6.88 (dd, 1H,

J=8.2 & 1.7 Hz), 6.32 (s, 1H), 6.20 (d, 1H, J=15.7 Hz), 4.19 (q, 2H, J=7.1 Hz), 3.95 (m, 1H), 3.72 (d, 1H, J=15.6 Hz), 3.42 (dd, 1H, J=15.4 & 2.2 Hz), 2.99 (dd, 1H, J=11.8 & 5.3 Hz), 2.46 (s, 3H), 2.36 (dd, 1H, J=11.8 & 9.4 Hz), 1.64 (s, 4H), 1.28 (t, 3H, J=7.1 Hz), 1.24–1.21 (m, 12H) ppm.

F. (2E)-3-[6-methyl-4-(5,5,8,8,-tetramethyl-5,6,7,8-tetrahydro-2-naphthalenyl)-4,5,6,7-tetrahydrofuro[2,3-c]pyridin-2-yl]-2-propenoic acid To a dioxane solution (2 mL) containing compound E (169 mg, 0.39 mmol) was added lithium hydroxide hydrate (164 mg, 3.92 mmol) followed by 0.7 mL of $H_2O$. The reaction went for 24 h at room temperature. at which time 702 mg of $NaHSO_4$ was added along with $H_2O$ and EtOAc. After stirring for 10 min the solution was poured into additional $H_2O$ and the organics extracted with EtOAc. After drying over $MgSO_4$ the solvent was removed in vacuo and the residual material purified via column chromatography ($CH_2Cl_2$/MeOH (9:1)) affording 101 mg (0.26 mmol, 66% yield) of compound F as an off-white solid, m.p. 128–130° C. decomp.

$^1$H NMR ($CDCl_3$) 400 MHz δ 7.32 (d, 1H, J=15.7 Hz), 7.28 (d, 1H, J=8.1 Hz), 7.23 (d, 1H, J=1.5 Hz), 6.96 (dd, 1H, J=8.2 & 1.6 Hz), 6.22 (d, 1H, J=15.7 Hz), 4.46 (d, 1H, J=15.6 Hz), 4.36 (m, 1H), 4.30 (d, 1H, J=15.6 Hz), 3.63 (dd, 1H, J=12.2 & 5.4 Hz), 3.13 (t, 1H, J=11.7 Hz), 2.98 (s, 3H), 1.68 (s, 4H), 1.26–1.22 (m, 12H) ppm.

Example 6

(2E)-3-[4-(5,5,8,8-tetramethyl-5,6,7,8-tetrahydro-2-naphthalenyl)-1-benzofuran-2-yl]-2-propenoic acid

A. 4-(5,5,8,8-Tetramethyl-5,6,7,8-tetrahydro-2-naphthalenyl)-1-benzofuran

To a dioxane solution (25 mL) containing 4-(5,5,8,8-Tetramethyl-5,6,7,8-tetrahydro-2-naphthalenyl)-4,5,6,7-tetrahydro-1-benzofuran-4-ol (synthesized in example 1 part A) (985 mg, 3.04 mmol) was added DDQ (1.73 g, 7.60 mmol). The solution was then heated to 100° C. for 4 h at which time the dark solution was filtered through a bed of celite. The celite was rinsed thoroughly with $Et_2O$ followed by washing the filtrate with $H_2O$ (2×) and then drying over $MgSO_4$. The solvent was then removed in vacuo and the residual dark oil was purified via column chromatography (hexanes/2% EtOAc) yielding 430 mg (1.42 mmol, 47% yield) of compound A as a white solid after trituration with hot MeOH and filtration, m.p. 153–154° C.

$^1$H NMR ($CDCl_3$) 400 MHz δ 7.69 (d, 1H, J=2.2 Hz), 7.61 (d, 1H, J=1.1 Hz), 7.52–7.35 (m, 5H), 6.99 (d, 1H, J=2.1 Hz), 1.78 (s, 4H), 1.39 (s, 6H), 1.38 (s, 6H) ppm.

B. 4-(5,5,8,8-Tetramethyl-5,6,7,8-tetrahydro-2-naphthalenyl)-1-benzofuran-2-carbaldehyde A $Et_2O$ solution (20 mL) containing compound A (2.43 g, 7.99 mmol) cooled to −40° C. had 7.0 mL of a 1.7 M pentane solution of t-BuLi (11.9 mmol) added to it. The orange solution stirred for 30 min at which time DMF (876 mg, 12.0 mmol) was added. The reaction slowly warmed to 0° C. over 1 h and was then quenched with $H_2O$. The solution was poured into $H_2O$ and the organics extracted with $Et_2O$. After drying over $MgSO_4$ the solvent was removed in vacuo and the residual yellow solid was purified via column chromatography (3% hexanes/EtOAc) yielding 1.98 g (5.97 mmol, 75% yield) of compound B as a white solid m.p. 122–124° C.

$^1$H NMR ($CDCl_3$) 400 MHz δ 9.84 (s, 1H), 7.70 (s, 1H), 7.56–7.34 (m, 6H), 1.73 (s, 4H), 1.34 (s, 6H), 1.33 (s, 6H) ppm.

C. Ethyl (2E)-3-[4-(5,5,8,8-Tetramethyl-5,6,7,8-tetrahydro-2-naphthalenyl)-1-benzofuran-2-yl]-2-propenoate To a DME solution (10 mL) containing sodium hydride (358 mg, 8.96 mmol, 60% dispersion in mineral oil) was added triethylphosphonoacetate (2.01 g, 8.96 mmol) at room temperature. After 5 min compound B (1.98 g, 5.97 mmol) in 20 mL of DME was added. The resulting orange solution stirred for 30 min at which time it was quenched with $H_2O$. The solution was poured into additional $H_2O$ and the organics were extracted with $Et_2O$. After drying over $MgSO_4$ the solvent was removed in vacuo and the residual oil purified via column chromatography (hexanes/EtOAc 3%) yielding 2.12 g (5.28 mmol, 88% yield) of compound C as a white solid m.p. 119–121° C.

$^1$H NMR ($CDCl_3$) 400 MHz δ 7.54–7.51 (m, 2H), 7.41–7.33 (m, 4H), 7.29 (dd, 1H, J=6.6 & 1.8 Hz), 7.08 (s, 1H), 6.56 (d, 1H, J=15.7 Hz), 4.25 (q, 2H, J=7.1 Hz), 1.72 (s, 4H), 1.34–1.30 (m, 15H) ppm.

D. (2E)-3-[4-(5,5,8,8-tetramethyl-5,6,7,8-tetrahydro-2-naphthalenyl)-1-benzofuran-2-yl]-2-propenoic acid To a dioxane solution (2 mL) containing compound C (88 mg, 0.22 mmol) was added lithium hydroxide hydrate (46 mg, 1.09 mmol) and 0.5 mL of $H_2O$ at room temperature. After 2 days the solution was acidified with sat. $NaHSO_4$ and the organics were extracted with EtOAc. After drying over $MgSO_4$ the solvent was removed in vacuo and the residual liquid was purified via column chromatography ($CH_2Cl_2$/MeOH (15:1)) yielding 63 mg (0.17 mmol, 76% yield) of compound D as a white solid, m.p. 216–219° C. decomp.

$^1$H NMR ($CDCl_3$) 400 MHz δ 7.63 (d, 1H, J=15.5 Hz), 7.53 (d, 1H, J=1.5 Hz), 7.44–7.32 (m, 5H), 7.16 (s, 1H), 6.60 (d, 1H, J=15.6 Hz), 1.75 (s, 4H), 1.36 (s, 6H), 1.35 (s, 6H) ppm.

Example 7

(2E)-3-[4-(5,5,8,8-tetramethyl-5,6,7,8-tetrahydro-2-naphthalenyl)-4,5,6,7-tetrahydro-1-benzothien-2-yl]-2-propenoic acid

A. 4-(5,5,8,8-tetramethyl-5,6,7,8-tetrahydro-2-naphthalenyl)-4,5,6,7-tetrahydro-1-benzothiophen-4-ol To a THF solution (10 mL) containing 6-bromo-1,1,4,4-tetramethyl-1,2,3,4-tetrahydronaphthalene (1.04 g, 3.90 mmol) cooled to −78° C. was added 1.7 mL of a 2.4 M hexanes solution of n-BuLi (4.09 mmol). The solution stirred for 45 min when 6,7-dihydro-1-benzothiophen-4 (5H)-one (563 mg, 3.70 mmol) in 10 mL of THF was added. After 45 min at −78° C. the reaction was quenched with $H_2O$ and the organics extracted with $Et_2O$. After drying over $MgSO_4$ the solvent was removed in vacuo and the residual oil purified via column chromatography (hexanes/EtOAc (9:1)) yielding 564 mg (1.66 mmol, 45% yield) of compound A as an oil which solidified on standing m.p. 42–44° C.

¹H NMR (CDCl₃) 400 MHz δ 7.27 (d, 1H, J=1.9 Hz), 7.18 (d, 1H, J=8.2 Hz), 7.02 (d, 1H, J=5.2 Hz), 6.97 (dd, 1H, J=8.2 & 2.0 Hz), 6.67 (d, 1H, J=5.2 Hz), 2.89–2.83 (m, 2H), 2.11–1.99 (m, 4H), 1.81 (m, 1H), 1.64 (s, 4H), 1.29–1.19 M, 9H), 0.86 (s, 3H) ppm.

B. 4-(5,5,8,8-tetramethyl-5,6,7,8-tetrahydro-2-naphthalenyl)-4,5,6,7-tetrahydro-1-benzothiophene To a CH₂Cl₂ solution (10 mL) containing compound A (654 mg, 1.92 mmol) and triethylsilane (671 mg, 5.77 mmol) was added TFA (680 mg, 5.96 mmol) at −40° C. After 30 min the reaction was quenched with dilute NaHCO₃. The two phase solution was poured into additional sat. NaHCO₃ and the organics extracted with CH₂Cl₂. After drying over MgSO₄ the solvent was removed in vacuo and the residual oil was purified via column chromatography (hexanes/EtOAc (19:1)) yielding 557 mg (1.72 mmol, 90% yield) of compound B as a white solid m.p. 79–81° C.

¹H NMR (CDCl₃) 400 MHz δ 7.17 (d, 1H, J=8.0 Hz), 7.03 (d, 1H, J=1.8 Hz), 6.98 (d, 1H, J=5.2 Hz), 6.81 (dd, 1H, J=8.0 & 1.8 Hz), 6.53 (d, 1H, J=5.3 Hz), 3.93 (m, 1H), 2.88–2.84 (m, 2H), 2.12 (m, 1H), 1.96 (m, 1H), 1.82–1.76 (m, 2H), 1.66 (s, 4H), 1.26–1.25 (m, 9H), 1.21 (s, 3H) ppm.

C. 4-(5,5,8,8-tetramethyl-5,6,7,8-tetrahydro-2-naphthalenyl)-4,5,6,7-tetrahydro-1-benzothiophene-2-carbaldehyde To a Et₂O solution (50 mL) containing compound B (6.40 g, 19.8 mmol) cooled to −20° C. was added 34.9 mL of a 1.7 M pentane solution of t-BuLi (59.4 mmol). The resulting yellow solution stirred at −20° C. for 30 min at which time DMF (2.17 g, 29.7 mmol) was added. After 30 min the reaction had warmed to −10° C. at which time it was quenched with H₂O. The solution was then poured into sat. NaHSO₄ and the organics extracted with Et₂O. After drying over MgSO₄ the solvent was removed in vacuo. The residual yellow solid was dissolved in MeOH and a small amount of Et₂O added. After storing in the freezer overnight the precipitated solid was collected via vacuum filtration yielding 6.73 g (19.1 mmol, 96% yield) of compound C as a light orange solid m.p. 142–145° C.

¹H NMR (CDCl₃) 400 MHz δ 9.71 (s, 1H), 7.23 (s, 1H), 7.21 (d, 1H, J=8.0 Hz), 7.04 (d, 1H, J=1.9 Hz), 6.81 (dd, 1H, J=8.0 & 2.0 Hz), 3.93 (m, 1H), 2.95–2.92 (m, 2H), 2.15 (m, 1H), 2.01 (m, 1H), 1.86–1.77 (m, 2H), 1.68 (s, 4H), 1.27 (s, 6H), 1.26 (s, 3H), 1.22 (s, 3H) ppm.

D. Ethyl (2E)-3-[4-(5,5,8,8-tetramethyl-5,6,7,8-tetrahydro-2-naphthalenyl)-4,5,6,7-tetrahydro-1-benzothien-2-yl]-2-propenoate To a DME solution (20 mL) containing sodium hydride (523 mg, 13.1 mmol, 60% dispersion in mineral oil) was added triethylphosphonoacetate (2.94 g, 13.1 mmol). To this solution was added compound C (3.07 g, 8.72 mmol) in 20 mL of DME. The reaction went for 30 min and was then quenched with H₂O. The solution was poured into additional H₂O and the organics extracted with Et₂O. After drying over MgSO₄ the solvent was removed in vacuo and the residual oil purified via column chromatography (hexanes/EtOAc (19:1)) yielding 3.51 g (8.32 mmol, 95% yield) of compound D as an oil which solidified on standing m.p. 52–55° C.

¹H NMR (CDCl₃) 400 MHz δ 7.59 (d, 1H, J=15.6 Hz), 7.17 (d, 1H, J=8.1 Hz), 7.01 (s(br), 1H), 6.79 (d, 1H, J=8.0 Hz), 6.67 (s, 1H), 6.04 (d, 1H, J=15.6 Hz), 4.18 (q, 2H, J=7.1 Hz), 3.86 (m, 1H), 2.84–2.82 (m, 2H), 2.11 (m, 1H), 1.94 (m, 1H), 1.79–1.73 (m, 2H), 1.65 (s, 4H), 1.29–1.25 (m, 12H), 1.20 (s, 3H) ppm.

E. (2E)-3-[4-(5,5,8,8-tetramethyl-5,6,7,8-tetrahydro-2-naphthalenyl)-4,5,6,7-tetrahydro-1-benzothien-2-yl]-2-propenoic acid To a dioxane solution (4 mL) containing compound D (286 mg, 0.68 mmol) was added lithium hydroxide hydrate (142 mg, 3.39 mmol) and 1 mL of H₂O. After 30 h the heterogeneous solution was diluted with EtOAc and acidified with sat. NaHSO₄. The organic layer was separated, dried (MgSO₄) and the solvent removed in vacuo. The residual oil was purified via column chromatography (CH₂Cl₂/MeOH (15:1)) yielding a foam that was triturated with Et₂O/hexanes. The resulting precipitate was collected via vacuum filtration yielding 202 mg (0.51 mmol, 75% yield) of compound E as a white solid, m.p. 225–229° C. decomp.

¹H NMR (CDCl₃) 400 MHz δ 7.68 (d, 1H, J=15.6 Hz), 7.19 (d, 1H, J=8.0 Hz), 7.03 (d, 1H, J=1.6 Hz), 6.80 (dd, 1H, J=8.0 & 1.7 Hz), 6.73 (s, 1H), 6.04 (d, 1H, J=15.5 Hz), 3.88 (m, 1H), 2.87–2.85 (m, 2H), 2.12 (m, 1H), 1.97 (m, 1H), 1.81–1.76 (m, 2H), 1.67 (s, 4H), 1.27 (s, 6H), 1.22 (s, 3H), 1.19 (s, 3H) ppm.

Example 8

(2E)-3-[4-(5,5,8,8-tetramethyl-5,6,7,8-tetrahydro-2-naphthalenyl)-4,5,6,7-tetrahydro-1,3-benzoxazol-2-yl]-2-propenoic acid A. 2-Methyl-4-(5,5,8,8-tetramethyl-5,6,7,8-tetrahydro-2-naphthalenyl)-4,5,6,7-tetrahydro-1,3-benzoxazol-4-ol To a THF solution (50 mL) containing 6-bromo-1,1,4,4-tetramethyl-1,2,3,4-tetrahydronaphthalene (5.21 g, 19.5 mmol) cooled to −78° C. was added 8.5 mL of a 2.4 M hexanes solution of n-BuLi (20.5 mmol). The resulting orange solution stirred for 30 min when 2-methyl-6,7-dihydro-1,3-benzoxazol-4(5H)-one (2.68 g, 17.7 mmol) in 50 mL of THF was added. The dark solution went for 45 min at −78° C. and was then quenched with H₂O. Upon warming the solution was poured into additional H₂O and the organics extracted with Et₂O (2×). After drying (MgSO₄) the solvent was removed in vacuo and the residual yellow oil purified via column chromatography (hexanes/EtOAc (3:2)) yielding 4.0 g (11.8 mmol, 67% yield) of compound A as an oil.

¹H NMR (CDCl₃) 400 MHz δ 7.37 (d, 1H, J=2.0 Hz), 7.17 (d, 1H, J=8.3 Hz), 6.91 (dd, 1H, J=8.2 & 2.0 Hz), 2.68–2.64 (m, 2H), 2.53 (s, 1H, -OH), 2.40 (s, 3H), 2.11–1.95 (m, 3H), 1.78 (m, 1H), 1.63 (s, 4H), 1.25–1.21 (m, 12H) ppm.

B. 2-Methyl-4-(5,5,8,8-tetramethyl-5,6,7,8-tetrahydro-2-naphthalenyl)-4,5,6,7-tetrahydro-1,3-benzoxazole To a THF solution (40 mL) containing sodium borohydride (4.46 g, 118.0 mmol) cooled to 0° C. was added BF₃.Et₂O (25.1 g, 178 mmol). The resulting white slurry then had compound A (4.0 g, 11.8 mmol) in 75 mL of THF added to it. After 15 min the reaction was quenched by carefully pouring it into sat. NaHCO₃. After the foaming had subsided the organics were extracted with Et₂O (2×). After drying over MgSO₄ the solvent was removed in vacuo and the residual oil purified via column chromatography (hexanes/EtOAc (9:1)) yielding 1.44 g (4.47 mmol, 38% yield) of compound B.

$^1$H NMR (CDCl₃) 400 MHz δ 7.13 (d, 1H, J=8.0 Hz), 7.03 (d, 1H, J=2.0 Hz), 6.77 (dd, 1H, J=8.1 & 2.0 Hz), 3.83 (m, 1H), 2.65–2.60 (m, 2H), 2.36 (s, 3H), 2.07 (m, 1H), 1.91 (m, 1H), 1.77–1.68 (m, 2H), 1.61 (s, 4H), 1.20 (s, 9H), 1.19 (s, 3H) ppm.

C. 2-(Bromomethyl)-4-(5,5,8,8-tetramethyl-5,6,7,8-tetrahydro-2-naphthalenyl)-4,5,6,7-tetrahydro-1,3-benzoxazole To a CCl₄ solution (60 mL) containing compound B (4.79 g, 14.8 mmol) was added AIBN (24 mg, 0.15 mmol, 1 mol %) and NBS (3.16 g, 17.8 mmol). The solution was then immersed in an oil bath which had been preheated to 90° C. After 30 min the solution was allowed to cool to room temperature and the precipitated succinimide was removed via filtration. Removal of the solvent in vacuo and purification via column chromatography (hexanes/EtOAc (15:1)) yielded 2.23 g (5.55 mmol, 37% yield) of compound C as a white foam.

$^1$H NMR (CDCl₃) 400 MHz δ 7.16 (d, 1H, J=8.1 Hz), 7.02 (d, 1H, J=1.9 Hz), 6.78 (dd, 1H, J=8.1 & 1.9 Hz), 4.41 (s, 2H), 2.73–2.67 (m, 2H), 2.12 (m, 1H), 1.94 (m, 1H), 1.82–1.69 (m, 2H), 1.62 (s, 4H), 1.21 (s, 12H) ppm.

D. [4-(5,5,8,8-Tetramethyl-5,6,7,8-tetrahydro-2-naphthalenyl)-4,5,6,7-tetrahydro-1,3benzoxazol-2-yl]methyl acetate.

To an CH₃CN solution (50 mL) containing compound C (2.0 g, 4.98 mmol) was added potassium acetate (978 mg, 9.96 mmol) at room temperature. The resulting slurry stirred for 24 h at which time it was diluted with H₂O and the organics were extracted with EtOAc (2×). After drying over MgSO₄ the solvent was removed in vacuo and the residual oil purified via column chromatography (hexanes/EtOAc (4:1)) yielding 1.54 g (4.04 mmol, 81% yield) of compound D.

$^1$H NMR (CDCl₃) 400 MHz δ 7.15 (d, 1H, J=8.1 Hz), 7.03 (d, 1H, J=1.9 Hz), 6.78 (dd, 1H, J=8.1 & 1.9 Hz), 5.08 (s, 2H), 3.90 (m, 1H), 2.72–2.66 (m, 2H), 2.13–2.08 (m, 4H), 1.94 (m, 1H), 1.79–1.73 (m, 2H), 1.62 (s, 4H), 1.21 (s, 6H), 1.20 (s, 6H) ppm.

E. [4-(5,5,8,8-Tetramethyl-5,6,7,8-tetrahydro-2-naphthalenyl)-4,5,6,7-tetrahydro-1,3-benzoxazol-2-yl]methanol To a MeOH solution (50 mL) containing compound D (1.62 g, 4.24 mmol) was added 75 □L of H₂O and potassium carbonate (1.17 g, 8.48 mmol) at room temperature. After 15 min the solution was diluted with H₂O and the organics extracted with EtOAc. After drying over MgSO₄ the solvent was removed in vacuo yielding 1.33 g (3.92 mmol, 92% yield) of compound E as a white solid which was pure enough to take on.

$^1$H NMR (CDCl₃) 400 MHz δ 7.15 (d, 1H, J=8.1 Hz), 7.04 (d, 1H, J=1.4 Hz), 6.77 (dd, 1H, J=8.1 & 1.6 Hz), 4.62–4.51 (m, 2H), 3.89 (m, 1H), 2.69–2.64 (m, 2H), 2.48 (t, 1H, J=6.4 Hz), 2.10 (m, 1H), 1.92 (m, 1H), 1.78–1.72 (m, 2H), 1.62 (s, 4H), 1.22 (s, 6H), 1.21 (s, 3H), 1.20 (s, 3H) ppm.

F. 4-(5,5,8,8-Tetramethyl-5,6,7,8-tetrahydro-2-naphthalenyl)-4,5,6,7-tetrahydro-1,3-benzoxazole-2-carbaldehyde To a CH₂Cl₂ solution (30 mL) containing compound E (1.43 g, 4.23 mmol), NMO (743 mg, 6.34 mmol) and 2.1 g of 4A powdered molecular sieves was added TPAP (74 mg, 0.21 mmol, 5 mol %). After stirring for 30 min at room temperature the dark slurry was filtered through a bed of celite. The celite was rinsed thoroughly with CH₂Cl₂ and then the solvent was removed in vacuo. The residual dark oil was purified via column chromatography (hexanes/EtOAc (4:1)) yielding 671 mg (1.99 mmol, 47% yield) of compound F.

$^1$H NMR (CDCl₃) 400 MHz δ 9.62 (s, 1H), 7.19 (d, 1H, J=8.1 Hz), 7.04 (d, 1H, J=1.8 Hz), 6.77 (dd, 1H, J=8.1 & 1.9 Hz), 4.00 (m, 1H), 2.84–2.79 (m, 2H), 2.18 (m, 1H), 1.86–1.80 (m, 2H), 1.63 (s, 4H), 1.23 (s, 6H), 1.22 (s, 3H), 1.21 (s, 3H) ppm.

G. Ethyl (2E)-3-[4-(5,5,8,8-tetramethyl-5,6,7,8-tetrahydro-2-naphthalenyl)-4,5,6,7-tetrahydro-1,3-benzoxazol-2-yl]-2-propenoate To a DME solution (10 mL) containing sodium hydride (121 mg, 3.03 mmol, 60% dispersion in mineral oil) was added triethylphosphonoacetate (679 mg, 3.03 mmol) at room temperature. To this solution was added compound F (682 mg, 2.02 mmol) in 10 mL of DME. After 15 min the reaction was quenched with H₂O and the organics were extracted with Et₂O. Upon drying over MgSO₄ the solvent was removed in vacuo and the residual oil was purified via column chromatography (hexanes/EtOAc (9:1)) yielding 648 mg (1.59 mmol, 79% yield) of compound G.

$^1$H NMR (CDCl₃) 400 MHz δ 7.36 (d, 1H, J=16.0 Hz), 7.15 (d, 1H, J=8.1 Hz), 7.04 (d, 1H, J=1.9 Hz), 6.77 (dd, 1H, J=8.1 & 1.9 Hz), 6.61 (d, 1H, J=16.1 Hz), 4.21 (q, 2H, J=7.2 Hz), 3.93 (m, 1H), 2.75–2.69 (m, 2H), 2.12 (m, 1H), 1.95 (m, 1H), 1.82–1.75 (m, 2H), 1.61 (s, 4H), 1.27 (t, 3H, J=7.1 Hz), 1.21 (s, 6H), 1.20 (s, 6H) ppm.

H. (2E)-3-[4-(5,5,8,8-tetramethyl-5,6,7,8-tetrahydro-2-naphthalenyl)-4,5,6,7-tetrahydro-1,3-benzoxazol-2-yl]-2-propenoic acid To a dioxane solution (12 mL) containing compound G (645 mg, 1.58 mmol) was added 3 mL of H₂O followed by lithium hydroxide hydrate (664 mg, 15.8 mmol). After stirring overnight at room temperature the reaction was acidified with sat. NaHSO₄ and the organics were extracted with EtOAc. Upon drying over MgSO₄ and removal of the solvent in vacuo the residual material was purified via column chromatography (CH₂Cl₂/MeOH (9:1)) affording 599 mg (1.58 mmol, 100% yield) of compound H as an off-white solid, m.p. 176–178° C.

$^1$H NMR (CDCl₃) 400 MHz δ 7.44 (d, 1H, J=15.9 Hz), 7.16 (d, 1H, J=8.1 Hz), 7.05 (d, 1H, J=1.9 Hz), 6.78 (dd, 1H, J=8.1 & 1.9 Hz), 6.62 (d, 1H, J=16.1 Hz), 3.95 (m, 1H), 2.78–2.72 (m, 2H), 2.15 (m, 1H), 1.96 (m, 1H), 1.82–1.77 (m, 2H), 1.62 (s, 4H), 1.22 (s, 6H), 1.21 (s, 6H) ppm.

Example 9

(2E)-3-(4-{[(2,6,6-trimethylcyclohexen-1-yl)methyl]amino}benzofuran-2-yl)-2-propenoic acid

A. N-[2-Formyl-3-(methoxymethoxy)phenyl]-2,2-dimethylpropanamide 1-(Trimethylacetamido)-3-(methoxymethoxy)benzene (17.314 g, 73.0 mmol) was dissolved in THF (200 mL) and the solution was cooled to 0° C. under nitrogen. BuLi (2.5 M solution in hexanes, 58.5 mL, 146 mmol) was added and the mixture was allowed to stir at 0° C. for 2 hours at which time DMF (6.20 mL, 80.4 mmol) was added. The resulting mixture was warmed to room temperature and stirred for 3 hours. Saturated aqueous $KH_2PO_4$ (100 mL) and water (100 mL) were added. The two layers were separated and the aqueous layer was extracted with $Et_2O$ (2×50 mL). The combined organics were dried ($MgSO_4$) and concentrated. The residue was purified by silica gel chromatography (4:1 hexane:EtOAc) yielding 15.0 g of compound A (56.5 mmol, 77% yield) as a pale yellow solid.

$^1$H NMR (CDCl$_3$) 400 MHz δ 11.79 (br s, 1H), 10.48 (s, 1H), 8.33 (d, 1H, J=8.4 Hz), 7.40 (t, 1H, J=8 Hz), 6.76 (d, 1H, J=8.4 Hz), 5.21 (s, 2H), 3.43 (s, 3H), 1.26 (s, 9H) ppm.

B. N-(2-Formyl-3-hydroxyphenyl)-2,2-dimethylpropanamide

Compound A (15.0 g, 56.5 mmol) was dissolved in methanol (120 mL). 4-Toluenesulfonic acid monohydrate (12.956 g, 68.0 mmol) was added and the solution was stirred at room temperature for 18 hours, then was concentrated. The residue was dissolved in $Et_2O/CH_2Cl_2$ (125 mL, 4:1) and was washed with saturated aqueous $NaHCO_3$ (3×50 mL). The organics were dried ($Na_2SO_4$) and concentrated to provide 12.2 g (55.3 mmol, 98% yield) of compound B as a yellow solid that was used without further purification.

$^1$H NMR (CDCl$_3$) 400 MHz δ 10.26 (s, 1H), 9.18 (br s, 1H), 7.64 (d, 1H, J=8.4 Hz), 7.37 (t, 1H, J=8.4 Hz), 6.65 (d, 1H, J=8.4 Hz), 1.33 (s, 9H) ppm.

C. Methyl {3-[(2,2-dimethylpropanoyl)amino]-2-formylphenoxy}acetate

Compound B (12.2 g, 55.3 mmol) was dissolved in DMF (100 mL). $K_2CO_3$ (7.664 g, 55.5 mmol) was added followed by methyl bromoacetate (5.25 mL, 55.5 mmol). The mixture was stirred at room temperature for 5 hours, then was filtered. 1.0 N aqueous HCl (100 mL) was added and the mixture was extracted with $Et_2O$ (4×25 mL). The combined organics were dried ($Na_2SO_4$) and concentrated and the crude residue was recrystallized from $Et_2O$/hexane (9:1) to provide 9.44 g (32.2 mmol, 58% yield) of compound C as a tan solid.

$^1$H NMR (CDCl3) 400 MHz δ 11.86 (s, 1H), 10.58 (s, 1H), 8.38 (d, 1H, J=8.6 Hz), 7.44 (t, 1H, J=8.6 Hz), 6.45 (d, 1H, J=8.6 Hz), 4.72 (s, 2H), 3.77 (s, 3H), 1.31 (s, 9H) ppm.

D. Methyl 4-[(2,2-dimethylpropanoyl)amino]benzofuran-2-carboxylate

Compound C (9.44 g, 32.2 mmol) was dissolved in DMF (100 mL). $K_2CO_3$ (17.793 g, 129 mmol) was added and the mixture was heated to 120° C. for 5 hours. The mixture was cooled to room temperature and filtered. To the filtrate was added 1.0 N HCl (200 mL) and the mixture was extracted with EtOAc (4×50 mL). The combined organics were dried ($MgSO_4$) and concentrated. The crude residue was purified by silica gel chromatography (4:1 hexane:EtOAc) to provide 3.61 g (13.2 mmol, 41%) of compound D as a cottony white solid, along with the decarboxylated material (white solid, 1.21 g, 17%).

$^1$H NMR (CDCl$_3$) 400 MHz δ 7.71 (s, 1H), 7.52 (d, 1H, J=6.7 Hz), 7.41 (s, 1H), 7.29 (m, 2H), 3.90 (s, 3H), 1.31 (s, 9H) ppm.

E. N-[2-(Hydroxymethyl)benzofuran-4-yl]-2,2-dimethylpropanamide

LiBH$_4$ (0.1095 g, 5.03 mmol) was suspended in THF (5 mL). A solution of compound D (0.996 g, 3.62 mmol) in THF (6 mL) was slowly added (gas evolution occurred) and the mixture was heated to reflux for 3 hours. The mixture was cooled to room temperature and treated with saturated aqueous ammonium chloride (20 mL). The mixture was extracted with $Et_2O$ (4×10 mL). The combined organics were dried ($MgSO_4$) and concentrated. The crude residue was purified by silica gel chromatography (1:1 hexanes:EtOAc) to provide 0.53 g (2.14 mmol, 59% yield) of compound E as a white solid.

$^1$H NMR (CDCl$_3$) 400 MHz δ 7.51 (s, 1H), 7.50 (d, 1H, J=8.3 Hz), 7.20 (t, 1H, J=8.3 Hz), 7.17 (d, 1H, J=8.3 Hz), 6.52 (s, 1H), 4.68 (s, 3H), 2.43 (br s, 1H), 1.33 (s, 9H) ppm.

F. (4-Aminobenzofuran-2-yl)methanol

Compound E (2.29 g, 9.28 mmol) and 5.0 N NaOH (50 mL) were heated to 110° C. for 3 days. The mixture was cooled to room temperature and extracted with $Et_2O$ (4×25 mL). The organics were dried ($Na_2SO_4$) and concentrated. The crude residue was purified by silica gel chromatography (1:1 hexanes:EtOAc) to provide 0.47 g (2.88 mmol, 31% yield) of compound F as a yellow solid, along with recovered starting material (0.65 g).

$^1$H NMR (CDCl$_3$) 400 MHz δ 7.06 (t, 1H, J=8.1 Hz), 6.89 (d, 1H, J=8.1 Hz), 6.55 (s, 1H), 6.47 (d, 1H, J=8.1 Hz), 4.71 (s, 2H) ppm.

G. Tert-butyl 2-(hydroxymethyl)benzofuran-4-ylcarbamate

Compound F (0.47 g, 2.88 mmol) was dissolved in THF (5 mL). Di-tert-butyl dicarbonate (0.627 g, 2.87 mmol) was added and the solution was heated to reflux for 18 hours. The solution was cooled to room temperature and concentrated. The crude residue was purified by silica gel chromatography (1:1 hexanes:EtOAc) to provide 0.65 g (2.49 mmol, 86% yield) of the compound G as a pale yellow solid.

$^1$H NMR (CDCl$_3$) 400 MHz δ 7.48 (d, 1H, J=8.1 Hz), 7.20 (t, 1H, J=8.1 Hz), 7.19 (d, 1H, J=8.1 Hz), 6.64 (s, 1H), 6.56 (s, 1H), 4.73 (s, 2H), 1.85 (br s, 1H), 1.52 (s, 9H) ppm.

H. Tert-butyl-2-formylbenzofuran-4-ylcarbamate

Compound G (0.65 g, 2.49 mmol) was dissolved in CH$_2$Cl$_2$ (24 mL). Dess-Martin periodinane (1.179 g, 2.78 mmol) was added and the mixture was stirred at room temperature for 2 hours. The mixture was concentrated and the crude residue was purified by silica gel chromatography (3:1 hexanes:EtOAc) to provide 0.53 g (2.02 mmol, 81% yield) of compound H as a yellow solid.

¹H NMR (CDCl₃) 400 MHz δ 9.81 (s, 1H), 7.67 (s, 1H), 7.53 (d, 1H, J=8.2 Hz), 7.44 (t, 1H, J=8.2 Hz), 7.28 (d, 1H, J=8.2 Hz), 6.90 (br s, 1H), 1.53 (s, 9H) ppm.

I. Methyl (2E)-3-{4-[(tert-butoxycarbonyl)amino]benzofuran-2-yl}-2-propenoate Compound H (0.53 g, 2.02 mmol) was dissolved in CH₂Cl₂ (4 mL). Methyl (triphenylphosphoranylidene)acetate (0.751 g, 2.25 mmol) was added and the solution was stirred at room temperature for 16 hours. The mixture was concentrated and the crude residue was purified by silica gel chromatography (3:1 hexanes:EtOAc) to provide 0.50 g (1.58 mmol, 78% yield) of compound I as a pale yellow solid.
¹H NMR (CDCl₃) 400 MHz δ 7.53 (d, 1H, J=8.0 Hz), 7.49 (d, 1H, J=15.7 Hz), 7.28 (t, 1H, J=8.0 Hz), 7.17 (d, 1H, J=8.0 Hz), 6.93 (s, 1H), 6.66 (s, 1H), 6.53 (d, 1H, J=15.7 Hz), 3.79 (s, 3H), 1.52 (s, 9H) ppm.

J. Methyl (2E)-3-(4-aminobenzofuran-2-yl)-2-propenoate

Compound I (0.50 g, 1.58 mmol) was dissolved in CH₂Cl₂ (1.5 mL) and trifluoroacetic acid (1.5 mL). The solution was stirred at room temperature for 45 minutes. The solution was diluted with CH₂Cl₂ (10 mL) and saturated aqueous sodium bicarbonate was added slowly until the solution reached pH 8. The two layers were separated and the aqueous layer was extracted with CH₂Cl₂ (3×10 mL). The organics were dried (Na₂SO₄) and concentrated to provide 0.24 g (1.11 mmol, 70% yield) of compound J as a yellow solid.
¹H NMR (CDCl₃) 400 MHz δ 7.49 (d, 1H, J=15.5 Hz), 7.13 (t, 1H, J=8.2 Hz), 6.88 (d, 1H, J=8.2 Hz), 6.84 (s, 1H), 6.48 (d, 1H, J=15.5 Hz), 6.47 (d, 1H, J=8.2 Hz), 3.79 (s, 3H) ppm.

K. Methyl (2E)-3-(4-{[(2,6,6-trimethyl-1-cyclohexen-1-yl)methyl]amino}benzofuran-2-yl)-2-propenoate Compound J (0.048 g, 0.221 mmol) was dissolved in acetone (0.50 mL). K₂CO₃ (0.0374 g, 0.271 mmol) was added, followed by a solution of 2-(bromomethyl)-1,3,3-trimethyl-1-cyclohexene (0.049 g, 0.224 mmol) in acetone (0.50 mL). The mixture was stirred at room temperature for 2.5 days. Saturated aqueous KH₂PO₄ (15 mL) was added and the mixture was extracted with EtOAc (3×7 mL). The organics were dried (Na₂SO₄) and concentrated. The crude residue was purified by silica gel chromatography (3:1 hexanes:EtOAc) to provide 0.041 g (0.12 mmol, 52% yield) of compound K as a yellow oil.
¹H NMR (CDCl₃) 400 MHz δ 7.46 (d, 1H, J=15.5 Hz), 7.20 (t, 1H, J=8.1 Hz), 6.85 (s, 1H), 6.81 (d, 1H, J=8.1 Hz), 6.46 (d, 1H, J=15.5 Hz), 6.35 (d, 1H, J=8.1 Hz), 3.78 (s, 3H), 3.70 (s, 2H), 1.99 (t, 1H, J=8.2 Hz), 1.66 (s, 3H), 1.64 (m, 2H), 1.48 (m, 2H), 1.02 (s, 6H) ppm.

L. (2E)-3-(4-{[(2,6,6-trimethylcyclohexen-1-yl)methyl]amino}benzofuran-2-yl)2-propenoic acid Compound K (0.0409 g, 0.116 mmol) was dissolved in THF/MeOH/H₂O (4:1:1, 1.5 mL). Lithium hydroxide (0.0164 g, 0.391 mmol) was added and the solution was stirred at room temperature for 7 hours. Saturated aqueous KH₂PO₄ (15 mL) was added and the mixture was extracted with EtOAc (3×10 mL). The organics were dried (Na₂SO₄) and concentrated. The crude residue was purified by silica gel chromatography (1:1 hexanes:EtOAc) to provide 0.0271 g (0.080 mmol, 69% yield) of compound L as a yellow solid m.p. 202° C. (dec.).
¹H NMR (CD₃OD) 400 MHz δ 7.47 (d, 1H, J=15.5 Hz), 7.30 (s, 1H), 7.17 (t, 1H, J=8.1 Hz), 6.72 (d, 1H, J=8.1 Hz), 6.32 (d, 1H, J=15.5 Hz), 6.31 (d, 1H, J=8.1 Hz), 3.70 (s, 2H), 2.02 (app t, 1H, J=8.1 Hz), 1.68 (s, 3H), 1.65 (m, 2H), 1.50 (m, 2H), 1.04 (s, 6H) ppm.

Example 10

(2E)-3[4-(4-Isopropoxy-1-naphthalenyl)-4,5,6,7,-tetrahydro-1-benzofuran-2-yl]-2-propenoic acid

A. 4-Bromo-1-naphthol

To an acetonitrile solution (275 mL) containing 1-naphthol (10 g, 69 mmol) at room temperature was added N-bromosuccinimide (1 eq, 12.35 g, 69 mmol) in portions over 10 minutes. The resulting mixture was stirred for 1 h at room temperature. The mixture was concentrated under reduced pressure and was then diluted with ether (100 mL). The mixture was poured into water (100 mL) and extracted with ether (2×100 mL). The combined organic layer was dried (MgSO₄) and concentrated under reduced pressure to provide 15.0 g of a brown solid that was identified as 4-bromo-1-naphthol, m.p. 125–127° C.
¹H NMR (CDCl₃) 400 MHz δ 8.16 (d, 1H, J=8.5 Hz), 8.14 (d, 1H, J=8.4 Hz), 7.58 (ddd, 1H, J=1.6, 6.7, 8.2 Hz), 7.55 (d, 1H, J=8.0 Hz), 7.51 (ddd, 1H, J=1.3, 7.0, 8.3 Hz), 6.67 (d, 1H, J=8.0 Hz), 5.25 (s, 1H) ppm.

B. 4-isopropoxy-1-bromonaphthalene

The following is an adaptation of the method of Bringmann. A solution containing 4-bromo-1-naphthol (10.0 g, 0.045 mol), potassium carbonate (31 g, 0.224 mol), and 2-bromopropane (27.6 g, 0.224 mol) in DMF was heated at reflux for 1 h under a nitrogen atmosphere. The mixture was cooled to room temperature and the solvent was removed under reduced pressure. The resultant residue was subjected to silica gel chromatography using a 50% ethyl acetate-hexane mixture as the eluent to provide 4-isopropoxy-1-bromonaphthalene.
¹H NMR (CDCl₃) 400 MHz δ 8.26 (d, 1H, J=7.9 Hz), 8.11 (d, 1H, J=8.4 Hz), 7.60 (d, 1H, J=8.3 Hz), 7.55 (ddd, 1H, J=1.5, 6.8, 8.3 Hz), 7.46 (ddd, 1H, J=1.1, 6.8, 8.3 Hz), 6.67 (d, 1H, J=8.2 Hz), 4.68 (sept, 1H, J=5.8 Hz), 1.41 (d, 6H, J=6.1 Hz) ppm.

C. 4-(4-Isopropoxy-1-naphthalenyl)-4,5,6,7-tetrahydro-1-benzofuran-4-ol

To a THF solution (30 mL) containing 4-isopropoxy-1-bromonaphthalene (4.0 g, 15.1 mmol) cooled to −78° C. was added 9.3 mL of a 1.54 M hexanes solution of n-BuLi (14.3 mmol). The resulting solution was stirred for 10 min and then 6,7-dihydro-4(5H)-benzofuranone (1.87 g, 13.7 mmol) in 10 mL of THF was added. After stirring for 30 min the reaction was quenched with H₂O. Upon warming the solution was poured into additional H₂O and the organics were extracted with Et₂O. After drying over MgSO₄ the solvent was removed in vacuo and the residual oil purified via column chromatography (hexanes/EtOAc (5:1)) yielding 3.6 g (11.2 mmol, 78% yield) of compound C.

¹H NMR (acetone-d₆) 400 MHz δ 8.23–8.35 (m, 2H), 7.51 (d, 1H, J=7.8 Hz), 7.35 (ddd, 1H, J=1.5, 6.8, 8.3 Hz), 7.28–7.33 (m, 2H), 6.83 (d, 1H, J=8.2 Hz), 6.08 (d, 1H, J=2.1 Hz), 4.79 (sept, 1H, J=6.1 Hz), 4.42 (s, 1H), 2.81 (bs, 1H), 2.68 (t, 2H, J=6.2 Hz), 2.00–2.51 (m, 3H), 1.41 (d, 3H, J=2.8 Hz), 1.39 (d, 3H, J=2.7 Hz) ppm.

D. 4-(4-Isopropoxy-1-naphthalenyl)-4,5,6,7-tetrahydro-1-benzofuran

To a THF solution (100 mL) containing sodium borohydride (3.75 g, 99 mmol) cooled to 0° C. was added BF₃.Et₂O (69.0 g, 486 mmol). The resulting white slurry stirred for 15 min when compound C (described above) (3.20 g, 9.9 mmol) in 65 mL of THF was added. After 15 min the reaction mixture was very carefully poured into sat. NaHCO₃. The solution was then poured into water and the mix was extracted with ether. The combined organic layer was dried (MgSO₄) and concentrated in vacuo and the residual yellow oil was purified via flash chromatography (hexanes/EtOAc (49:1) yielding 2.33 g (7.6 mmol, 77% yield) of compound D as a colorless glass.

¹H NMR (CDCl₃) 400 MHz δ 8.34 (d, 1H, J=5.2 Hz), 8.08 (d, 1H, J=8.3 Hz), 7.40–7.60 (m, 2H), 7.29 (dd, 1H, J=0.8, 1.9 Hz), 6.99 (d, 1H, J=8.1 Hz), 6.70 (d, 1H, J=8.1 Hz), 6.05 (d, 1H, J=1.8 Hz), 4.67 (sept, 1H, J=6.1 Hz), 4.60–4.65 (m, 1H), 2.60–2.78 (m, 2H), 2.11–2.24 (m, 1H), 1.72–1.92 (m, 3H), 1.42 (d, 6H, J=6.1 Hz) ppm.

E. [4-(4-Isopropoxy-1-naphthalenyl)-4,5,6,7-tetrahydro-1-benzofuran]-2-carboxaldehyde To a THF solution (6 mL) containing compound D (0.500 g, 1.63 mmol) cooled to 0° C. was added 1.06 mL of a 1.54 M hexanes solution of n-BuLi (1.63 mmol). The blue solution stirred for 15 min at which time DMF (0.2 mL) was added and the solution turned yellow. After 15 min the reaction was quenched with sat. NaHSO₄, poured into water, and the organics extracted with Et₂O. The combined organic layer was dried (MgSO₄) and the solvent was removed in vacuo and the residual amber gum purified via flash chromatography (hexanes/EtOAc (85/15)) affording 0.444 g (1.33 mmol, 81% yield) of compound E as a yellow foam.

¹H NMR (CDCl₃) 400 MHz δ 9.44 (s, 1H), 8.35 (dd, 1H, J=1.1, 8.2 Hz), 8.01 (d, 1H, J=7.9 Hz), 7.43–7.58 (m, 2H), 6.91 (d, 1H, J=8.1 Hz), 6.88 (s, 1H), 6.69 (d, 1H, J=8.1 Hz), 4.69 (sept, 1H, J=6.0 Hz), 4.62–4.68 (bs, 1H), 2.71–2.90 (m, 2H), 2.13–2.25 (m, 1H), 1.80–1.99 (m, 3H), 1.41 (d, 6H, J=6.1 Hz) ppm.

F. Ethyl (2E)-3-[4-(4-Isopropoxy-1-naphthalenyl)-4,5,6,7-tetrahydro-1-benzofuran-2-yl]-2-propenoate To a DME solution (5 mL) containing sodium hydride (0.080 g, 1.99 mmol, 60% dispersion in mineral oil) was added triethylphosphonoacetate (0.446 g, 1.99 mmol) at room temperature. To the resulting solution was added compound E (0.444 g, 1.33 mmol) in 5 mL of DME. The reaction stirred for 25 min at which time it was quenched with H₂O. The solution was diluted with Et₂O and the organic layer separated. The aqueous layer was extracted with Et₂O and then the combined organic layers were dried over MgSO₄. Removal of the solvent in vacuo and purification via column chromatography (hexanes/EtOAc (9:1)) yielded 0.475 g (1.17 mmol, 87% yield) of compound F as a light yellow foam.

¹H NMR (CDCl₃) 400 MHz δ 8.33 (dd, 1H, J=1.5, 8.2 Hz), 8.03 (d, 1H, J=8.0 Hz), 7.42–7.53 (m, 2H), 7.30 (d, 1H, J=15.6 Hz), 6.94 (1H, J=7.9 Hz), 6.68 (d, 1H, J=8.1 Hz), 6.25 (s, 1H), 6.22 (d, 1H, J=15.6 Hz), 4.67 (sept, 1H, J=6.1 Hz), 4.59 (bs, 1H), 4.19 (q, 2H, J=7.2 Hz), 2.65–2.80 (m, 2H), 2.10–2.21 (m, 1H), 1.77–1.92 (m, 3H), 1.41 (d, 6H, J=6.1 Hz), 1.26 (t, 3H, J=7.2 Hz) ppm.

G. (2E)-3[4-(4-Isopropoxy-1-naphthalenyl)-4,5,6,7,-tetrahydro-1-benzofuran-2-yl]-2-propenoic acid To a dioxane solution (200 mL) containing compound F (0.475 g, 1.17 mmol) was added lithium hydroxide hydrate (0.49 g, 11.7 mmol) followed by 1.5 mL of H₂O. After stirring 14 h TLC showed some starting material left so the solution was diluted with an additional 1 mL H₂O and stirred an additional 22 h. The solution was acidified with sat. NaHSO₄, extracted with EtOAc and dried (MgSO₄). The crude acid was purified using a 2% methanol-dichloromethane mixture as the eluent to provide 0.374 g of product (0.99 mmol, 85% yield), m.p. 179–181° C. (d).

¹H NMR (DMSO-d₆) 400 MHz δ 11.90–12.50 (bs, 1H), 8.17 (d, 1H, J=7.4 Hz), 8.07–8.12 (m, 1H), 7.42–7.55 (m, 2H), 7.25 (d, 1H, J=15.7 Hz), 6.90 (d, 1H, 7.9 Hz), 6.84 (d, 1H, J=7.8 Hz), 6.48 (s, 1H), 6.02 (d, 1H, J=15.2 Hz), 4.70 (sept, 1H, J=6.1 Hz), 4.60 (bs, 1H), 2.60–2.78 (m, 2H), 2.02–2.10 (m, 1H), 1.64–1.80 (m, 3H), 1.32 (d, 6H, J=6.1 Hz) ppm.

Example 11

(2E)-3-{4-[4-Dimethylamino)-3-ethylphenyl]-4,5,6,7-tetrahydro-1-benzofuran-2-yl}-2-propenoic acid

A. 4-Bromo-2-ethyl-N,N-dimethylaniline

To a 37% aqueous formaldehyde solution (158 mL) containing 126 mL of a 3.0 M sulfuric acid solution (378 mmol) was added at 0° C. a THF solution (800 mL) containing 4-bromo-2-ethyl aniline (10.0 g, 50 mmol) and sodium borohydride (47.4 g, 1.25 mol) portionwise. After complete addition the cold bath was removed and stirring continued for 2.5 hr. The reaction was quenched with H₂O and MeOH and then the bulk of the THF removed in vacuo. The residual material was basified with 2.0 N NaOH and the organics were extracted with EtOAc (2×). After drying over MgSO₄ the solvent was removed in vacuo and the residual oil purified via column chromatography (5% EtOAc/hexanes) yielding 5.46 g (23.9 mmol) of compound A plus unreacted starting material.

¹H NMR (CDCl₃) 400 MHz δ 7.31 (d, 1H, J=2.4 Hz), 7.23 (d, 1H, J=2.4 Hz), 6.92 (d, 1H, J=8.6 Hz), 2.68 (q, 2H, J=7.6 Hz), 2.64 (s, 6H), 1.23 (t, 3H, J=7.5 Hz) ppm.

B. N-[2-Ethyl-4-(4,5,6,7-tetrahydro-1-benzofuran-4-yl)phenyl]-N,N-dimethylamine To a THF solution (6 mL) containing compound A (648 mg, 2.84 mmol) cooled to −78° C. was added 1.2 mL of a 2.5 M hexanes solution of n-BuLi (2.98 mmol). After 30 min at −78° C. 6,7-dihydro-4(5H)-benzofuranone (367 mg, 2.70 mmol) in 5 mL THF was added. The reaction stirred for 3 hr at which time it was quenched with H₂O and the organics were extracted with Et₂O. After drying over MgSO₄ the solvent was removed in vacuo. The residual oil was dissolved in 15 mL THF and then added dropwise to a THF solution (10 mL) containing sodium borohydride (1.02 g, 27.0 mmol) and BF₃.Et₂O (5.7 g, 40.5 mmol) at 0° C. The reaction stirred for 10 min and was then carefully quenched with sat. NaHCO₃. The two phase solution was then poured into 2.0 N NaOH and the organics were extracted with Et₂O. Upon drying over MgSO₄ the solvent was removed in vacuo and the residual oil purified via column chromatography (hexanes/EtOAc (15:1)) yielding 456 mg (1.70 mmol, 63% for the 2 steps) of compound B.

¹H NMR (CDCl₃) 400 MHz δ 7.23 (d, 1H, J=1.8 Hz), 6.99–6.97 (m, 2H), 6.89 (dd, 1H, J=8.1 & 2.2 Hz), 6.02 (d, 1H, J=1.7 Hz), 3.79 (m, 1H), 2.70–2.62 (m, 10H), 2.05 (m, 1H), 1.91 (m, 1H), 1.75 (m, 1H), 1.64 (m, 1H), 1.20 (t, 3H, J=7.6 Hz) ppm.

C. 4-[4-Dimethylamino)-3-ethylphenyl]-4,5,6,7-tetrahydro-1-benzofuran-2-carbaldehyde To a Et₂O solution (20 mL) containing compound B (1.73 g, 6.44 mmol) cooled to −40° C. was added 6.8 mL of a 1.7 M pentane solution of t-BuLi (11.6 mmol). The resulting orange solution stirred for 30 min when DMF (848 mg, 11.6 mmol) was added. The reaction went an additional 20 min and was then quenched with H₂O. The two phase solution was poured into additional H₂O and the organics were extracted with Et₂O (2×). After drying over MgSO₄ the solvent was removed in vacuo and the residual yellow oil was purified via column chromatography (hexanes/EtOAc (4:1)) yielding 1.32 g (4.45 mmol, 69% yield) of compound C.

¹H NMR (CDCl₃) 400 MHz δ 9.42 (s, 1H), 7.00–6.95 (m, 2H), 6.86–6.85 (m, 1H), 3.81 (m, 1H), 2.78–2.62 (m, 10H), 2.09 (m, 1H), 2.01 (m, 1H), 1.80 (m, 1H), 1.68 (m, 1H), 1.19 (t, 3H, J=7.6 Hz) ppm.

D. Ethyl (2E)-3-{4-[4-(dimethylamino)-3-ethylphenyl]-4,5,6,7-tetrahydro-1-benzofuran-2-yl}-2-propenoate To a DME solution (14 mL) containing sodium hydride (284 mg, 7.10 mmol, 60% dispersion in mineral oil) was added tiethylphosphonoacetate (1.59 g, 7.10 mmol). After 5 min compound C (1.41 g, 4.73 mmol) in 20 mL DME was added. Upon stirring an additional 20 min the reaction was quenched with H₂O and the organics extracted with Et₂O. After drying over MgSO₄ and removal of the solvent in vacuo the residual oil was purified via column chromatography (hexanes/EtOAc (9:1)) yielding 1.34 g, (3.65 mmol, 77% yield) of compound D.

¹H NMR (CDCl₃) 400 MHz δ 7.29 (d, 1H, J=15.5 Hz), 6.98–6.96 (m, 2H), 6.87 (d(br), 1H, J=8.1 Hz), 6.25 (s, 1H), 6.20 (d, 1H, J=15.7 Hz), 4.19 (q, 2H, J=7.1 Hz), 3.77 (m, 1H), 2.70–2.64 (m, 10H), 2.05 (m, 1H), 1.95 (m, 1H), 1.78 (m, 1H), 1.65 (m, 1H), 1.28 (t, 3H, J=7.1 Hz), 1.19 (t, 3H, J=7.6 Hz) ppm.

E. (2E)-3-{4-[4-Dimethylamino)-3-ethylphenyl]-4,5,6,7-tetrahydro-1-benzofuran-2-yl}-2-propenoic acid.

To a dioxane (15 mL)/H₂O (4 mL) solution containing compound D (1.49 g, 4.05 mmol) was added lithium hydroxide hydrate (1.70 g, 40.5 mmol) at room temperature. The reaction stirred overnight and was then acidified with sat. NaHSO₄ and the organics were extracted with EtOAc (2×). After drying over MgSO₄ the solvent was removed in vacuo and the residual yellow oil was purified via column chromatography (CH₂Cl₂/MeOH (15:1)) yielding 708 mg (2.09 mmol, 52% yield) of compound E as a yellow solid, m.p. 75–78° C.

¹H NMR (CDCl₃) 400 MHz δ 7.32 (d, 1 H, J=15.5 Hz), 6.99–6.96 (m, 2H), 6.87 (dd, 1H, J=8.2 & 2.2 Hz), 6.30 (s, 1H), 6.19 (d, 1H, J=15.6 Hz), 3.77 (m, 1H), 2.72–2.64 (m, 10H), 2.07 (m, 1H), 1.96 (m, 1H), 1.78 (m, 1H), 1.65 (m, 1H), 1.19 (t, J=7.5 Hz) ppm.

Example 12

(2E)-3-{4-[(E)-2-(2,6,6-Trimethyl-1-cyclohexen-1-yl)ethenyl]-1-benzofuran-2-yl}-2-propenoic acid

A. 1-Benzofuran-4-ylmethanol

To a CH₂Cl₂ solution (15 mL) containing the methyl 1-benzofuran-4-carboxylate (1 g, 5.68 mmol) cooled to −78° C. was added diisobutylaluminium hydride dropwise. After stirring for 30 min the reaction was quenched with the slow addition of MeOH. Upon warming the white precipitate was filtered through a bed of celite and rinsed thoroughly with EtOAc. The EtOAc layer was washed with sat. NaHSO₄ and H₂O. After drying over MgSO₄, the solvent was removed in vacuo yielding 0.75 g (5.13 mmol, 94% yield) of compound A as a white solid.

¹H NMR (CDCl₃) 400 MHz δ 7.63 (s, 1H), 7.45 (d, 1H, J=8 Hz), 7.28–7.19 (m, 2H), 6.90 (s, 1H), 4.92 (d, 2H, J=5.6 Hz), 1.66 (t, 1H, J=6 Hz) ppm.

B. 1-Benzofuran-4-carboxaldehyde

To a CHCl₃ solution (10 mL) containing compound A (0.5 g, 3.42 mmol) at room temperature, was added manganese dioxide (5.95 g, 68.4 mmol). The reaction stirred overnight after which the black slurry was filtered through a bed of celite and rinsed thoroughly with CHCl₃. The solvent was removed in vacuo yielding 0.41 g (2.86 mmol, 83% yield) of compound B as a clear liquid.

¹H NMR (CDCl₃) 400 MHz δ 10.17 (s, 1H), 7.77 (s, 1H), 7.69–7.69 (m, 2H), 7.49 (s, 1H), 7.44 (t, 1H, J=8 Hz) ppm.

C. 4-[(E)-2-(2,6,6-Trimethyl-1-cyclohexen-1-yl)ethenyl]-1-benzofuran

To a THF solution (15 mL) containing the dimethyl (2,6,6-trimethyl-1-cyclohexen-1-yl)methylphosphonate (2.18 g, 4.55 mmol) cooled to −78° C., was added n-butyl lithium (1.9 mL, 4.77 mmol) dropwise. After stirring for 2 hr compound B (0.44 g, 3.03 mmol) in a THF (5 mL) solution was added dropwise. After stirring for a further 3 hr at room temperature the solution was quenched with H₂O and the organics extracted with Et₂O. The Et₂O layer was washed with H₂O and dried over MgSO₄. The solvent was removed in vacuo and the brown residual oil purified via column chromatography (hexanes/EtOAc (9:1)) yielding 90 mg (0.34 mmol, 8% yield) of compound C as a clear oil.

¹H NMR (CDCl₃) 400 MHz δ 7.62 (s, 1H), 7.36–7.26 (m, 2H), 7.24 (d, 1H, J=4.5 Hz), 6.94 (s, 1H), 6.80 (d, 1H, J=16 Hz), 6.63 (d, 1H, J=8 Hz), 2.06 (t, 2H, J=8 Hz), 1.79 (s, 3H), 1.67–1.61 (m, 2H), 1.51–1.48 (m, 2H), 1.08 (s, 6H) ppm.

D. 4-[(E)-2-(2,6,6-Trimethyl-1-cyclohexen-1-yl)ethenyl]-1-benzofuran-2-carbaldehyde To a Et₂O solution (1.5 mL) containing compound C (90 mg, 0.34 mmol) cooled to −40° C. was added t-butyl lithium (0.5 mL, 0.845 mmol) dropwise. After stirring for 30 min DMF (65 μL, 0.84 mmol) was added dropwise. After stirring for an additional 30 min the reaction was quenched with H₂O. The organics were extracted with Et₂O and washed with H₂O. After drying over MgSO₄ the solvent was removed in vacuo yielding 80 mg (0.27 mmol, 88% yield) of compound D as a yellow oil.

$^1$H NMR (CDCl₃) 400 MHz δ 9.85 (s, 1H), 7.72 (s, 1H), 7.48–7.40 (m, 3H), 6.87 (d, 1H, J=16 Hz), 6.65 (d, 1H, J=16 Hz), 2.07 (t, 2H, J=8 Hz), 1.79 (s, 3H), 1.67–1.63 (m, 2H), 1.51–1.48 (m, 2H), 1.08 (s, 6H) ppm.

E. Ethyl (2E)-3-{4-[(E)-2-(2,6,6-trimethyl-1-cyclohexen-1-yl)ethenyl]-1-benzofuran-2-yl}-2-propenoate To a DME solution (1 mL) containing NaH (16.3 mg, 0.41 mmol) and triethylphosphonoacetate (81 μL, 0.41 mmol) was added compound D in 1 mL of DME dropwise. After stirring for 3 hr the reaction was quenched with H₂O and the organics extracted with Et₂O. The Et₂O layer was washed with H₂O and dried over MgSO₄. The solvent was removed in vacuo yielding 65 mg (0.18 mmol, 66% yield) of compound E as a yellow oil.

$^1$H NMR (CDCl₃) 400 MHz δ 7.55 (d, 1H, J=16 Hz), 7.3 (s, 3H), 7.08 (s, 1H), 6.80 (d, 1H, J=16 Hz), 6.6–6.5 (dd, 2H, J=16, 12 Hz), 4.27 (q, 2H, J=8 Hz), 2.06 (t, 2H, J=8 Hz), 1.78 (s, 3H), 1.65–1.61 (m, 2H), 1.50–1.47 (m, 2H), 1.33 (t, 3H, J=8 Hz), 1.07 (s, 6H) ppm.

F. (2E)-3-{4-[(E)-2-(2,6,6-trimethyl-1-cyclohexen-1-yl)ethenyl]-1-benzofuran-2-yl}-2-propenoic acid To a dioxane solution (1 mL) containing compound E (65 mg, 0.18 mmol) at room temperature was added lithium hydroxide monohydrate (74 mg, 1.78 mmol) followed by 150 μL of H₂O. After stirring for 12 hr the reaction was diluted with H₂O, acidified with sat. NaHSO₄ and the organics extracted with EtOAc. After drying with MgSO₄ the solvent was removed in vacuo and the residual yellow solid was purified via column chromatography (CH₂Cl₂/MeOH (15:1) yielding 0.044 g (0.13 mmol, 73% yield) of compound F as a yellow solid.

hu 1H NMR (CDCl₃) 400 MHz δ 7.63 (d, 1H, J=16 Hz), 7.32 (s, 3H), 7.14 (s, 1H), 6.81 (d, 1H, J=16 Hz), 6.60–6.53 (dd, 2H, J=12, 12 Hz), 2.06 (t, 2H, J=8 Hz), 1.78 (s, 3H), 1.65–1.61 (m, 2H), 1.51–1.48 (m, 2H), 1.074 (s, 6H) ppm.

Example 13

4-(5,5,8,8-Tetramethyl-5,6,7,8-tetrahydro-2-naphthalenyl)-4,5,6,7-tetrahydro-1-benzofuran-2-carboxylic acid A. 4-(5,5,8,8-Tetramethyl-5,6,7,8-tetrahydro-2-naphthalenyl)-4,5,6,7-tetrahydro-1-benzofuran-2-carboxylic acid A methanol solution (20 mL) was mixed with 4-(5,5,8,8-tetramethyl-5,6,7,8-tetrahydro-2-naphthalenyl)-4,5,6,7-tetrahydro-1-benzofuran]-2-carboxaldehyde (100 mg, 0.30 mmol, see example 1 part C for preparation), 5.0 N NaOH (10 mL) and Ag₂O (138 mg, 0.59 mmol. The resulting black heterogeneous reaction mixture was allowed to stir at room temperature for a period of 17 hours. The reaction mixture was diluted with water and washed with ethyl ether. The ether washes were discarded and the aqueous mixture was made acidic (pH 3.0) using concentrated HCl. The resulting mixture was extracted with ether and dried over MgSO₄. The solvent was evaporated in vacuo to yield 73 mg of pure solid.

$^1$H NMR (CDCl₃) 400 MHz δ 7.20 (d, 1H), 7.04 (s, 1H), 7.00 (s, 1H), 6.83 (d, 1H), 3.8 (s, 1H), 2.80(t, 2H), 2.15 (m, 1H), 2.05–1.98 (m, 1H), 1.90–1.80 (m, 1H), 1.78–1.70 (m, 5H), 1.38–1.20 (m, 12H) ppm.

Example 14

[4-(5,5,8,8,-Tetramethyl-5,6,7,8-tetrahydro-2-naphthalenyl)-4,5,6,7-tetrahydro-1-benzofuran]-2-(2,4-thiazolidinedione)

A. [4(5,5,8,8,-Tetramethyl-5,6,7,8-tetrahydro-2-naphthalenyl)-4,5,6,7-tetrahydro-1-benzofuran]-2-(2,4-thiazolidinedione).

A toluene solution (10 mL) was mixed with 4-(5,5,8,8-tetramethyl-5,6,7,8-tetrahydro-2-naphthalenyl)-4,5,6,7-tetrahydro-1-benzofuran]-2-carboxaldehyde (100 mg, 0.30 mmol), 2,5-thiazolidinedione (62 mg, 0.53 mmol), morpholine (200 mg, 2.3 mmol), molecular sieves and 10 mL of anhydrous toluene. The reaction mixture was stirred at reflux for 4.0 hours at which time it was cooled to 0–5° C. The resulting yellow solid was filtered in vacuo and washed with 10 mL of cold toluene. The resulting solid was dried in vacuo for 17 hours to afford 34 mg of pure solid.

$^1$H NMR (CDCl₃) 400 MHz δ 7.95 (s, 1H), 7.50 (s, 1H), 7.22 (d, 1H), 7.02 (s, 1H), 6.83 (d, 1H), 6.50 (s, 1H), 3.82 (t, 1H), 2.81–2.77 (m, 2H), 2.18–1.99 (m, 2H), 1.90–1.80 (m, 1H), 1.79–1.60 (m, 5H), 1.35–1.20 (m, 12H) ppm.

Example 15

[4-(5,5,8,8,-Tetramethyl-5,6,7,8-tetrahydro-2-naphthalenyl)-4,5,6,7-tetrahydro-1-benzothien-2-yl]-2-propionic acid A. [4-(5,5,8,8-Tetramethyl-5,6,7,8-tetrahydro-2-naphthalenyl)-4,5,6,7-tetrahydro-1-benzothien]-2-propionic acid A solution was made containing EtOAc (20 mL), [4-(5,5,8,8-tetramethyl-5,6,7,8-tetrahydro-2-naphthalenyl)-4,5,6,7-tetrahydro-1-benzothien]-2-trans-propenoic acid (200 mg, 0.51 mmol) and Pearlman's catalyst (50 mg). The reaction mixture was degassed in vacuo and stirred under a hydrogen atmosphere (1 atm) for a period of 2.0 hours. The reaction mixture was degassed and filtered over celite in vacuo. The resulting solution was concentrated to dryness in vacuo. The resulting oil was dissolved into Et₂O and washed with saturated NaCl. The organics were dried (MgSO₄) and concentrated to afford 176 mg of desired acid. $^1$H NMR (CDCl₃) 400 MHz δ 7.20 (d, 1H), 7.00 (s, 1H), 6.80 (d, 1H), 6.13 (s, 1H), 3.82 (m, 1H), 3.00 (t, 2H), 2.80 (m, 2H), 2.61 (t, 2H), 2.17–2.03 (m, 1H), 1.97–1.80 (m, 1H), 1.78–1.62 (m, 6H), 1.30–1.17 (m, 12H) ppm.

Example 16

4-(5,5,8,8,-Tetramethyl-5,6,7,8-tetrahydro-2-naphthalenyl)-4,5,6,7-tetrahydro-1-benzofuran]-2-(2,3 (cis)propenoic acid A. 4-(5,5,8,8-Tetramethyl-5,6,7,8-tetrahydro-2-naphthalenyl)-4,5,6,7-tetrahydro-1-benzofuran]-2-acetophenone A flame dried round bottom flask was charged with 4-(5,5,8,8-tetramethyl-5,6,7,8-tetrahydro-2-naphthalenyl)-

4,5,6,7-tetrahydro-1-benzofuran]-2-carboxaldehyde (500 mg, 1.6 mmol) and anhydrous ether (25 mL). This solution was cooled to −70° C. while stirring under a nitrogen blanket. To this solution was added 2.5 M t-butyl lithium (1.0 mL, 2.4 mmol). The reaction mixture was allowed to stir for 30 minutes at which time it was quenched via the addition of N-methoxy-N-methylacetamide (330 mg, 3.2 mmol). The reaction was allowed to warm to RT where it stirred for 4.0 hours followed by quenching via the addition of 1.0 N HCl (20 mL). The reaction mixture was extracted using ether. The organics were separated and dried over $MgSO_4$ followed by concentrating to dryness. The resulting oil was chromatographed on silica gel (90% hexanes/10% ethyl acetate) to afford 487 mg of pure oil.

$^1$H NMR ($CDCl_3$) 400 MHz δ 7.30 (d, 1H), 7.24 (s, 1H), 7.00 (dd, 1H), 6.95 (s, 1H), 3.80 (m, 2H), 2.87(m, 2H), 2.40 (s, 3H), 2.18–2.05 (m, 2H), 1.90–1.80 (m, 1H), 1.79–1.60 (m, 5H), 1.30–1.20 (m, 12H) ppm.

B. 4-(5,5,8,8-Tetramethyl-5,6,7,8-tetrahydro-2-naphthalenyl)-4,5,6,7-tetrahydro-1-benzofuran]-2-(2,3 (cis)propenoic acid.

To a THF solution (20 mL) containing sodium hydride (138 mg, 5.5 mmol, 95%) was added triethylphosphonoacetate (245 mg, 2.1 mmol) at 0–5° C. To this reaction mixture was added 4-(5,5,8,8-tetramethyl-5,6,7,8-tetrahydro-2-naphthalenyl)-4,5,6,7-tetrahydro-1-benzofuran]-2-acetophenone (480 mg, 1.4 mmol) and the mixture was allowed to warm to RT. The reaction mixture was stirred at RT for 1.0 hour at which time it was quenched via the addition of water (30 mL). The mixture was stirred at RT for 16 hours. The resulting mixture was made acidic using 3.0 N HCl. The reaction mixture was then extracted into ether and dried over $MgSO_4$. The mixture was concentrated to dryness and chromatographed on silica gel (80% hexanes/20% EtOAc) yielding 45 mg of pure acid.

$^1$H NMR ($CDCl_3$) 400 MHz δ 7.20 (d, 1H), 7.07 (s, 1H), 6.98 (s, 1H), 6.89 (d, 1H), 6.06 (s, 1H), 3.82(m, 1H), 2.65 (m, 2H), 2.20 (s, 3H), 2.16–2.06 (m, 1H), 1.97–1.90 (m, 1H), 1.82–1.73 (m, 1H), 1.71–1.62 (m, 5H), 1.30–1.20 (m, 12H) ppm.

Example 17

(2E)-3-{4-[(5,5,8,8-Tetramethyl-5,6,7,8-tetrahydro-2-naphthalenyl)methyl]-2-furyl}-2-propenoic acid

A. 2-(4-Bromo-2-furyl)-1,3-dioxolane

A toluene solution (100 mL) containing, p-toluenesulphonic acid monohydrate (100 mg, 0.52 mmol), 4-bromo-2-furaldehyde (5.0 g, 28.6 mmol) and ethylene glycol (1.7 g, 28.6 mmol) was heated at reflux for a period of 4.0 hours. The reaction flask was fitted with a Dean-Stark trap to collect the water. After 4.0 hours the reaction mixture was concentrated to dryness and partitioned between saturated $NaHCO_3$ and ethyl ether. The solvent was dried over $MgSO_4$ and concentrated to dryness to yield a total 4.9 g (79% yield) of compound A.

$^1$H NMR ($CDCl_3$) 400 MHz δ 7.42 (s, 1H), 6.50 (s, 1H), 5.91 (s, 1H), 4.17–3.98 (m, 4H) ppm.

B. 5,5,8,8-Tetramethyl-5,6,7,8-tetrahydro-2-naphthalenecarbaldehyde

A flame dried round bottom flask was charged with 6-bromo-1,1,4,4-tetramethyl-1,2,3,4-tetrahydronaphtalene (10 g, 37 mmol) and anhydrous THF (100 mL). This solution was cooled to −70° C. while stirring under a nitrogen blanket. To this solution was added 2.5 M n-butyl lithium (14.9 mL, 37 mmol). The reaction mixture was allowed to stir for 30 minutes at which time it was quenched via the addition of dimethylformamide (5.0 mL). The reaction was allowed to warm to RT where it stirred for 17 hours. The reaction was quenched by the addition of 1.0 N HCl (100 mL). The reaction mixture was extracted using ether. The organics were separated and dried over $MgSO_4$ followed by concentrating to dryness. The resulting oil was dried under high vacuum to give a total of 8.2 g (100%) of crude oil. The product was used without further purification.

$^1$H NMR ($CDCl_3$) 400 MHz δ 9.95 (s, 1H), 7.82 (s, 1H), 7.61 (d, 1H), 7.46 (d, 1H), 1.74–1.67 (m, 4H), 1.41–1.20 (m, 12H) ppm.

C. [5-(1,3-Dioxolan-2-yl)-3-furyl](5,5,8,8-tetramethyl-5,6,7,8-tetrahydro-2-naphthalenyl) methanol A mixture of 2-(4-bromo-2-furyl)-1,3-dioxolane (2.4 g, 11 mmol) and anhydrous THF (30 mL) was added to a flame dried round bottom flask and cooled to −70° C. To this mixture was added 2.5 M n-butyl lithium (4.9 mL, 12.3 mmol) and the mixture stirred at −70° C. for 1.0 hour. To this mixture was added 5,5,8,8-tetramethyl-5,6,7,8-tetrahydro-2-naphthalenecarbaldehyde (2.4 g, 11 mmol) and the reaction was allowed to stir at 0° C. for 3.0 hours. The reaction mixture was mixed with 1.0 N HCl while at 0° C. and partitioned with ether. The ether was separated and dried with $MgSO_4$. The solvent was evaporated in vacuo to give a crude oil that was chromatographed using silica gel (95% hexanes/5% EtOAc) to afford 1.1 g of compound C.

$^1$H NMR ($CDCl_3$) 400 MHz δ 7.36–7.24 (m, 3H), 7.10 (d, 1H), 6.41 (s, 1H), 5.85 (s, 1H), 5.30 (s, 1H), 4.17–3.98 (m, 4H), 1.70 (s, 4H), 1.25 (s, 12H) ppm.

D. 2-{4-[(5,5,8,8-Tetramethyl-5,6,7,8-tetrahydro-2-naphthalenyl)methyl]-2-furyl}-1,3-dioxolane A flask was mixed with [5-(1,3-dioxolan-2-yl)-3-furyl](5,5,8,8-tetramethyl-5,6,7,8-tetrahydro-2-naphthalenyl)methanol (1.1 g, 3.1 mmol), phenylchlorothionoformate (586 mg, 3.4 mmol), dimethylaminopyridine (25 mg, 0.205 mmol) and anhydrous $CH_2Cl_2$ (25 mL). This solution was allowed to stir at RT for 1.0 hour and concentrated to dryness. This crude reaction mixture was dissolved in toluene (50 mL). This toluene solution was mixed with $Bu_3SnH$ (2.7 g, 9.3 mmol) and AIBN (10 mg, 0.061 mmol). The solution stirred at reflux for a period of 4.0 hours and was concentrated to dryness. The resulting crude was partitioned between saturated $NaHCO_3$ and $CH_2Cl_2$. The organics were dried over $MgSO_4$ and concentrated to afford a crude oil. This oil was chromatographed on silica gel (95% hexanes/5% EtOAc) to afford 246 mg of compound D.

$^1$H NMR ($CDCl_3$) 400 MHz δ 7.22–7.16 (m, 3H), 6.93 (d, 1H), 6.32 (s, 1H), 5.84 (s, 1H), 4.17–3.98 (m, 4H), 3.64 (s, 2H), 1.63 (s, 4H), 1.25 (s, 12H) ppm.

E. 4-[(5,5,8,8-Tetramethyl-5,6,7,8-tetrahydro-2-naphthalenyl)methyl]-2-furaldehyde A round bottom flask was mixed with 2-{4-[(5,5,8,8-tetramethyl-5,6,7,8-tetrahydro- 2-naphthalenyl)methyl]-2-furyl}-1,3-dioxolane (246 mg, 0.72 mmol), 3.0 N HCl (10 mL) and THF (20 mL). The reaction mixture stirred for 16 hours at room temperature and was concentrated to one half volume. The resulting mixture was partitioned between saturated NaCl and ether. The ether layer was dried over $MgSO_4$ and concentrated to dryness. The resulting oil showed an inseparable impurity by TLC and the product was used without further purification.

F. Ethyl (2E)-3-{4-[(5,5,8,8-tetramethyl-5,6,7,8-tetrahydro-2-naphthalenyl)methyl]-2-furyl}-2-propenoate A flame dried round bottom flask was charged with anhydrous THF (15 mL) and sodium hydride (3.4 mg, 1.4 mmol). The solution was cooled to 0–5° C. and mixed with triethylphosphonoacetate (314 mg, 1.4 mmol). The reaction was stirred for 30 minutes at 0–5° C. To this mixture was added 4-[(5,5,8,8-tetramethyl-5,6,7,8-tetrahydro-2-naphthalenyl)methyl]-2-furaldehyde (222 mg, 0.71 mmol) and the reaction stirred at RT for 16 hours. The reaction was quenched with water and made acidic using 1.0 N HCl. The reaction mixture was partitioned between water and ethyl acetate and the organics were dried over $MgSO_4$. The organics were concentrated and the resulting oil was chromatographed on silica gel (95% hexanes/5% EtOAc). The resulting pure compound F (76 mg) was used without further purification.

$^1$H NMR (CDCl$_3$) 400 MHz δ 7.37 (d, 1H), 7.30–7.20 (m, 2H), 6.99–6.89 (m, 2H), 6.47 (s, 1H), 6.23 (d, 1H), 4.22 (q, 2H), 3.70 (s, 2H), 1.65 (s, 4H), 1.42 (s, 6H), 1.38–1.18 (m, 9H) ppm.

G. (2E)-3-{4-[(5,5,8,8-Tetramethyl-5,6,7,8-tetrahydro-2-naphthalenyl)methyl]-2-furyl}-2-propenoic acid A mixture containing ethyl (2E)-3-{4-[(5,5,8,8-tetramethyl-5,6,7,8-tetrahydro-2-naphthalenyl) methyl]-2-furyl}-2-propenoate (76 mg, 0.21 mmol), methanol (1.0 mL), THF (2.0 mL) and 5.0 N NaOH (5.0 mL) was allowed to stir at RT for a period of 16 hours. The reaction mixture was cooled to 0–5° C. and made acidic using concentrated HCl (pH 3.5). The mixture was extracted with EtOAc, dried over $MgSO_4$, and concentrated to dryness to afford a crude solid. The resulting solid was chromatographed on silica gel (90% hexanes/10% EtOAc) to give 15 mg of compound G.

$^1$H NMR (d$_6$-acetone) 400 MHz δ 7.51 (s, 1H), 7.38 (d, 1H), 7.26–7.22 (m, 2H), 6.98 (dd, 1H), 6.73 (s, 1H), 6.19 (d, 1H), 3.72 (s, 2H), 1.63 (s, 4H), 1.22 (m, 12H) ppm.

Example 18

(2E)-3-{4-[(5,5,8,8-Tetramethyl-5,6,7,8-tetrahydro-2-naphthalenyl)methyl]-2-thienyl}-2-propenoic acid

A. 2-(4-Bromo-2-thienyl)-1,3-dioxolane

A toluene solution (75 mL) containing, p-toluenesulphonic acid monohydrate (500 mg, 2.63 mmol), 4-bromo-2-thiophene carboxaldehyde (7.5 g, 40 mmol) and ethylene glycol (12.1 g, 0.20 mol) was heated at reflux for a period of 4.0 hours. The reaction flask was fitted with a Dean-Stark trap to collect the water. After 4.0 hours the reaction mixture was concentrated to dryness and partitioned between saturated $NaHCO_3$ and $CH_2Cl_2$. The solvent was dried over $MgSO_4$ and concentrated to dryness to yield a total 9.1 g (98% yield) of compound A.

$^1$H NMR (CDCl$_3$) 400 MHz δ 7.21 (s, 1H), 7.03 (s, 1H), 6.02 (s, 1H), 4.16–4.00 (m, 4H) ppm.

B. [5-(1,3-Dioxolan-2-yl)-3-thienyl](5,5,8,8-tetramethyl-5,6,7,8-tetrahydro-2-naphthalenyl)methanol 2-(4-Bromo-2-thienyl)-1,3-dioxolane (8.9 g, 38 mmol) and anhydrous THF (100 mL) was added to a flame dried round bottom flask and cooled to −70° C. To this mixture was added 2.5 M n-butyl lithium(16.8 mL, 45 mmol) and the mixture stirred at −70° C. for 1.0 hour. To this mixture was added 5,5,8,8-tetramethyl-5,6,7,8-tetrahydro-2-naphthalenecarbaldehyde (8.2 g, 38 mmol) and the reaction was allowed to stir at 0° C. for 16 hours. The reaction mixture was mixed with 6.0 N HCl (pH 7.0) while at 0° C. and partitioned with ether. The ether was separated and dried with $MgSO_4$. The solvent was evaporated in vacuo to give a crude oil that was chromatographed using silica gel (90% hexanes/10% EtOAc) to afford 5.8 g compound B.

hu 1H NMR (CDCl$_3$) 400 MHz δ 7.37 (d, 1H), 7.25 (d, 1H), 7.18 (s, 1H), 7.09 (s, 1H), 6.99 (s, 1H), 6.02 (m, 2H), 4.17–3.99 (m, 4H), 1.68 (s, 4H), 1.24 (s, 12H) ppm.

C. 2-{4-[(5,5,8,8-Tetramethyl-5,6,7,8-tetrahydro-2-naphthalenyl)methyl]-2-thienyl}-1,3-dioxolane A flask was mixed with [5-(1,3-dioxolan-2-yl)-3-thienyl] (5,5,8,8-tetramethyl-5,6,7,8-tetrahydro-2-naphthalenyl) methanol (4.0 g, 11 mmol), phenylchlorothionoformate (2.4 g, 17 mmol), dimethyaminopyridine (2.7 g, 22 mmol) and anhydrous $CH_2Cl_2$ (40 mL). This solution was allowed to stir at RT for 17 hours and concentrated to dryness. This crude mixture was partitioned between saturated $NaHCO_3$ and ether. The organics were dried over $MgSO_4$ and concentrated to dryness to afford 9.8 g of crude oil. The crude solid was dissolved in toluene (100 mL). This toluene solution was mixed with Bu$_3$SnH (10 mL, 37.1 mmol) and AIBN (100 mg, 0.61 mmol). The solution stirred at 80° C. for a period of 5.0 hours and was cooled to RT. This solution was charged with 3% $NH_4OH$ and stirred at RT for 1.0 hour. The organics were separated, dried over $MgSO_4$ and concentrated to afford a crude oil. This oil was chromatographed on silica gel (95% hexanes/5% EtOAc) to afford 5.1 g of compound C (the compound contained an inseparable impurity but was confirmed by LCMS).

D. 4-[(5,5,8,8-Tetramethyl-5,6,7,8-tetrahydro-2-naphthalenyl)methyl]-2-thiophenecarbaldehyde A round bottom flask was mixed with 2-{4-[(5,5,8,8-tetramethyl-5,6,7,8-tetrahydro-2-naphthalenyl)methyl]-2-thienyl}-1,3-dioxolane (5.1 g, 14.3 mmol), 3.0 N HCl (50 mL), methanol (20 mL) and THF (30 mL). The reaction mixture stirred for 6 hours at room temperature and was concentrated to one half volume. The resulting mixture was partitioned between water and ether. The ether layer was dried over $MgSO_4$ and concentrated to dryness. The resulting oil showed an inseparable impurity by TLC from the starting material. The product was used without further purification (2.7 g).

E. (2E)-3-{4-[(5,5,8,8-Tetramethyl-5,6,7,8-tetrahydro-2-naphthalenyl)methyl]-2-thienyl}-2-propenoic acid A flame dried round bottom flask was charged with anhydrous THF (25 mL) and sodium hydride (192 mg, 4.8 mmol). The solution was cooled to 0–5° C. and mixed with triethylphosphonoacetate (1.1 g, 4.8 mmol) and the reaction was stirred for 30 minutes at 0–5° C. To this mixture was added 4-[(5,5,8,8-tetramethyl-5,6,7,8-tetrahydro-2-naphthalenyl)methyl]-2-thiophenecarbaldehyde (500 mg, 1.6 mmol) and the reaction stirred at RT for 16 hours. The reaction was quenched with water at 0° C. and this mixture was mixed with 10 mL of 2.5 N NaOH and 3.0 mL of methanol. The reaction mixture was stirred at RT for an additional 2.0 hours and was made acidic using 1.0 N HCl. The mixture was extracted into ether and dried over $MgSO_4$. The organics were concentrated and the resulting oil was triturated with a mixture of ether/hexanes. The resulting solid was filtered and dried in vacuo to yield 281 mg of compound E.

$^1$H NMR ($CDCl_3$) 400 MHz δ 7.80 (d, 1H), 7.22 (d, 1H), 7.14 (m, 2H), 7.02 (s, 1H), 6.94 (d, 1H), 6.19 (d, 1H), 3.86 (s, 2H), 1.65 (s, 4H), 1.27 (s, 12H) ppm.

Example 19

(2E)-3-{4-[(3-Methoxy-5,5,8,8-tetramethyl-5,6,7,8-tetrahydro-2-naphthalenyl)methyl]-2-furyl}-2-propenoic acid

A. 3-Furyl(3-methoxy-5,5,8,8-tetramethyl-5,6,7,8-tetrahydro-2-naphthalenyl)methanol 6-Bromo-7-methoxy-1,1,4,4-tetramethyl-1,2,3,4-tetrahydronaphthalene (5.0 g, 17 mmol) and anhydrous THF (100 mL) was added to a flame dried round bottom flask and cooled to −70° C. To this mixture was added 2.7 M n-butyl lithium (6.9 mL, 18.5 mmol) and the mixture stirred at −70° C. for 1.0 hour. To this mixture was added 3-furaldehyde (1.61 g, 17 mmol) and the reaction was allowed to stir at 0° C. for 4.0 hours. The reaction mixture was mixed with 1.0 N HCl (pH 4.0) while at 0° C. and partitioned with ether. The ether was separated and dried with $MgSO_4$. The solvent was evaporated in vacuo to give a crude oil that was chromatographed using silica gel (90% hexanes/10% EtOAc) to afford 3.4 g of compound A.

$^1$H NMR ($CDCl_3$) 400 MHz δ 7.57 (s, 1H), 7.38 (s, 1H), 7.22 (s, 1H), 7.04 (s, 1H), 6.38 (s, 1H), 5.90 (d, 1H), 4.23 (d, 1H), 3.80 (s, 3H), 1.67–1.56 (m, 4H), 1.32–1.18 (m, 12H) ppm.

B. 4-[Hydroxy(3-methoxy-5,5,8,8-tetramethyl-5,6,7,8-tetrahydro-2-naphthalenyl)methyl]-2-furaldehyde A solution containing anhydrous ether (50 mL) and 3-furyl(3-methoxy-5,5,8,8-tetramethyl-5,6,7,8-tetrahydro-2-naphthalenyl)methanol (3.4 g, 10.8 mmol) was cooled to −70° C. while stirring under nitrogen. To this mixture was added 2.7 M t-butyllithium (12.0 mL, 32.4 mmol). The reaction mixture was allowed to stir at −40° C. for 30 minutes at which time it was charged with DMF (1.2 mg, 16.2 mmol). The reaction was stirred at −20° C. to 0° C. over a period of 30 minutes and the reaction was quenched using 1.0 N HCl. The reaction was extracted with ether followed by drying with $MgSO_4$. The organics were concentrated in vacuo to afford a crude oil. The oil was chromatographed on silica gel (90% hexanes/10% EtOAc) to yield 2.9 g of compound B as an oil.

$^1$H NMR ($CDCl_3$) 400 MHz δ 9.83 (s, 1H), 7.52 (s, 1H), 7.30 (s, 1H), 6.77 (s, 1H), 6.51 (s, 1H), 6.27 (d, 1H), 4.25 (d, 1H), 3.82 (s, 3H), 1.65 (s, 4H), 1.31–1.19 (m, 12H) ppm.

C. 4-[(3-Methoxy-5,5,8,8-tetramethyl-5,6,7,8-tetrahydro-2-naphthalenyl)methyl]-2-furaldehyde A solution containing 4-[hydroxy(3-methoxy-5,5,8,8-tetramethyl-5,6,7,8-tetrahydro-2-naphthalenyl)methyl]-2-furaldehyde (2.9 g, 8.5 mmol), triethylsilane (2.9 g, 25.4 mmol) and anhydrous methylene chloride (40 mL) was cooled to 0° C. To this mixture was added trifluoroacetic acid (~1.0 mL, 8.5 mmol) and the reaction was allowed to stir at RT for 16 hours. The reaction was quenched with saturated $NaHCO_3$ and the organics were separated and dried over $MgSO_4$. The resulting oil (2.5 g) was used without further purification.

$^1$H NMR ($CDCl_3$) 400 MHz δ 9.80 (s, 1H), 7.50 (s, 1H), 7.09 (s, 1H), 6.77 (s, 1H), 6.41 (s, 1H), 4.07 (s, 2H), 3.79 (s, 3H), 1.67 (s, 4H), 1.27 (s, 6H), 1.21 (s, 6H) ppm.

D. (2E)-3-{4-[(3-Methoxy-5,5,8,8-tetramethyl-5,6,7,8-tetrahydro-2-naphthalenyl)methyl]-2-furyl}-2-propenoic acid A flame dried round bottom flask was charged with anhydrous THF (25 mL) and sodium hydride (276 mg, 11.5 mmol). The solution was cooled to 0–5° C. and mixed with triethylphosphonoacetate (2.6 g, 11.5 mmol) and the reaction was stirred for 30 minutes at 0–5° C. To this mixture was added 4-[(3-methoxy-5,5,8,8-tetramethyl-5,6,7,8-tetrahydro-2-naphthalenyl)methyl]-2-furaldehyde (2.5 g, 7.65 mmol) and the reaction stirred at RT for 16 hours. The reaction was quenched with water at 0° C. and this mixture was mixed with 2.5 N NaOH and methanol. The reaction mixture was stirred at RT for an additional 2.0 hours and was made acidic using 1.0 N HCl. The mixture was extracted into ether and dried over $MgSO_4$. The organics were concentrated and the resulting oil was chromatographed on silica gel (90% hexanes/10% EtOAc). The resulting solid was filtered and dried in vacuo to yield 1.9 g of the ethyl ester as an oil and 238 mg of compound D.

$^1$H NMR ($CDCl_3$) 400 MHz δ 7.76 (d, 1H), 7.39 (s, 1H), 7.02 (s, 1H), 6.73 (s, 1H), 6.36 (s, 1H), 6.27 (d, 1H), 3.80 (s, 5H), 1.64 (s, 4H), 1.28–1.19 (d, 12H) ppm.

Example 20

(2E)-3-{5-(Methyl-4-[(5,5,8,8-tetramethyl-5,6,7,8-tetrahydro-2-naphthalenyl)methyl]-2-furyl}2-propenoic acid

A. N-methoxy-N-2-dimethyl-3-furamide

A solution of $CH_2Cl_2$ (200 mL) containing 2-methyl-3-furoic acid (20 g, 159 mmol), HOBt (23.5 g, 174 mmol), N-methyl-O-methoxyamine hydrochloride (17 g, 174 mmol) and EDC (30 g, 174 mmol) was mixed with triethylamine (17.6 g, 174 mmol) while maintaining a temperature less than 15° C. The reaction stirred at RT for 17 hours and was then concentrated to dryness. The reaction crude was partitioned between $CH_2Cl_2$ and saturated $NaHCO_3$. The organics were then washed with 0.5 N HCl and saturated NaCl. The organics were dried over $MgSO_4$ and concentrated to dryness. The resulting solid was used without further purification ¹H NMR (CDCl₃) 400 MHz δ 7.04 (s, 1H), 6.68 (s, 1H), 3.63 (s, 3H), 3.32 (s, 3H), 2.55 (s, 3H) ppm.

B. (2-Methyl-3-furyl)(5,5,8,8-tetramethyl-5,6,7,8-tetrahydro-2-naphthalenyl)methanone A solution containing 6-bromo-1,1,4,4-tetramethyl-1,2,3,4-tetrahydronaphthalene (10.0 g, 37 mmol) and THF (100 mL) was cooled to −70° C. The reaction was mixed with 2.7 M n-butyl lithium (15.2 mL, 41 mmol) and the reaction mixture was allowed to stir at −70° C. for a period of 30 minutes. This solution was mixed with N-methoxy-N-2-dimethyl-3-furamide (7.0 g, 41 mmol) and was slowly allowed to warm to RT over a period of 17 hours. The reaction mixture was quenched at 0° C. using 1.0 N HCl and then extracted with ether. The organics were washed with saturated NaCl, dried over MgSO₄ and concentrated to give a crude product. The crude oil was chromatographed on silica gel (90% hexanes/10% EtOAc) to yield 8.1 g of compound B as an oil that was mostly pure by NMR.

¹H NMR (CDCl₃) 400 MHz δ 7.78 (s, 1H), 7.58 (d, 1H), 7.39 (d, 1H), 7.22 (s, 1H), 6.60 (s, 1H), 2.57 (s, 3H), 1.65 (s, 4H), 1.32 (s, 12H) ppm.

C. (2-Methyl-3-furyl)(5,5,8,8-tetramethyl-5,6,7,8-tetrahydro-2-naphthalenyl)methanol A solution containing (2-methyl-3-furyl)(5,5,8,8-tetramethyl-5,6,7,8-tetrahydro-2-naphthalenyl)methanol (8.0 g, 27 mmol) and dry methanol (100 mL) was cooled to 0–5° C. using an ice bath. The reaction was mixed with NaBH₄ (2.0 g, 54 mmol) and allowed to stir at RT for a period of 16 hours. The reaction mixture was slowly made acidic using concentrated HCl. The resulting reaction mixture was partitioned between ether and water. The organics were dried over MgSO₄ and concentrated to dryness. The crude oil was chromatographed on silica gel (90% hexanes/10% EtOAc) to give 6.6 g of compound C as an oil.

¹H NMR (CDCl₃) 400 MHz δ 7.35 (s, 1H), 7.27 (d, 1H), 7.23 (s, 1H), 7.11 (d, 1H), 6.19 (s, 1H), 5.71 (d, 1H), 2.29 (s, 3H), 1.96 (d, 1H), 1.63 (s, 4H), 1.23 (s, 12H) ppm.

D. 4-[Hydroxy(5,5,8,8-tetramethyl-5,6,7,8-tetrahydro-2-naphthalenyl)methyl]-5-methyl-2-furaldehyde A solution containing anhydrous ether (70 mL) and (2-methyl-3-furyl)(5,5,8,8-tetramethyl-5,6,7,8-tetrahydro-2-naphthalenyl)methanol (6.6 g, 22 mmol) was cooled to −70° C. while stirring under nitrogen. To this mixture was added 2.7 M t-butyllithium (20 mL, 54 mmol). The reaction mixture was allowed to stir at −70° C. for 30 minutes at which time it was charged with DMF (2.4 g, 33 mmol). The reaction was stirred at 0° C. over a period of 1.0 hour and the reaction was quenched using 1.0 N HCl. The reaction was extracted with ether followed by drying with MgSO₄. The organics were concentrated in vacuo to afford a crude oil. The oil was chromatographed on silica gel (90% hexanes/10% EtOAc) to yield 4.1 g of compound D as an oil.

hu 1H NMR (CDCl₃) 400 MHz δ 9.45 (s, 1H), 7.32 (m, 2H), 7.15 (s, 1H), 7.15 (d, 1H), 5.74 (d, 1H), 2.40 (s, 3H), 2.09 (d, 1H), 1.68 (s, 4H), 1.27 (s, 12H) ppm.

E. 5-Methyl-4-[(5,5,8,8-tetramethyl-5,6,7,8-tetrahydro-2-naphthalenyl)methyl]-2-furaldehyde A solution containing 4-[hydroxy-(5,5,8,8-tetramethyl-5,6,7,8-tetrahydro-2-naphthalenyl)methyl]-5-methyl-2-furaldehyde (3.6 g, 11 mmol), triethylsilane (3.8 g, 33.1 mmol) and anhydrous methylene chloride (50 mL) was cooled to 0° C. To this mixture was added trifluoroacetic acid (~1.3 g, 11.4 mmol) and the reaction was allowed to stir at RT for 16 hours. The reaction was quenched with saturated NaHCO₃ and the organics were separated and dried over MgSO₄. The resulting oil was used without further purification (the product appears to quickly decompose).

F. (2E)-3-{5-Methyl-4-[(5,5,8,8-tetramethyl-5,6,7,8-tetrahydro-2-naphthalenyl)methyl]-2-furyl}-2-propenoic acid A flame dried round bottom flask was charged with anhydrous THF (20 mL) and sodium hydride (772 mg, 32.2 mmol). The solution was cooled to 0–5° C. and mixed with triethylphosphonoacetate (794 mg, 35.2 mmol) and the reaction was stirred for 30 minutes at 0–5° C. To this mixture was added 5-methyl-4-[(5,5,8,8-tetramethyl-5,6,7,8-tetrahydro-2-naphthalenyl)methyl]-2-furaldehyde (1.0 g, 32.2 mmol) and the reaction stirred at RT for 4 hours. The reaction was quenched with water at 0° C. while maintaining a temperature of less than 15° C. and this mixture was stirred at RT overnight. The reaction mixture was made acidic using concentrated HCl. The mixture was partitioned between ether and water and dried over MgSO₄. The oily solid was triturated with hexanes and the resulting solid was filtered and dried in vacuo to yield 254 mg of compound E.

¹H NMR (d₆-acetone) 400 MHz δ 7.32 (d, 1H), 7.24–7.18 (m, 2H), 6.93 (d, 1H), 6.63 (s, 1H), 6.11 (d, 1H), 3.65 (s, 2H), 2.36 (s, 3H), 1.63 (s, 4H), 1.22 (s, 12H) ppm.

Example 21

(2E)-3-{4-[7-Dimethylamino)-1-methyl-2,3-dihydro-1H-indol-5-yl]-4,5,6,7-tetrahydro-1-benzofuran-2-yl}prop-2-enoic acid

A. 5-Bromoindol-7-amine

An EtOH solution (300 mL) containing 5-bromo-7-nitroindoline (5.44 g, 22.4 mmol) and tin(II)chloride dihydrate (25.2 g, 111.9 mmol) was immersed in an oil bath which had been preheated to 70° C. The resulting orange solution which turned black within 15 min stirred for 22 hr. It was then diluted with sat. NaHCO₃ and H₂O. The organics were extracted with EtOAc (3×), dried (MgSO₄) and the solvent removed in vacuo. The residual dark solid was purified via column chromatography (CH₂Cl₂/MeOH (19:1)) yielding 3.99 g (18.7 mmol, 84% yield) of compound A.

¹H NMR (CDCl₃) 400 MHz δ 6.76 (s, 1H), 6.61 (d, 1H, J=1.3 Hz), 3.54 (t, 2H, J=8.6 Hz), 3.52 (s(br), 3H), 3.01 (t, 2H, J=8.5 Hz) ppm.

B. 5-Bromo-N,N 1-trimethylindolin-7-amine

To a 37% aqeous formaldehyde solution (26.2 mL) containing 21.0 mL of a 3.0 M aqueous H₂SO₄ solution (63 mmol) cooled to 0° C. was added, via pipet, a THF solution (90 mL) containing compound A (1.18 g, 5.54 mmol) and sodium borohydride (8.81 g, 236 mmol) portionwise (caution: rapid gas evolution). Upon complete addition the reaction stirred at RT for 1 hr. The reaction was quenched with MeOH and H₂O. The resulting solution was basified with 2.0 M NaOH and the organics extracted with EtOAc. After drying over MgSO₄ the solvent was removed in vacuo and the residual dark oil purified via column chromatography (hexanes/EtOAc (9:1)) yielding 850 mg (3.33 mmol, 60% yield) of compound B as a clear liquid.

hu 1H NMR (CDCl$_3$) 400 MHz δ 6.86 (s, 1H), 6.81 (s, 1H), 3.27 (t, 2H, J=8.7 Hz), 2.88 (t, 2H, J=8.7 Hz), 2.82 (s, 3H), 2.61 (s, 6H) ppm.

C. N,N 1-Trimethyl-5-(4,5,6,7-tetrahydro-1-benzofuran-4-yl)indolin-7-amine

To a THF solution (20 mL) containing compound B (1.96 g, 7.70 mmol) cooled to −78° C. was added 3.3 mL of a 2.5 M hexanes solution of n-BuLi (8.31 mmol). The resulting solution stirred for 20 min at which time 6,7-dihydro-4(5H)-benzofuranone (1.42 g, 10.5 mmol) in 10 mL THF was added. The reaction stirred an additional 45 min and was then quenched with H$_2$O. Upon warming the solution was poured into additional H$_2$O and the organics extracted with Et$_2$O. After drying over MgSO$_4$ the solvent was removed in vacuo and the residual yellow oil was dissolved in THF (5 mL). This solution was then added to a THF solution (40 mL) containing sodium borohydride (3.97 g, 105 mmol) and BF$_3$.Et$_2$O (22.4 g, 157.5 mmol) at 0° C. After 5 min the white slurry was carefully poured into sat. NaHCO$_3$. The two phase solution was then extracted with Et$_2$O (2×), dried (MgSO$_4$) and the solvent removed in vacuo. The residual orange oil was purified via column chromatography (hexanes/EtOAc (15:1)) yielding 1.29 g of compound C mixed with what appeared to be des-bromo starting material. The mixture was taken on to the following step.

D. 4-[7-(Dimethylamino)-1-methyl-2,3-dihydro-1 H-indol-5-yl]-4,5,6,7-tetrahydro-1-benzofuran-2-carboxaldehyde To a Et$_2$O solution (15 mL) containing compound C (~1.3 g, 4.39 mmol) cooled to −40° C. was added 4.65 mL of a 1.7 M pentane solution of t-BuLi (7.91 mmol). The resulting orange solution stirred for 30 min when DMF (578 mg, 7.90 mmol) was added. The reaction was slowly allowed to warm to −20° C. over 30 min and was then quenched with H$_2$O. The solution was poured into additional H$_2$O and the organics extracted with Et$_2$O (2×). After drying over MgSO$_4$ the solvent was removed in vacuo and the residual oil purified via column chromatography (hexanes/EtOAc (4:1)) yielding 620 mg (1.92 mmol) of compound D.

$^1$H NMR (CDCl$_3$) 400 MHz δ 9.43 (s, 1H), 6.91 (s, 1H), 6.50 (s, 2H), 3.76 (m, 1H), 3.32–3.24 (m, 2H), 2.91–2.84 (m, 5H), 2.76–2.66 (m, 2H), 2.61 (s, 6H), 2.11–1.98 (m, 2H), 1.82–1.66 (m, 2H) ppm.

E. Ethyl (2E)-3-{4-[7-(dimethylamino)-1-methyl-2, 3-dihydro-1H-indol-5-yl]-4,5,6,7-tetrahydro-1-benzofuran-2-yl}prop-2-enoate To a DME solution (5 mL) containing sodium hydride (113 mg, 2.84 mmol, 60% dispersion in mineral oil) was added triethylphosphonoacetate (636 mg, 2.84 mmol) at RT. After 5 min compound D (612 mg, 1.89 mmol) in 6 mL DME was added. The yellow reaction stirred for 30 min at RT and was then quenched with H$_2$O. The solution was poured into additional H2O and the organics extracted with Et2O. After drying over MgSO$_4$ the solvent was removed in vacuo and the residual oil purified via column chromatography (hexanes/EtOAc (8:1)) yielding 578 mg (1.47 mmol, 78% yield) of compound E as a yellow solid solid which was immediately taken into the next step.

F. (2E)-3-{4-[7-Dimethylamino)-1-methyl-2,3-dihydro-1H-indol-5-yl]-4,5,6,7-tetrahydro-1-benzofuran-2-yl}prop-2-enoic acid To a dioxane solution (7 mL) containing compound E (570 mg, 1.45 mmol) and 3 mL H$_2$O was added lithium hydroxide hydrate (608 mg, 14.5 mmol) at RT. The resulting solution stirred for 24 hr and was then quenched with sat. NaHSO$_4$. The organics were extracted with EtOAc and the aqueous layer basified tp pH 7. It was then extracted with EtOAc and the combined organic layers dried (MgSO$_4$). Removal of the solvent in vacuo and purification via column chromatography (CH$_2$Cl$_2$/MeOH (15:1)) yieldied 462 mg (1.26 mmol, 87% yield) of compound F, m.p. 105–108° C.

$^1$H NMR (CDCl$_3$) 400 MHz δ 7.37 (d, 1H, J=15.6 Hz), 6.52 (s, 2H), 6.35 (s, 1H), 6.18 (d, 1H, J=15.5 Hz), 3.72 (m, 1H), 3.29–3.24 (m, 2H), 2.88–2.83 (m, 5H), 2.72–2.65 (m, 2H), 2.61 (s, 6H), 2.07–1.95 (m, 2H), 1.77–1.62 (m, 2H) ppm.

Example 22

(2E)-3-[4-butyl-4-(5,5,8,8-tetramethyl-5,6,7,8-tetrahydronaphthalen-2-yl)-4,5,6,7-tetrahydro-1-benzofuran-2-yl]prop-2-enoic acid

A. N-methoxy-N-methylpentanamide

To a CH$_2$Cl$_2$ solution (200 mL) containing N-methoxy-N-methylamine hydrochloride (8.09 g, 82.9 mmol) and Et$_3$N (12.6 g, 124 mmol) was added valeryl chloride (10 g, 82.9 mmol) dropwise at room temperature. The resulting solution bubbled vigorously and stirred for 2 hours after which time it was carefully quenched with H$_2$O. The organic layer was separated and washed with 2.0 N NaOH. The organics were extracted with CH$_2$Cl$_2$, dried (MgSO$_4$) and the solvent removed in vacuo. The resulting colorless oil was taken on without further purification.

$^1$H NMR (CDCl$_3$) 400 MHz δ 3.62 (s, 3H), 3.12 (s, 3H), 2.38–2.34 (m, 2H), 1.60–1.52 (m, 2H), 1.36–1.26 (m, 2H), 0.90 (t, 3H, J=7.8 Hz) ppm.

B. 1-(5,5,8,8-Tetramethyl-5,6,7,8-tetrahydronaphthalen-2-yl)pentan-1-one

To a THF solution (30 mL) containing 5,6,7,8-tetrahydro-5,5,8,8-tetramethyl-2-bromonaphthalene (8.87 g, 33.2 mmol) cooled to −78° C. was added n-BuLi (14.7 mL, 39.8 mmol) dropwise. After stirring for 30 min at −78° C. a solution of A (3.7 g, 25.5 mmol) in THF (5 mL) was added dropwise. The reaction ran overnight and was quenched with the dropwise addition of H$_2$O. The organics were extracted with Et$_2$O, dried over MgSO$_4$ and the solvent reduced in vacuo. The residual brown oil was then purified via column chromatography (4% EtOAc/hexanes) yielding 1.12 g (4.30 mmol, 17% yield) of compound B as a colorless oil.

$^1$H NMR (CDCl$_3$) 400 MHz δ 7.91 s, 1H), 7.68 (d, 1H, J=6.4 Hz), 7.36 (d, 1H, J=8.3 Hz), 2.92 (t, 2H, J=7.4 Hz), 1.72–1.64 (m, 6H), 1.41–1.36 (m, 2H), 1.29–1.22 (m, 12H), 0.95 (t, 3H, J=7.4 Hz) ppm.

C. 1-(2-Furyl)-4-(5,5,8,8-tetramethyl-5,6,7,8-tetrahydronaphthalen-2-yl)octan-4-ol To a dry round bottom flask was added anhydrous THF (50 mL), magnesium turnings (1.0 g, 0.0417 moles) and 2-(3-bromopropyl)furan (2.8 g, 0.0148 moles; prepared as described in: *J. Org. Chem.* 1994, 59, 23, incorporated herein by reference as related to such preparation). This solution was cooled to 0–5° C. using an ice bath and the reaction mixture was mixed with NaH (1.8 g, 0.074 moles). The magnesium turnings were agitated until the Grignard salt began to form. The formation was allowed to proceed for a period of 1.0 hour. At this time the reaction mixture was mixed with a THF solution (25 mL) of compound B (3.5 g, 0.0129 moles). The reaction was allowed to warm to RT over a period of 1.0 hour and was then cooled to 0–5° C. The reaction was slowly quenched with water. The aqueous mixture was neutralized (pH 7.0) with dilute HCl and extracted with ether. The organics were dried over $MgSO_4$ and concentrated to afford a crude oil. The oil was purified using silica gel chromatography (90% hexanes/10% EtOAc) to yield a total of 2.6 g of pure oil (53%).

$^1$H NMR ($CDCl_3$) 400 MHz δ 7.27–7.18 (m, 3H), 7.03 (d, 1H, J=8.0 Hz), 6.22 (d, 1H, J=1.7 Hz), 5.87 (d, 1H, J=1.7 Hz), 2.59–2.48 (m, 2H), 1.86–1.38 (m, 12H), 1.31–0.99 (m, 14H), 0.85 (t, 3H, J=7.8 Hz) ppm.

D. 4-Butyl-4-(5,5,8,8-tetramethyl-5,6,7,8-tetrahydronaphthalen-2-yl)-4,5,6,7-tetrahydro-1-benzofuran To a round bottom flask was added anhydrous $CH_2Cl_2$ (50 mL) and compound C (2.6 g, 0.0068 moles). This solution was cooled to 0–5° C. using an ice bath and the reaction mixture was mixed dropwise with TFA (852 μL, 0.074 moles). The reaction was allowed to stir at 0–5° C. for 30 minutes followed by quenching with saturated $NaHCO_3$. The reaction was washed with $NaHCO_3$ and the organics were dried over $MgSO_4$. The organics were concentrated to dryness to afford a crude oil. The oil was purified using silica gel chromatography (90% hexanes/10% EtOAc) to yield a total of 2.6 g of pure oil (56%).

$^1$H NMR ($CDCl_3$) 400 MHz δ 7.30 (s, 1H), 7.12 (d, 1H, J=8.4 Hz), 7.04 (s, 1H, J=1.7 Hz), 6.91 (dd, 1H, J=8.4 Hz), 6.23 (d, 1H, J=1.8 Hz), 2.48–2.60 (m, 2H), 1.94–1.71 (m, 6H), 1.68–1.51 (m, 6H), 1.36–1.03 (m, 14H), 0.82 (t, 3H, J=7.4 Hz) ppm.

E. 4-Butyl-4-(5,5,8,8-tetramethyl-5,6,7,8-tetrahydronaphthalen-2-yl)4,5,6,7-tetrahydro-1-benzofuran-2-carbaldehyde A solution containing anhydrous ether (50 mL) and compound D (2.6 g, 0.0071 moles) was cooled to −70° C. while stirring under nitrogen. To this mixture was added 2.7 M t-BuLi (7.1 mL, 0.0178 moles). The reaction mixture was allowed to stir at −70 to −40° C. for 30 minutes at which time it was mixed with DMF (1.2 g, 0.0162 moles). The reaction was stirred at −20° C. to 0° C. over a period of 1.0 hour and the reaction was quenched using 1.0 N HCl. The reaction was extracted with ether followed by drying with $MgSO_4$. The organics were concentrated in vacuo to afford a crude oil. The oil was chromatographed on silica gel (90% hexanes/10% EtOAc) to yield 2.9 g of oil. The reaction product had inseparable impurities by TLC and the product was used without purification.

F. (2E)-3-[4-Butyl-4-(5,5,8,8-tetramethyl-5,6,7,8-tetrahydronaphthalen-2-yl)-4,5,6,7-tetrahydro-1-benzofuran-2-yl]prop-2-enoic acid To a THF solution (20 mL) containing sodium hydride (239 mg, 0.0095 moles, 95%) was added triethylphosphonoacetate (424 mg, 0.00189 moles) at 0–5° C. To this reaction mixture was added compound E (500 mg, 0.00126 moles) and the mixture was allowed to warm to RT. The reaction mixture was stirred at RT for 1.0 hour at which time it was quenched via the addition of water (30 mL). The reaction was mixed with NaOH (25 mL) and stirred at RT for 16 hours. The resulting mixture was made acidic using 3.0 N HCl. The reaction mixture was then extracted into ether and dried over $MgSO_4$. The mixture was concentrated to dryness and chromatographed on silica gel (80% hexanes/20% EtOAc) yielding 51 mg of pure acid.

$^1$H NMR ($CDCl_3$) 400 MHz δ 7.46 (d, 1H, J=15.4 Hz), 7.13 (d, 1H, J=8.4 Hz), 7.04 (s, 1H), 6.86 (dd, 1H, J=8.4 Hz), 6.54 (s, 1H), 6.23 (d, 1H, J=15.4 Hz), 2.64–2.58 (m, 2H), 1.96–1.77 (m, 5H), 1.63–1.51 (m, 5H), 1.33–1.03 (m, 14H), 0.82 (t3H, J=7.4 Hz) ppm.

Experimentals

The above-referenced examples were subjected to the following assay to identify inhibition and selectivity of the compounds of the present invention, with the results as detailed below:

Binding Assay

The compounds were tested for their ability to bind to hRXRα using a Scintillation Proximity Assay (SPA) as is known in the art. The RXRα ligand binding domain (LBD) was expressed in *E. coli* as an amino-terminal polyhistidine tagged fusion protein. The LBD was then labeled with biotin and immobilized on streptavidin-modified scintillation proximity beads.

9-cis[3H]-Retinoic acid (9-cis) was the radioligand used for the assay. To each well to be assayed was added the desired concentration of the previously prepared solution of 9-cis previously incubated with receptor-coated SPA bead slurry. The plates were incubated for at least 1 hour at room temperature and bound radioactivity for each well was determined in a Wallac 1450 Microbeta counter.

In this specification, pKi=−log of the concentration of the test compound required to achieve an apparent Ki value according to the equation $Ki=IC_{50}/1+[L]/K_d$, where $IC_{50}$=the concentration of test compound required to inhibit 50% of the specific binding of the radioligand, [L] is the concentration of the radioligand used, and $K_d$ is the dissociation constant for the radioligand at the receptor.

Apparent pKi values were >6.0 for all examples with the exception of Examples 13, 18, and 19, which each had a pKi<6.0.

Transient Transfection Assay

Transcriptional activity of the compounds was measured in a monkey kidney cell line (CV-1). These cells were transfected with full length human RXRα and the natural response element, cellular retinol binding protein type II in a reporter gene construct, (CRBP II-tk-SPAP), consisting of HSV tk promoter, and the secreted placental alkaline phosphatase reporter gene. CV-1 cells were plated at a density of 24,000 cells per well in high glucose DMEM supplemented with 10% charcoal/dextran-treated FBS. Transfection mixes contained 4 ng of receptor expression vector, 8 ng of reporter plasmid, 25 ng of β-galactosidase expression vector (used as an internal control), and 43 ng of carrier plasmid. Transfections were performed with Lipofectamine according to the manufacturer's instructions. Drug dilutions were prepared in phenol red-free DMEM/F-12 with 15 mM HEPES supplemented with 10% charcoal-stripped, delipidated calf serum.

Cells were incubated for 24 h in the presence of drugs, after which the medium was sampled and assayed for SPAP activity.

B-galactosidase, which measures transfection efficiency activity, was determined by using 3.6 mM o-nitrophenyl-D-galactopyranoside in 0.1 M sodium phosphate pH 7.2 buffer containing 0.13% Triton X-100 as substrate. These plates were read on a Molecular Devices Vmax spectrophotometer, at a 405 nm endpoint reading. Data were reduced using RoboFit.

The results were expressed as percent of maximum or fold activation calculated by the following formulas: fold activation=(((SPAP−SPAPsubstrate blank avg.)/(β-gal−β-gal substrate blank avg.))−DMSO vehicle avg.)/DMSO vehicle avg, and % max.=(fold activation of unknown/positive control fold activation avg.)×100. Curves were fit from these data using RoboFit to determine $EC_{50}$'s using the following equation:

$$Y=((V\max*x)/(K+x))+Y2.$$

$pEC_{50}$ values were >6.0 for all examples with the exception of Examples 13, 18, and 19, which each had $pEC_{50}$<6.0.

Although specific embodiments of the present invention have been illustrated and described in detail, it is to be expressly understood that the invention is not limited thereto. The above detailed description of the preferred embodiment is provided for example only and should not be construed as constituting any limitation of the invention. Modifications will be obvious to those skilled in the art, and all modifications that do not depart from the spirit of the invention are intended to be included within the scope of the appended claims.

What is claimed is:

1. A compound selected from the group consisting of:
   (2E)-3[4-(5,5,8,8-Tetramethyl-5,6,7,8-tetrahydro-2-naphthalenyl)-4,5,6,7-tetrahydro-1-benzofuran-2-yl]-2-propenoic acid;
   (2E)-3-[4-(3,5,5,8,8-pentamethyl-5,6,7,8-tetrahydro-2-naphthalenyl)-4,5,6,7-tetrahydro-1-benzofuran-2-yl]-2-propenoic acid;
   (2E)-3-[4-(3-methoxy-5,5,8,8-tetramethyl-5,6,7,8-tetrahydro-2-naphthalenyl)-4,5,6,7-tetrahydro-1-benzofuran-2-yl]-2-propenoic acid;
   (2E)-3-[4-(5,5,6,8-tetramethyl-3-propoxy-5,6,7,8-tetrahydro-2-naphthalenyl)-4,5,6,7-tetrahydro-1-benzofuran-2-yl]-2-propenoic acid;
   (2E)-3-[6-methyl-4-(5,5,8,8,-tetramethyl-5,6,7,8-tetrahydro-2-naphthalenyl)-4,5,6,7-tetrahydrofuro[2,3-c]pyridin-2-yl]-2-propenoic acid;
   (2E)-3-[4-(5,5,8,8-tetramethyl-5,6,7,8-tetrahydro-2-naphthalenyl)-4,5,6,7-tetrahydro-1-benzothien-2-yl]-2-propenoic acid;
   (2E)-3-4-(5,5,8,8-tetramethyl-5,6,7,8-tetrahydro-2-naphthalenyl)-4,5,6,7-tetrahydro-1,3-benzoxazol-2-yl]-2-propenoic acid;
   (2E)-3[4-(4-Isopropoxy-1-naphthalenyl)-4,5,6,7,-tetrahydro-1-benzofuran-2-yl]-2-propenoic acid;
   4-(5,5,8,8-Tetramethyl-5,6,7,8-tetrahydro-2-naphthalenyl)-4,5,6,7-tetrahydro-1-benzofuran-2-carboxylic acid;
   [4-(5,5,8,8,-Tetramethyl-5,6,7,8-tetrahydro-2-naphthalenyl)-4,5,6,7-tetrahydro-1-benzofuran]-2-(2,4-thiazolidinedione);
   [4-(5,5,8,8-Tetramethyl-5,6,7,8-tetrahydro-2-naphthalenyl)-4,5,6,7-tetrahydro-1-benzothien-2-yl]-2-propionic acid;
   4-(5,5,8,8-Tetramethyl-5,6,7,8-tetrahydro-2-naphthalenyl)-4,5,6,7-tetrahydro-1-benzofuran]-2-(2,3(cis)propenoic acid;
   (2E)-3-{4-[7-Dimethylamino)-1-methyl-2,3-dihydro-1H-indol-5-yl]-4,5,6,7-tetrahydro-1-benzofuran-2-yl}prop-2-enoic acid;
   (2E)-3-[4-butyl-4-(5,5,8,8-tetramethyl-5,6,7,8-tetrahydronaphthalen-2-yl)-4,5,6,7-tetrahydro-1-benzofuran-2-yl]prop-2-enoic acid; or
   salts, solvates, or pharmaceutically functional derivatives thereof.

* * * * *

UNITED STATES PATENT AND TRADEMARK OFFICE
CERTIFICATE OF CORRECTION

| | |
|---|---|
| PATENT NO. | : 7,173,134 B2 |
| APPLICATION NO. | : 10/490805 |
| DATED | : February 6, 2007 |
| INVENTOR(S) | : Haffner et al. |

It is certified that error appears in the above-identified patent and that said Letters Patent is hereby corrected as shown below:

Column 56 (Lines 4-6) should read as follows:

(2E)-3-[4-(5,5,8,8-tetramethyl-3-propoxy-5,6,7,8-tetrahydro-2-naphthalenyl)-4,5,6,7-tetrahydro-1-benzofuran-2-yl]-2-propenoic acid;

Column 56 (Lines 13-15) should read as follows:

(2E)-3-[4-(5,5,8,8-tetramethyl-5,6,7,8-tetrahydro-2-naphthalenyl)-4,5,6,7-tetrahydro-1-benzothien-2-yl]-2-propenoic acid;

Signed and Sealed this

Twenty-ninth Day of May, 2007

JON W. DUDAS
*Director of the United States Patent and Trademark Office*